(12) United States Patent
Burnouf et al.

(10) Patent No.: US 9,133,240 B2
(45) Date of Patent: Sep. 15, 2015

(54) COMPOUNDS BINDING TO THE BACTERIAL BETA RING

(75) Inventors: Dominique Burnouf, Brumath (FR); Annick Stote, Strasbourg (FR); Gilles Guichard, Gradignan (FR); Jérôme Wagner, Strasbourg (FR); Vincent Olieric, Endingen (CH)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/111,854

(22) PCT Filed: Apr. 13, 2012

(86) PCT No.: PCT/IB2012/051840
§ 371 (c)(1),
(2), (4) Date: Dec. 3, 2013

(87) PCT Pub. No.: WO2012/140619
PCT Pub. Date: Oct. 18, 2012

(65) Prior Publication Data
US 2014/0287989 A1    Sep. 25, 2014

(30) Foreign Application Priority Data

Apr. 15, 2011 (EP) ..................................... 11162733

(51) Int. Cl.
*A61K 38/08* (2006.01)
*C07K 7/06* (2006.01)
*C07K 14/245* (2006.01)
*C07K 14/195* (2006.01)

(52) U.S. Cl.
CPC . *C07K 7/06* (2013.01); *A61K 38/08* (2013.01); *C07K 14/195* (2013.01); *C07K 14/245* (2013.01)

(58) Field of Classification Search
None
See application file for complete search history.

(56) References Cited

FOREIGN PATENT DOCUMENTS

WO    02/38596    5/2002

OTHER PUBLICATIONS

Kurtz, Mareike et al; "Interaction of the sliding clamp beta-subunit and had, a dnaa-related protein." J. Bateriol (2004) 186(11) p. 3580-3515.*
Stetter, Karl O.; "Extremophiles and their adaptation to hot environments." FEBS Lett (1999) 452 p. 22-25.*
The May 15, 2014 entry of the blog "in the pipeline" by Derek Lowe "The daily show on finding new antibiotics." http://pipeline.corante.com/archives/2014/05/15/the_daily_show_on_finding_new_antibiotics.php?utm_source=feedburner&utm_medium=feed&utm_campaign=Feed%3A+InThePipeline+(ln+the+Pipeline).*
Burnouf et al., Structural and Biochemical Analysis of Sliding Clamp/ Ligand Interactions Suggest a Competition Between Replicative and Translesion DNA Polymerases, Journal of Molecular Biology, 335, pp. 1187-1197, 2004.
Georgescu et al., Structure of a Small-Molecule Inhibitor of a DNA Polymerase Sliding Clamp, Proceedings of the National Academy of Sciences, 105, pp. 11116-11121, 2008.
Darymple et al., Identification of Putative DnaN-binding Motifs in Plasmid Replication Initiation Proteins, Plasmid, 57, pp. 82-88, 2007.

* cited by examiner

*Primary Examiner* — Maury Audet
*Assistant Examiner* — Fred Reynolds
(74) *Attorney, Agent, or Firm* — Morgan, Lewis & Bockius LLP

(57) ABSTRACT

The present invention relates to compounds which bind to the hydrophobic pocket of the β clamp, i.e., to the surface of the β ring with which said protein interacts with other proteins of the bacterial replication complex during DNA replication. These compounds are derived from the acetylated peptide AcQLDLF (P6) to improve their affinity to their target.

16 Claims, 11 Drawing Sheets

A.

B.

C.

A.

B.

A.

B.

|  | P1 | P5 | P3 | P15 | P6 | P7 | P11 | P12 | P14 | P13 |
|---|---|---|---|---|---|---|---|---|---|---|
| IC50 Biochemical assay (µM) | nd | nd | 7 | 6,7 | 4,5 | 2,8 | 2 | 0,3 | 0,125 | 0,25 |
| IC50 SPR (µM) | 8.85 | 12.44 | 8.62 | 1.91 | 1.12 | 0.17 | 0.26 | 0.16 | 0.077 | 0.096 |

A.

B.

A.

P12, N= 1.06, $K_D$= 122nM    P14, N= 0.906, $K_D$= 55nM

B.

Figure 9:
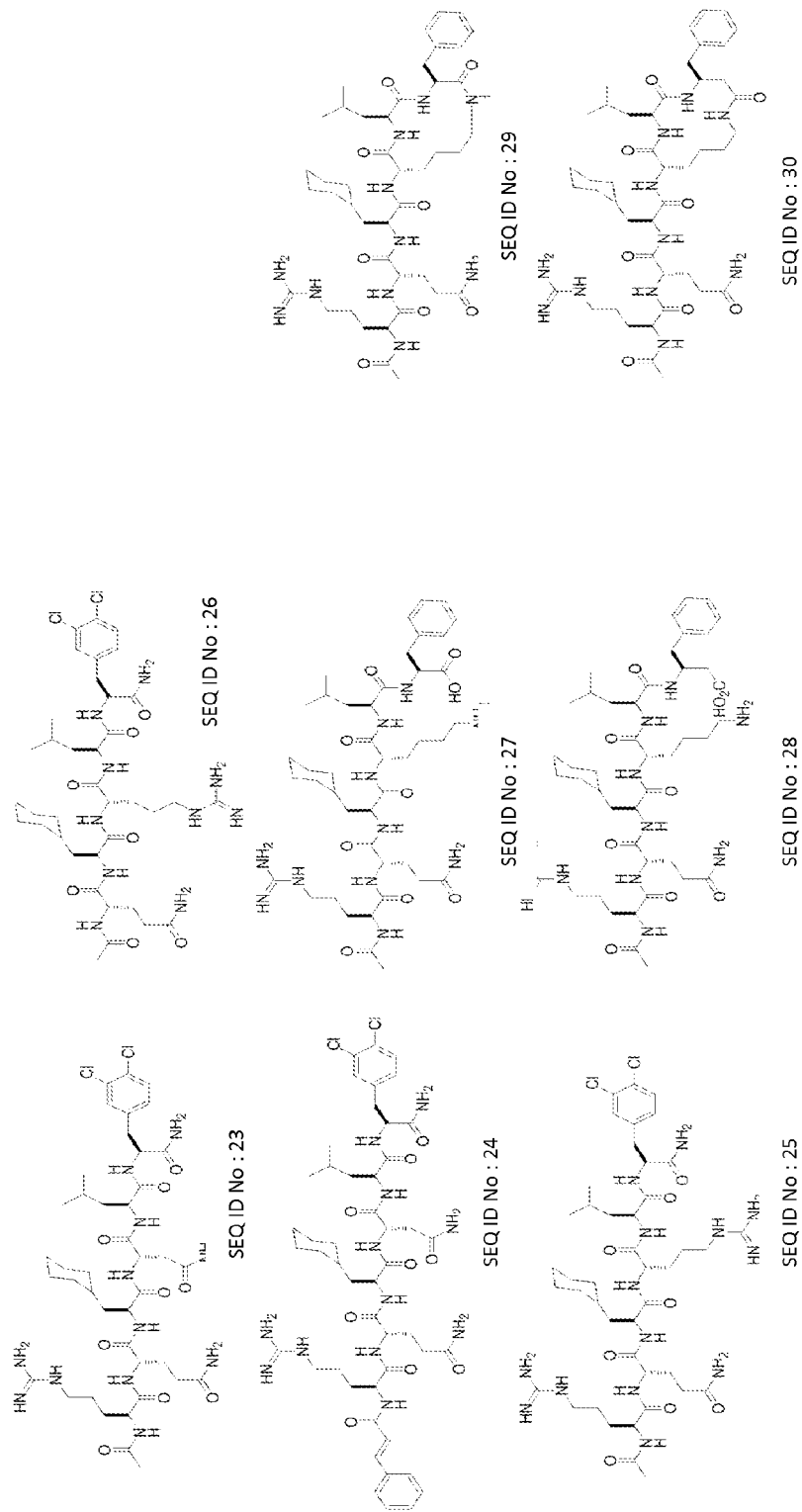

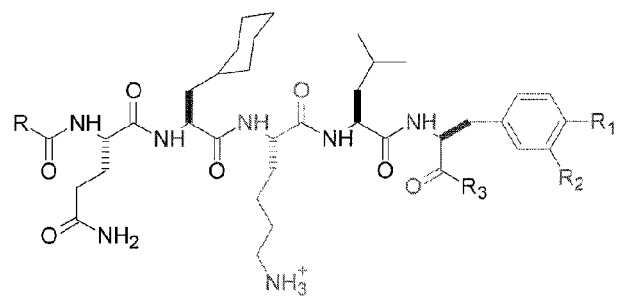
A
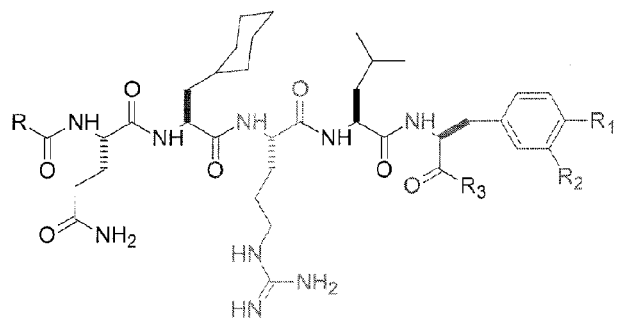
B
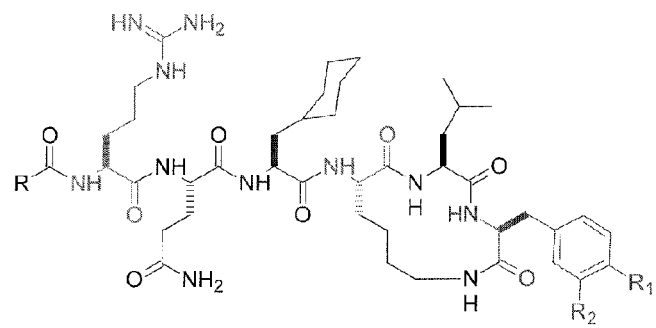
C
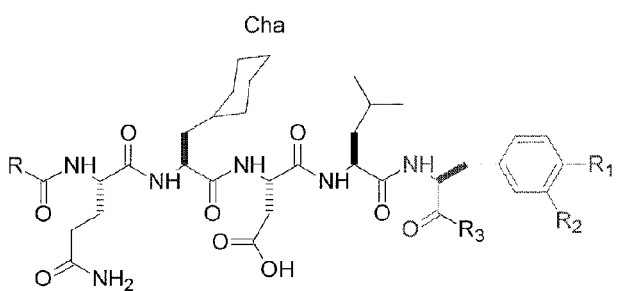
D
Figure 9 (A-D)

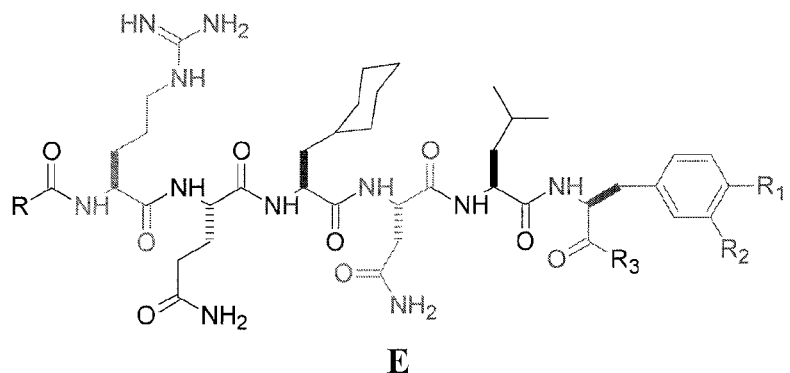
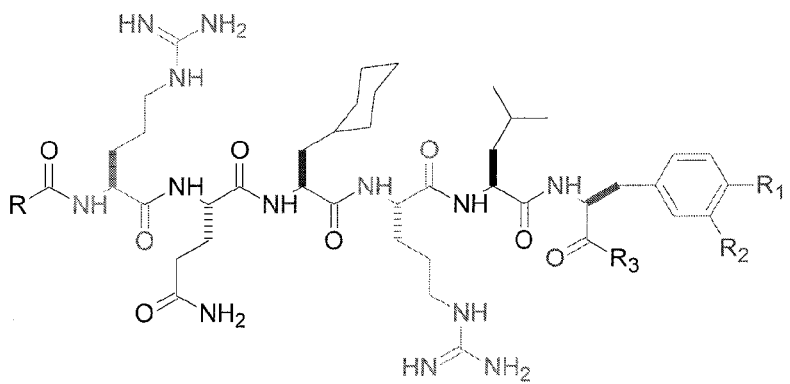
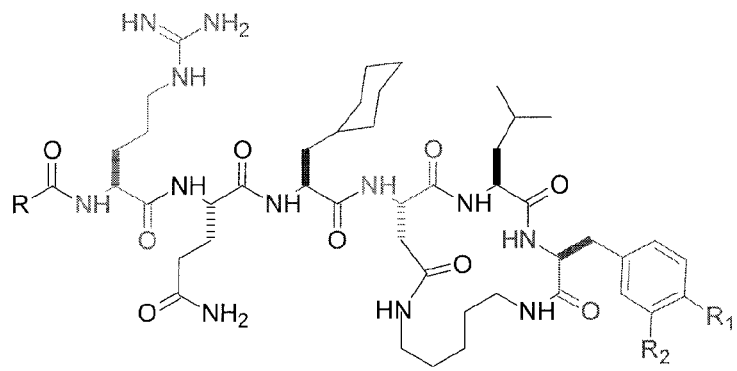
Figure 9 (E-G)

COMPOUNDS BINDING TO THE BACTERIAL BETA RING

SEQUENCE LISTING SUBMISSION VIA EFS-WEB

A computer readable text file, entitled "045636-5242-SubstituteSequenceListing.txt" created on or about 14 Apr. 2015, with a file size of about 13 kb contains the sequence listing for this application and is hereby incorporated by reference in its entirety.

The present invention relates to bacterial replication. More precisely, the present invention concerns compounds which bind to the hydrophobic pocket of the β clamp, i.e., to the surface of the β ring with which said protein interacts with other proteins involved in DNA metabolism.

In all three domains of life, multicomponents complexes, the so-called replisomes, have evolved to ensure the faithful replication of chromosomal DNA. One central protein of these complexes forms a ring that encircles and slides along the double stranded DNA[1, 2]. A physical interaction between the clamp and the chromosomal replicase confers a high processivity to the enzyme[3]. In bacteria, the processivity factor, also referred to as the β ring, is a homodimer which results from the head-to-tail association of two monomers, each of them being shaped in three globular sub-domains[1]. In eukaryotes and archae, the β homolog factor, PCNA (for Proliferating Cell Nuclear Antigen), is a homotrimer with each monomer organized in two sub-domains[2, 4].

Beside their role as processivity factors for chromosomal replicases, β and PCNA clamps also participate in various protein-protein interactions. They notably act as landing platforms for factors involved in DNA metabolism and cell cycle regulation[5], particularly DNA polymerases involved in translesion synthesis[6, 7], and factors promoting DNA repair[8, 9, 10]. All these factors possess a small conserved peptide sequence, which binds into a hydrophobic pocket located on one side of the ring. Noteworthy, these pockets differ significantly between bacterial rings and PCNA. A bioinformatics analysis performed on putative β ring partners led to define the bacterial consensus binding peptide QL[S/D]LF[10]. The absolute requirement of the interacting peptide for β ring partners binding has been further demonstrated biochemically and physiologically[11, 12, 13, 14]. Finally, the interaction between the ring and the interacting peptide of different β binding proteins have been structurally characterized[15, 16, 17, 18]. The peptide binding site is formed by a deep leucine-rich hydrophobic pocket (subsite 1) located between sub-domains two and three of the β monomer and connected via a groove to a second sub-site (subsite 2) located in sub-domain three[17] (FIG. 1C). An additional interaction has also been observed in the case of the polymerase Pol IV, between the little finger domain of the enzyme and the edge of the β ring[16].

The major contribution of the peptide-mediated interaction to a successful DNA replication and ultimately to cell survival, both in prokaryotes and eukaryotes, makes the ring interacting pockets potential targets for the development of new antibacterial or anticancer drugs, respectively. In a recent report, a chemical compound was identified from a library and shown to bind into the leucine rich sub-domain of the $E.\ coli$ β ring interacting pocket with an affinity of $10^{-5}$ M[18].

In the experimental work described below, a different, structure-based strategy was used to design short peptides with improved affinities for the β interacting pocket. The first step of this approach was to decipher the molecular basis of the interaction of the natural ligand in the binding pocket. Then, using these data, a first peptide (SEQ ID No: 6, P6) was designed, which was then further modified to improve its affinity. Several biophysical and biochemical methods were used to measure the strength of the interaction and to characterize the structure of the most efficient complexes formed. As a result, the binding efficiency of the modified ligand was improved by two orders of magnitude, reaching $10^{-8}$ M range.

Due to their very good affinity for the β interacting pocket, the compounds described in the present text are very promising leads for new antibiotic compounds.

According to a first aspect, the present invention pertains to a compound of formula (I)

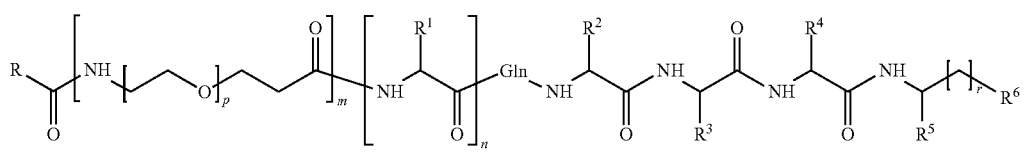

(I)

wherein

Gln is glutamine;

R is selected in the group consisting of a $C_{1-12}$-alkyl group optionally substituted by a $C_{6-10}$-aryl group, a $C_{2-12}$-alkenyl group optionally substituted by a $C_{6-10}$-aryl group, a $C_{3-6}$-cycloalkyl group, a $C_{6-10}$-aryl group optionally substituted by a $C_{1-4}$-alkyl, and a $C_{1-5}$-alkyl-(O—$CH_2$—$CH_2$)$_t$— group with t being an integer from 0 to 20 inclusive;

$R^1$ is the side chain of arginine or lysine (n.b.: when n>1, each $R^1$ is, independently from each other, the side chain of arginine or lysine);

$R^2$ is a —($CH_2$)—$C_{3-6}$-cycloalkyl group optionally substituted by a halogen and/or by a group selected amongst —$NH_2$, —NH—CO—$R^a$, —$CO_2$H, —$NHR^a$ and —$NR^aR^b$, wherein $R^a$ and $R^b$ are independently a $C_{1-4}$-alkyl group;

$R^3$ is selected in the group consisting of a $C_{1-8}$-alkyl group, the side chain of arginine or lysine, —($CH_2$)$_q$—$CO_2R^{7a}$, —($CH_2$)$_q$—CO—$NHR^{7b}$, —$CH_2OR^8$ and —($CH_2$)$_q$ $NHR^9$, wherein q is 1, 2, 3 or 4, $R^{7a}$ is a hydrogen atom, a $C_{1-8}$-alkyl group, a $C_{4-12}$-alkylene group forming together with $R^6$ a lactone or a polyether ring, or a $C_{4-12}$-alkenylene, forming together with $R^6$ a lactone or a polyether ring, $R^{7b}$ is a hydrogen atom, a $C_{1-8}$-alkyl group, or —($CH_2$)$_{q'}$—NH— with q' being an integer between 2 and 8 inclusive and forming together with $R^6$ a lactam, $R^8$ is a hydrogen atom, a $C_{1-8}$-alkyl group, a $C_{4-12}$-alkylene group forming together with $R^6$ a lactone or a polyether ring, or a $C_{4-12}$-alkenylene, forming together with $R^6$ a lactone or a polyether ring, $R^9$ is a hydrogen atom, or $R^9$ together with $R^6$ form a lactam;

$R^4$ is a $C_{1-8}$-alkyl group optionally substituted by a $C_{3-6}$-cycloalkyl group, or a halogen-$C_{1-4}$-alkyl group;

$R^5$ is selected in the group consisting of a —($CH_2$)—$C_{3-6}$-cycloalkyl group; —($CH_2$—$CH_2$)—$C_{3-6}$-cycloalkyl group; a —($CH_2$)—$C_{6-10}$-aryl group optionally substituted by a halogen, a $C_{1-2}$ alkyl group and/or a $C_{1-2}$ alkoxy group; a —($CH_2$—$CH_2$)—$C_{6-10}$-aryl group optionally substituted by a halogen, a $C_{1-2}$ alkyl group and/or a $C_{1-2}$ alkoxy group; a —($CH_2$)—$C_{5-10}$-heteroaryl group optionally substituted by a halogen and/or a $C_{1-2}$ alkyl group; a —($CH_2$—$CH_2$)—$C_{5-10}$-heteroaryl group optionally substituted by a halogen and/or a $C_{1-2}$ alkyl group;

$R^6$ is —$CO_2H$, —$CO_2R^{10}$, —CO—$NH_2$, —CO—$NHR^{10}$, —$OR^{10}$ when r is 1 or 2, —NH—CO—$NHR^{10}$ when r is 1 or 2, or $R^6$ is —CO—, —CO—O— or —O— and forms a lactam, a lactone, or a polyether ring with $R^{7a}$, $R^{7b}$, $R^8$ or $R^9$; wherein $R^{10}$ is a $C_{1-8}$-alkyl group optionally substituted by a $C_{6-10}$-aryl group; a $C_{3-6}$-cycloalkyl group; a $C_{6-10}$-aryl group optionally substituted by a halogen, a $C_{1-2}$-alkyl group and/or a $C_{1-2}$-alkoxy group;

m is 0 or 1;

n is an integer from 0 to 9 inclusive;

p is an integer from 0 to 10 inclusive;

r is 0, 1 or 2.

In the above formula (I), the peptide linkages (—CO—NH—) can be replaced or modified to obtain synthetic pseudopeptides or peptidomimetics in which the peptide bond is modified, especially to become more resistant to proteolysis, provided the immunogenicity of and the toxicity of the molecule is not increased by this modification, and providing the pseudopeptide retains its affinity for the β interacting pocket.

The following definitions are set forth to illustrate and define the meaning and scope of the various terms used to describe the invention herein. The term "$C_{1-12}$-alkyl" refers to a branched or straight-chain monovalent saturated aliphatic hydrocarbon group of 1 to 12 (inclusive) carbon atoms. Similarly, the terms: "$C_{1-8}$-alkyl", "$C_{1-5}$-alkyl", "$C_{1-4}$-alkyl", "$C_{1-2}$-alkyl" and the like refer to branched or straight-chain monovalent saturated aliphatic hydrocarbon groups of, respectively, 1 to 8 (inclusive), 1 to 5 (inclusive), 1 to 4 (inclusive), 1 to 2 carbon atoms. This term is further exemplified by groups as methyl, ethyl, propyl, butyl, pentyl, hexyl, heptyl, octyl, nonyl, decyl, undecyl, dodecanyl and their branched isomers. The "alkyl" group can optionally be mono-, di-, tri- or multiply-substituted by a halogen and/or a $C_{6-10}$ aryl group, as defined below.

The term "$C_{1-8}$-alkyl-(O—$CH_2$—$CH_2$)$_t$-" refers to a —(O—$CH_2$—$CH_2$)$_t$— substituted $C_{1-8}$-alkyl group wherein the alkyl group is as defined above and t is an integer from 0 to 20 (inclusive), preferably 0, 1, 2, 3, 4, 5, 6, 7, 8, 9 or 10. Preferred —(O—$CH_2$—$CH_2$)$_t$— substituted alkyl group is a $C_{1-5}$-alkyl-(O—$CH_2$—$CH_2$)$_t$— group with t and alkyl as defined above.

The term "$C_{2-12}$-alkenyl" refers to a branched or straight-chain monovalent unsaturated aliphatic hydrocarbon group having one or more carbon double bonds, of 2 to 12 (inclusive) carbon atoms, preferably 2 to 8 (inclusive) carbon atoms, more preferably 2 to 4 (inclusive) carbon atoms. This term is further exemplified by groups as vinyl, propylenyl, butenyl, pentenyl, hexenyl, heptenyl, octenyl, nonenyl, decenyl, undecenyl, dodecenyl and their straight-chain and branched and stereo isomers. The "alkenyl" group can optionally be mono-, di-, tri- or multiply-substituted by a halogen and/or a $C_{6-10}$-aryl group, as defined below.

The term "$C_{1-12}$-alkylene" refers to a divalent $C_{1-12}$-alkyle with alkyl as defined above. Similarly, terms such as "$C_{4-12}$-alkylene" or "$C_{4-8}$-alkylene" and the like, refer to divalent $C_{4-12}$-alkyl or divalent $C_{4-8}$-alkyle group where alkyl is defined above. Examples of alkylene groups are —($CH_2$)—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, —($CH_2$)$_9$—, —($CH_2$)$_{10}$—, —($CH_2$)$_{11}$—, —($CH_2$)$_{12}$—.

The term "$C_{4-12}$-alkenylene" refers to a divalent $C_{4-12}$-alkenyl of formula —($CH_2$)$_x$—(CH=CH)$_y$—($CH_2$)$_z$— wherein x and z are, independently, 0, 1, 2, 3, 4, 5, 6, 7 or 8 and y is 1, 2, 3 or 4. Similarly, the term "$C_{4-8}$-alkenylene", refers to a divalent $C_{4-8}$-alkenyl. Examples of alkenylene groups include butenyl, pentenyl, pentadienyl, hexenyl, hexadienyl, heptenyl, heptadienyl, octenyl, octadienyl, nonenyl, nonadienyl, decenyl, decadienyl, undecenyl, undecadienyl, undodecenyl, undodecadienyl, and their straight-chain and branched and stereo-isomers.

The term "$C_{3-6}$-cycloalkyl" refers to a saturated or partially unsaturated cyclic hydrocarbon group having 3 to 6 (inclusive) carbon atoms. This term is further exemplified by groups as cyclopropyl, cyclobutyl, cyclopentyl, and cyclohexyl. The "$C_{3-6}$-cycloalkyl" group can optionally be mono-, di-, tri- or multiply-substituted by a halogen as defined below, a $C_{1-4}$-alkyl group as defined above, a —$NH_2$, a —NH—$CO_2H$, a —NH—CO—$R^a$, —$CO_2H$, —$NHR^a$ and/or —$NR^aR^b$ wherein $R^a$ and $R^b$ are independently a $C_{1-4}$-alkyl group as defined above.

The term —($CH_2$)—$C_{3-6}$-cycloalkyl group refers to a —$CH_2$— substituted $C_{3-6}$-cycloalkyl group wherein the cycloalkyl group is as defined above.

The term "$C_{6-10}$ aryl" refers to a monocyclic or bicyclic aromatic ring system of 6 to 10 (inclusive) carbon atoms, preferably 6 carbon atoms. This term is further exemplified by groups as phenyl and naphtyl. The $C_{6-10}$-aryl group can optionally be mono-, di-, tri- or multiply-substituted by a halogen as defined below and/or a $C_{1-4}$-alkyl group as defined above.

The terms "halo" or "halogen" refers to fluorine, chlorine, bromine and iodine.

The term "halogen-$C_{1-4}$-alkyl", refers to a halogen substituted $C_{1-4}$-alkyl group wherein both halogen and alkyl groups have the meaning as above. Preferred "halogen-$C_{1-4}$-alkyl" groups are fluorinated "halogen-$C_{1-4}$-alkyl" groups such as —$CF_3$, —$CH_2$—$CF_3$, —$CH(CF_3)_2$, —$CH(CH_3)(CF_3)$, —$C_4F_9$.

The term "$C_{1-12}$-alkoxy" refers to a branched or straight-chain monovalent saturated aliphatic hydrocarbon group of 1 to 12 (inclusive) carbon atoms attached to an oxygen atom. Similarly, the terms "$C_{1-8}$-alkoxy", "$C_{1-5}$-alkoxy", "$C_{1-4}$-alkoxy", "$C_{1-2}$-alkoxy" refer to branched or straight-chain monovalent saturated aliphatic hydrocarbon groups of, respectively, 1 to 8 (inclusive), 1 to 5 (inclusive), 1 to 4 (inclusive), 1 to 2 carbon atoms. Examples of "alkoxy" groups are methoxy, ethoxy, propoxy, butoxy, pentoxy, hexyloxy, heptyloxy, octyloxy, and their branched isomers.

The term "$C_{5-10}$-heteroaryl" refers to a heterocyclic aryl group containing 1 to 3 heteroatoms in the ring with the remainder being carbon atoms. In the said heterocyclic aryl group, suitable heteroatoms include, without limitation, sulfur and nitrogen. Exemplary heteroaryl groups include indolyl, azaindolyl, thiophenyl, benzothiophenyl, thioazolyl, benzothiazolyl. The heteroaryl group can optionally be mono-, di-, tri- or multiply-substituted by a halogen and/or a $C_{1-4}$-alkyl group, as defined above. When the heteroaryl group is mono-, di-, tri- or multiply-substituted by a $C_{1-4}$-alkyl group, said alkyl group is preferably a methyl group.

The term "polyether ring", refers ring containing 1, 2, or 3 ether groups, an ether group being an oxygen atom connected to two alkyl groups as defined above The term "lactone" refers to a closed ring containing an oxygen atom adjacent to a carbonyl group (—CO—O—). It can be considered as the condensation product of an —OH group with a —CO$_2$H group.

The term "lactam" refers to a closed ring containing an nitrogen atom adjacent to a carbonyl group (—CO—NH— or —CO—NR— with R being for example an alkyl group as defined above).

The terms "substituted" and "substitution and the like", refer to the replacement of one, two, three or more atoms in a given group by one, two, three or more suitable substituents, including, without limitation, a halogen, a $C_{6-10}$ aryl group, a $C_{1-4}$-alkyl group, a $C_{1-2}$-alkyl group, a $C_{1-2}$-alkoxy group, a —NH$_2$, a —NH—CO—R$^a$, —CO$_2$H, —NHR$^a$ and/or —NR$^a$R$^b$ wherein R$^a$ and R$^b$ are independently a $C_{1-4}$-alkyl group, or a mixture of those substituents.

In some embodiments of the invention, the compounds of the invention can contain one or more asymmetric centers and thus occur as racemates and racemic mixtures, single enantiomers, individual diastereoisomeric mixtures. All such isomeric forms of these compounds are included in the present invention, unless expressly provided otherwise.

In some embodiments, the compounds of the invention can contain one or more double bonds and thus occur as individual or mixtures of Z and/or E isomers. All such isomeric forms of these compounds are included in the present invention, unless expressly provided otherwise.

In the embodiments where the compounds of the invention can contain multiple tautomeric forms, the present invention also includes all tautomeric forms of said compounds unless expressly provided otherwise.

In the embodiment where $R^{7a}$ together with $R^6$ form a lactone or a polyether ring,
  $R^{7a}$ is $C_{4-12}$-alkylene, preferably $C_{4-8}$-alkylene group, and is linked to a —CO—O— or to a —O— functional group in $R^6$, or
  $R^{7a}$ is $C_{4-12}$-alkenylene, preferably $C_{4-8}$-alkenylene group, and is linked to a —CO—O— or to a —O— functional group in $R^6$.

In the embodiment where $R^{7b}$ together with $R^6$ form a lactam, $R^3$ is a —(CH$_2$)$_q$—CO—NHR$^{7b}$ and $R^{7b}$ is —(CH$_2$)$_{q'}$—NH— with q' being 2, 3, 4, 5, 6, 7 or 8.

In the embodiment where $R^9$ together with $R^6$ form a lactam, $R^3$ is a —(CH$_2$)$_q$NHR$^9$ and $R^9$ is a direct link between —(CH$_2$)$_q$NH— and a —CO— functional group in $R^6$.

In the embodiment where $R^8$ together with $R^6$ form a lactone or a polyether ring:
  $R^8$ is $C_{4-12}$-alkylene, preferably $C_{4-8}$-alkylene group, and is linked to a —CO—O— or to a —O— functional group in $R^6$, or
  $R^8$ is $C_{4-12}$-alkenylene, preferably $C_{4-8}$-alkenylene group, and is linked to a —CO—O— or to a —O— functional group in $R^6$.

The terms "β ring", "β protein" or "β clamp" herein designate the β subunit of a eubacterial DNA polymerase III, such as that of *E. coli*. The β subunit of DNA polymerase III of *E. coli* is in particular described in Kong et al. (1992)[1].

Further definitions are added in the text, when necessary.

Particular embodiments of the compounds according to the invention are described in the following more detailed specification.

According to a particular embodiment of the compounds according to the invention, the R group indicated in the above formula (I) is selected amongst a $C_{1-8}$-alkyl group optionally substituted by a $C_{6-10}$-aryl group, a $C_{2-8}$-alkenyl group optionally substituted by a $C_{6-10}$-aryl group or a $C_{1-5}$-alkyl-(O—CH$_2$—CH$_2$)$_t$— group with t being 0, 1, 2, 3, 4, 5, 6, 7, 8, 9 or 10. Preferably, R is a $C_{1-4}$-alkyl group optionally substituted by a $C_{6-10}$-aryl group or a $C_{2-4}$-alkenyl group optionally substituted by a $C_{6-10}$-aryl group. Indeed, as described in the experimental part below, the inventors have observed that a N-terminal acetylation of the peptide P5 (QLDLF, SEQ ID No: 5) leads to a 10-fold increase of the affinity of the peptide for the β interacting pocket.

When m is not null and p is >1 in the above formula (I), for example when m=1 and p=2, 3, 4, 5, 6, 7, 8, 9 or 10, the above-described compounds are pegylated. The pegylation contributes to the stability of the whole molecule and can also have a positive effect for the entry of said compound into bacterial cells.

Particular compounds according to the invention have one or several arginines and/or lysines at the N-terminal extremity of the peptide part of the compound. For example, n is 1, 2, 3, 4 or 5. Indeed, these positively charged residues are known to favor membrane crossing. This feature is however not compulsory, and other compounds according to the invention do not have such residues (n=0 in formula I).

The inventors have also observed that substitution of the second amino acid of Ac-QLDLF (SEQ ID No: 6, P6) by a beta-cyclohexyl-L-alanyl (hereafter designated as "Cha") leads to a further 6-fold increase of the affinity of said peptide with the β hydrophobic pocket. Other substitutions at the same position (see Table 4 in the experimental part) led to the above definition of $R^2$ in formula (I). According to an advantageous embodiment, $R^2$ is a —(CH$_2$)—$C_{3-6}$-cycloalkyl group.

By substituting the leucine of the acetylated peptide Ac-Gln-Cha-Asp-Leu-Phe 7 (SEQ ID No: 7, P7) by a number of different residues (see Table 5 of the experimental part below), the inventors could determine preferable embodiments for $R^4$ group, in order to optimize the binding to the interacting pocket of the β ring. Accordingly, $R^4$ is preferably selected amongst $C_{1-5}$-alkyl groups, especially branched ones (such as valine, leucine or homoleucine lateral chains, for example), or amongst $C_{1-3}$—, preferably $C_{1-2}$-alkyl groups optionally substituted by a $C_{3-6}$-cycloalkyl group (such as Cha and homoCha, for example).

As shown in Table 6 below, modifications introduced on the C-terminal phenylalanine benzyl ring led to an increase of the affinity of the molecule with the interacting pocket of the β ring. The binding affinity was found to increase with the size of the ring substituent (p-methyl<p-chloro<p-bromo<3,4-dichloro). The same table shows that other cyclic molecules can be used in this position. Contrarily, replacement of the phenylalanine lateral chain by a 2-amino-tetradecanoic acid led to a significant loss in affinity, thereby indicating an upper limit for the size of the group to be used at this position. Accordingly, in the compounds of the present invention, $R^5$ is preferably a —(CH$_2$)—$C_{6-10}$-aryl group optionally substituted by a halogen, a $C_{1-2}$ alkyl group and/or a $C_{1-2}$ alkoxy group.

As exemplified in the experimental part below, excellent affinities are obtained with linear molecules having a peptidic skeleton. Such molecules excellently mimic the binding part of the proteins which naturally interact with the β ring. When the compounds according to the invention are linear, $R^3$ and $R^6$ are as follows:

$R^3$ is selected in the group consisting of a $C_{1-8}$-alkyl group, the side chain of arginine or lysine, —$(CH_2)_q$—$CO_2R^{7a}$, —$(CH_2)_q$—CO—$NHR^{7b}$, —$CH_2OR^8$, —$(CH_2)_q$NHR$^9$, wherein q is 1, 2, 3, 4,
$R^{7a}$ is a hydrogen atom, or a $C_{1-8}$-alkyl group,
$R^{7b}$ is a hydrogen atom, or a $C_{1-8}$-alkyl group,
$R^8$ is a hydrogen atom, a $C_{1-8}$-alkyl group,
$R^9$ is a hydrogen atom;
and
$R^6$ is —$CO_2H$, —$CO_2R^{10}$, —CO—$NH_2$, —CO—$NHR^{10}$, —$OR^{10}$ when r is 1 or 2, —NH—CO—$NHR^{10}$ when r is 1 or 2; wherein
$R^{10}$ is a $C_{1-8}$-alkyl group optionally substituted by a $C_{6-10}$-aryl group; a $C_{3-6}$-cycloalkyl group; a $C_{6-10}$-aryl group optionally substituted by a halogen, a $C_{1-2}$-alkyl group and/or a $C_{1-2}$-alkoxy group.

It is to be noted that $R^6$ is directed towards the solvent. Hence, $R^6$ can be replaced by virtually any kind of molecule. For example, it can advantageously be replaced by or attached to a molecule which helps the crossing of membranes and/or the internalization by the bacteria. Non-limitative examples of such molecules are cell-penetrating peptides (CPP) (Classes and prediction of cell-penetrating peptides, Lindgren M, Langel U., Methods Mol Biol. 2011, 683, p. 3-19). In case a CPP or another molecule is covalently bound to the compound via $R^6$, a linker, made of one to 10, preferably 1 to 4 amino acids, can be added between the compound of the invention and said CPP. Such a linker can be, for example, a mere arginine or lysine, or a sequence of 2 to 4 amino-acids corresponding to the amino-acids immediately following the binding site of a natural ligand of the β ring, such as, for example, ASRQ (SEQ ID No: 31), which is the sequence following the binding site of the delta protein from the gamma complex. Indeed, as shown by Jeruzalmi et al (2001)[15, 15a], this protein exhibits a bend towards the outside of the pocket. Hence, a CPP bound via a ASRQ linker to a compound according to the invention would not hinder the interaction of said compound with the β ring.

According to a particular embodiment of the linear compounds of the present invention, $R^3$ and/or $R^6$ are as follows:
$R^3$ is selected in the group consisting of the side chain of arginine, the side chain of lysine, —$(CH_2)_q$—$CO_2R^{7a}$ and —$(CH_2)_q$—CO—$NHR^{7b}$, wherein
q is 1, 2, 3 or 4,
$R^{7a}$ is a hydrogen atom, or a $C_{1-8}$-alkyl group, and
$R^{7b}$ is a hydrogen atom, or a $C_{1-8}$-alkyl group,
and/or
$R^6$ is —$CO_2H$ or —CO—$NH_2$.

In an alternative embodiment, the compounds according to the present invention are cyclic, a cycle being made between the $R^3$ and $R^6$ groups. This bridge between $R^3$ and $R^6$ groups eliminates carboxylates, thereby improving the capacity of the compounds to enter bacterial cells, without impacting R5, which is necessary for anchoring the compound in the pocket, and for the subsequent conformational modification of said pocket. According to this embodiment, $R^3$ and $R^6$ are as follows:

$R^3$ is selected in the group consisting of —$(CH_2)_q$—$CO_2R^{7a}$, —$(CH_2)_q$—CO—$NHR^{7b}$, —$CH_2OR^8$, —$(CH_2)_q$NHR$^9$, wherein
q is 1, 2, 3 or 4,
$R^{7a}$ is a $C_{4-8}$-alkylene group forming together with $R^6$ a lactone or a polyether ring, or a $C_{4-8}$-alkenylene, forming together with $R^6$ a lactone or a polyether ring,
$R^{7b}$ is —$(CH_2)_{q'}$—NH— with q' being an integer from 2 to 8 inclusive and forming together with $R^6$ a lactam,
$R^8$ is a $C_{4-8}$-alkylene group forming together with $R^6$ a lactone or a polyether ring, or a $C_{4-8}$-alkenylene, forming together with $R^6$ a lactone or a polyether ring,
$R^9$ together with $R^6$ form a lactam;
$R^6$ is —CO—, —CO—O— or —O— and forms a lactam, a lactone, or a polyether ring with $R^{7a}$, $R^{7b}$, $R^8$ or $R^9$.

Particular compounds according to the present invention are described in the experimental part which follows. Particular compounds having a very good to excellent affinity for the β ring are: P7 (SEQ ID No: 7), P11 (SEQ ID No: 11), P12 (SEQ ID No: 12), P13 (SEQ ID No: 13), P14 (SEQ ID No: 14), P16 (SEQ ID No: 16), P17 (SEQ ID No: 17), P23 (SEQ ID No: 23), P24 (SEQ ID No: 24), P25 (SEQ ID No: 25), P26 (SEQ ID No: 26), P27 (SEQ ID No: 27).

As described in the experimental part below and as perfectly known by skilled artisans, several techniques exist to measure the affinity of two interacting proteins. These techniques may give slightly different results. However, the relative affinity of two compounds for the β ring is not dependent from the technique used for measuring said affinities (FIG. 4B). In a preferred embodiment of the compounds according to the invention, the affinity of said compounds for the interacting pocket of the bacterial β ring is at least twice the affinity of the acetylated peptide of sequence AcQLDLF (SEQ ID No: 6, P6) with said interacting pocket.

The compounds described above can advantageously be used as antibacterial agents, since they inhibit, at least partially, the interaction between the β protein and proteins that interact therewith by binding to its hydrophobic pocket.

A pharmaceutical composition comprising, as an active agent, a compound as above-described, is also part of the present invention.

FIGURES LEGENDS

Figure 1:
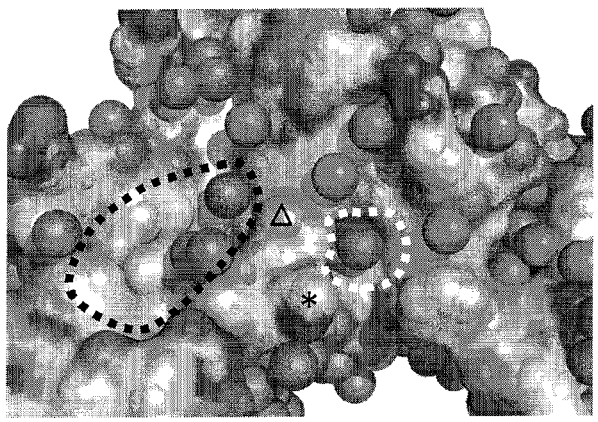
Figure 1:
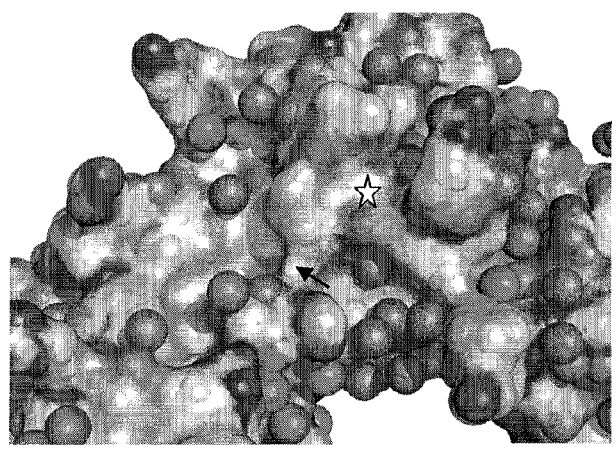
Figure 1:
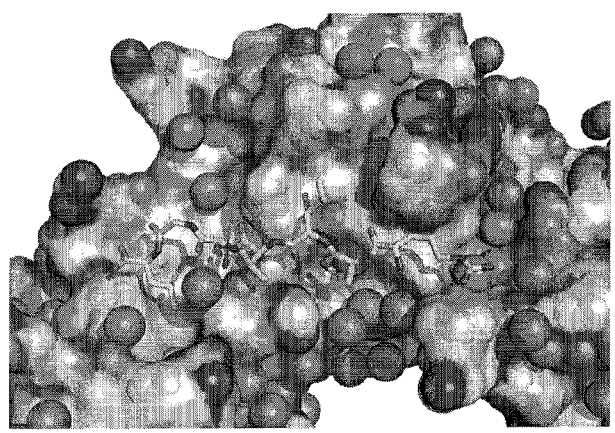

FIG. 1: Representations of the ligand binding pocket of the β ring of *E. coli*, from the co-crystal structure of the β ring with the C-terminal peptide of the *E. coli* DNA polymerase IV ($R_1Q_2L_3V_4L_5G_6L_7$, SEQ ID No: 32) (PDB code 1OK7). A: unbound pocket: the $M_{362}$ (Δ) residue is located close to the $H_{175}$ β residue (*) and obstructs the path between subsite 1 (black dots area) and subsite 2 (white dots area). Water molecules are represented as medium grey balls. B: bound pocket. The peptide has been removed. The movement of residue $M_{362}$ opens a cleft (dark arrow) which connects subsite 1 and subsite 2 and where the $V_4$ peptide residue interacts (see C). Water molecules are displaced, as compared to A, so that the peptide can fit into subsite 1. Note the opening of the platform (white star) between $M_{362}$ and $R_{365}$ where the $L_3$ peptide residue will be located. C: Same as B but with the peptide P1 bound into the pocket.

Figure 2:
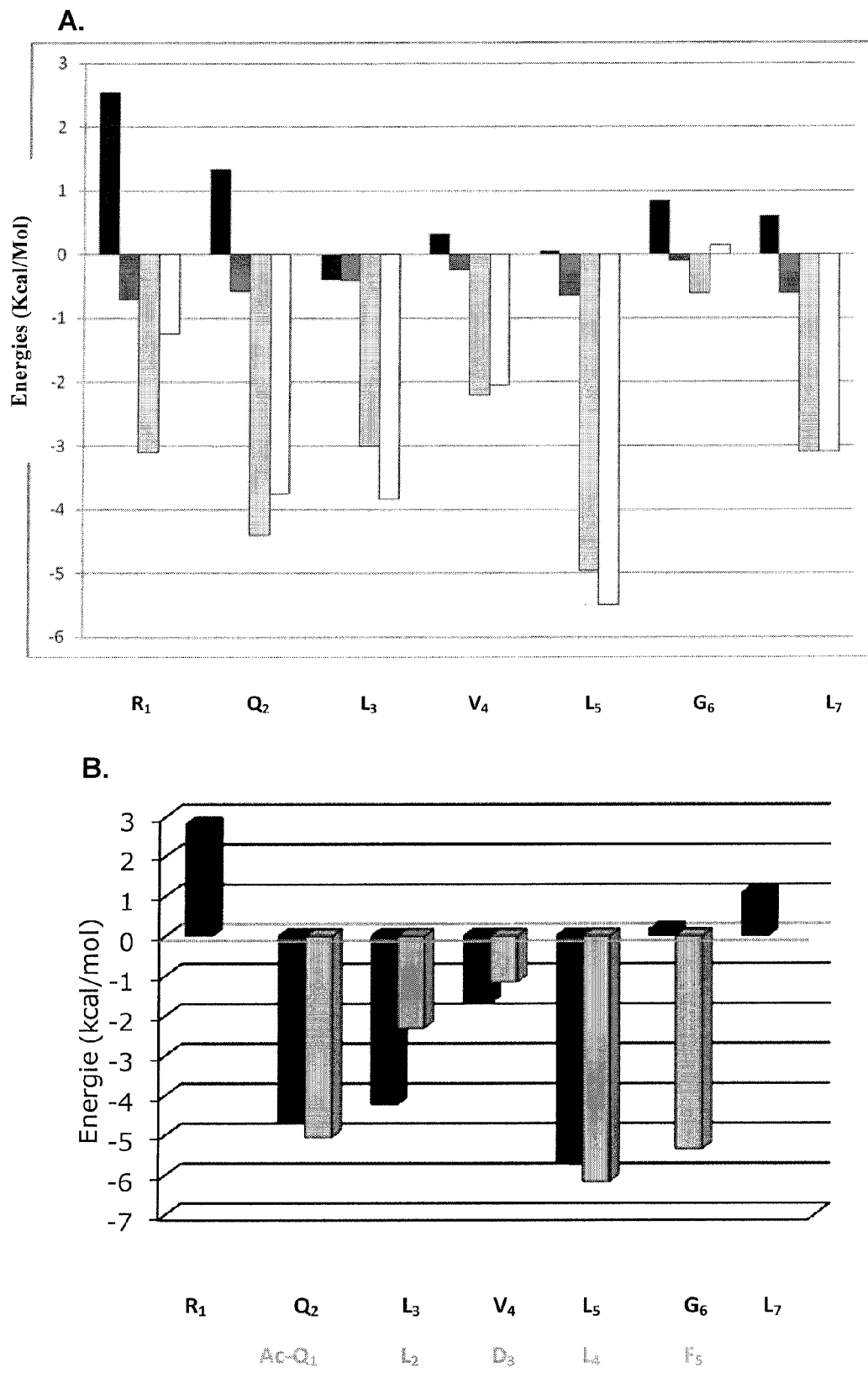

FIG. 2: A: Energetic contributions (Kcal/mol) of each peptide residue ($R_1Q_2L_3V_4L_5G_6L_7$, SEQ ID No: 32) for the interaction within the binding pocket of the β ring (PDB 1OK7). Black: electrostatic contribution, dark grey: solvent accessible surface contribution, light grey: Van der Waals contribution, white: total contribution. B: Single residue contribution (kcal/mol) to the peptide binding. Native peptide P1 of *E. coli* DNA polymerase IV, from the structure 1OK7, is in black. The pentapeptide P6 is in grey (PDB 3Q4J).

Figure 3:
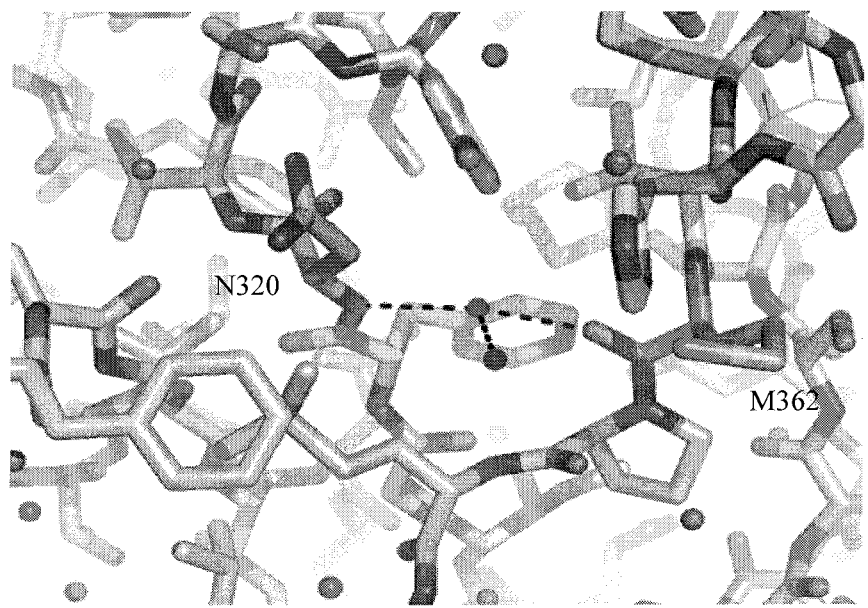
Figure 3:
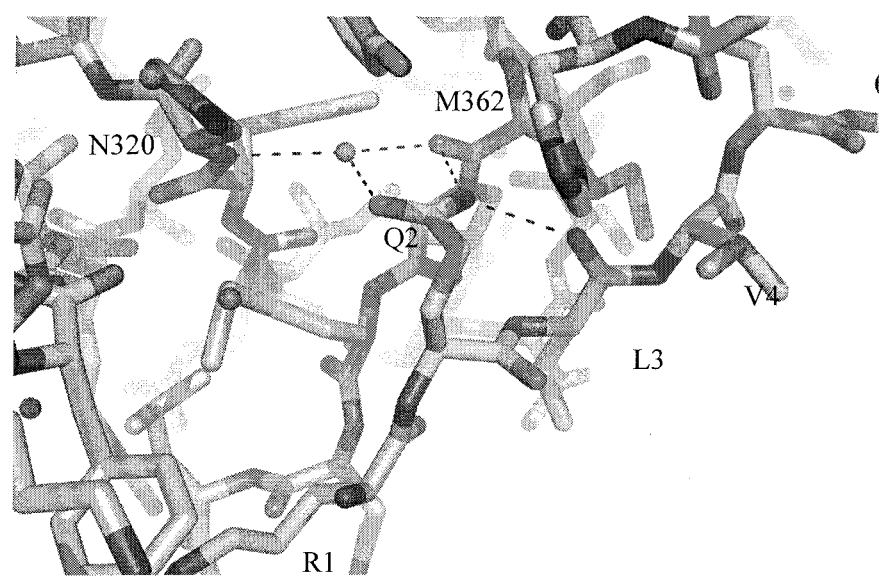

FIG. 3: Detailed connectivities between β residues $N_{320}$ and $M_{362}$ in subsite 2 of the binding pocket, in absence (A) or presence (B) of the peptide. Balls represent water molecules. From PDB structure 1OK7, incorporated herein by reference.

Figure 4:
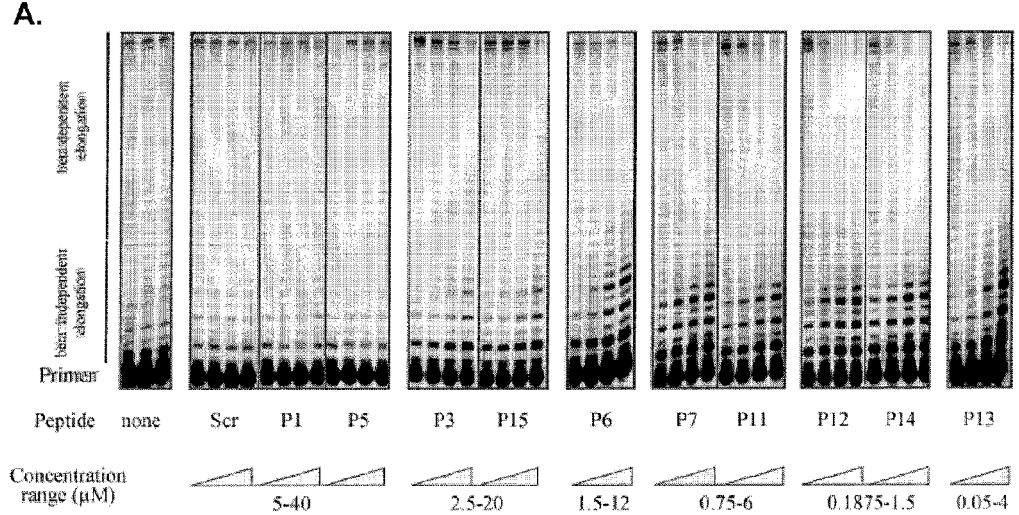
Figure 4:
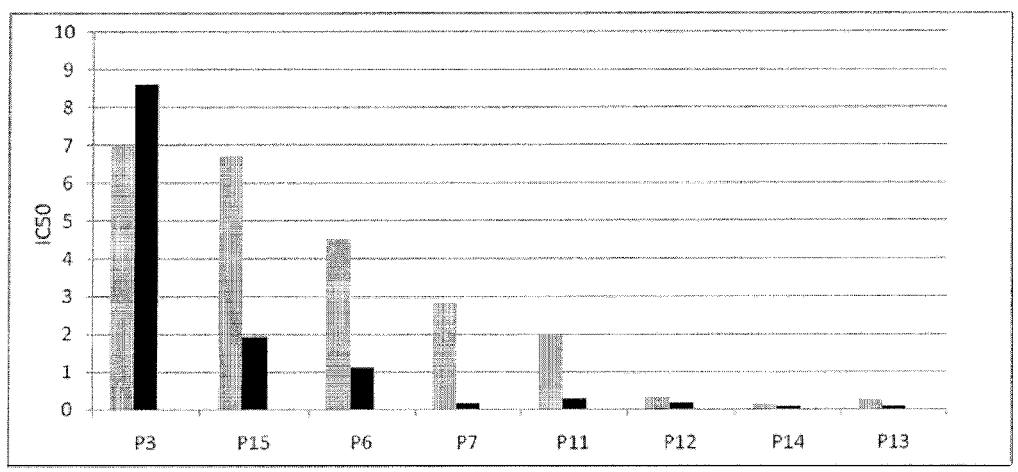

FIG. 4: Polymerase competition assay. A: the β dependant activity of PolIV DNA polymerase is challenged by increasing concentrations of various peptides B: the table displays the $IC_{50}$ determined for various peptides by the Pol IV based biochemical assay and the SPR assay. The histogram indicates that the same general trend is observed with both techniques despite a difference in sensitivity. Grey: biochemical assay, black: SPR assay. P15 sequence is Ac-RQLVLF, (SEQ ID No: 15), Scr: scrambled peptide: Ac-ChaFQLD, (SEQ ID No: 33).

Figure 5:
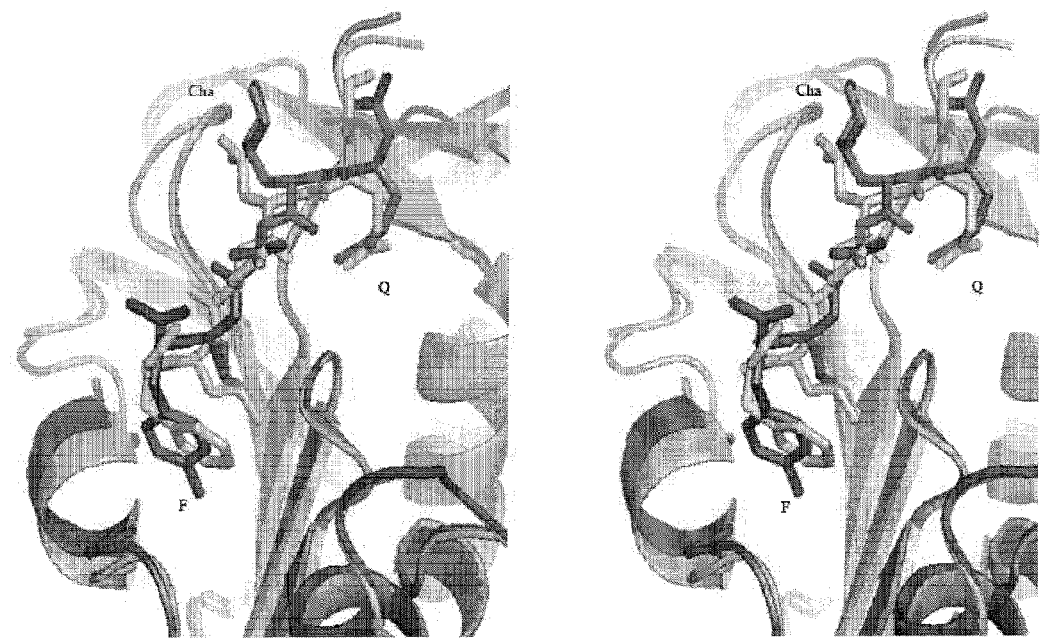
Figure 5:
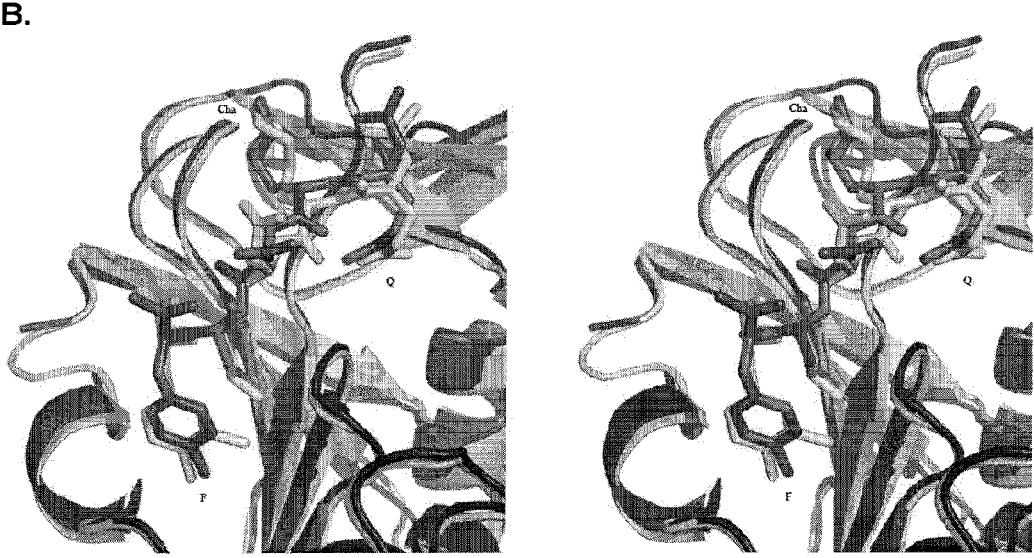

FIG. 5: Superimposition of peptide-β complexes. A: A P6-β complex (pale colors) is superimposed on P12-β complex (dark colors) (rmsd: 0.95 Å). The first (Gln) and last (Phe) peptide residues are indicated. The Cha group of P12 (SEQ ID No: 12) peptide occupies the same position as the $Leu_2$ residue of P6 (SEQ ID No: 6). The chloro-modified Phe residue of P12 is tilted toward the bottom of subsite 1 as compared to the cognate residue of P6. B: P14-β complex (pale colors) is superimposed on P12-β complex (dark colors) (rmsd: 0.56 Å). The chlorine atom in meta position forms an halogen bond with T172 residue.

Figure 6:
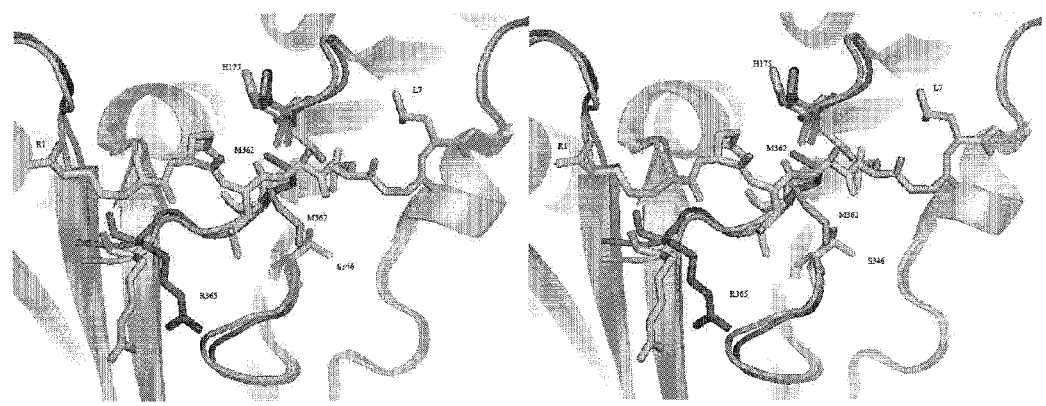

FIG. 6: Superposition of the peptide free (dark) and peptide bound (pale) interacting pockets of 1OK7 structure. In the absence of peptide, the $M_{362}$ side chain (dark) is located close to the $H_{175}$ residue (closed conformation), and separates subsite 1 and subsite 2. When the peptide is bound, the $M_{362}$ side chain (pale) is displaced away from the $H_{175}$ (open conformation) allowing the opening of a cleft in which the peptide can bind. Residue $R_{365}$ is also shifted upon peptide binding, triggering the opening of a small platform where the peptide $L_3$ residue locates.

Figure 7:
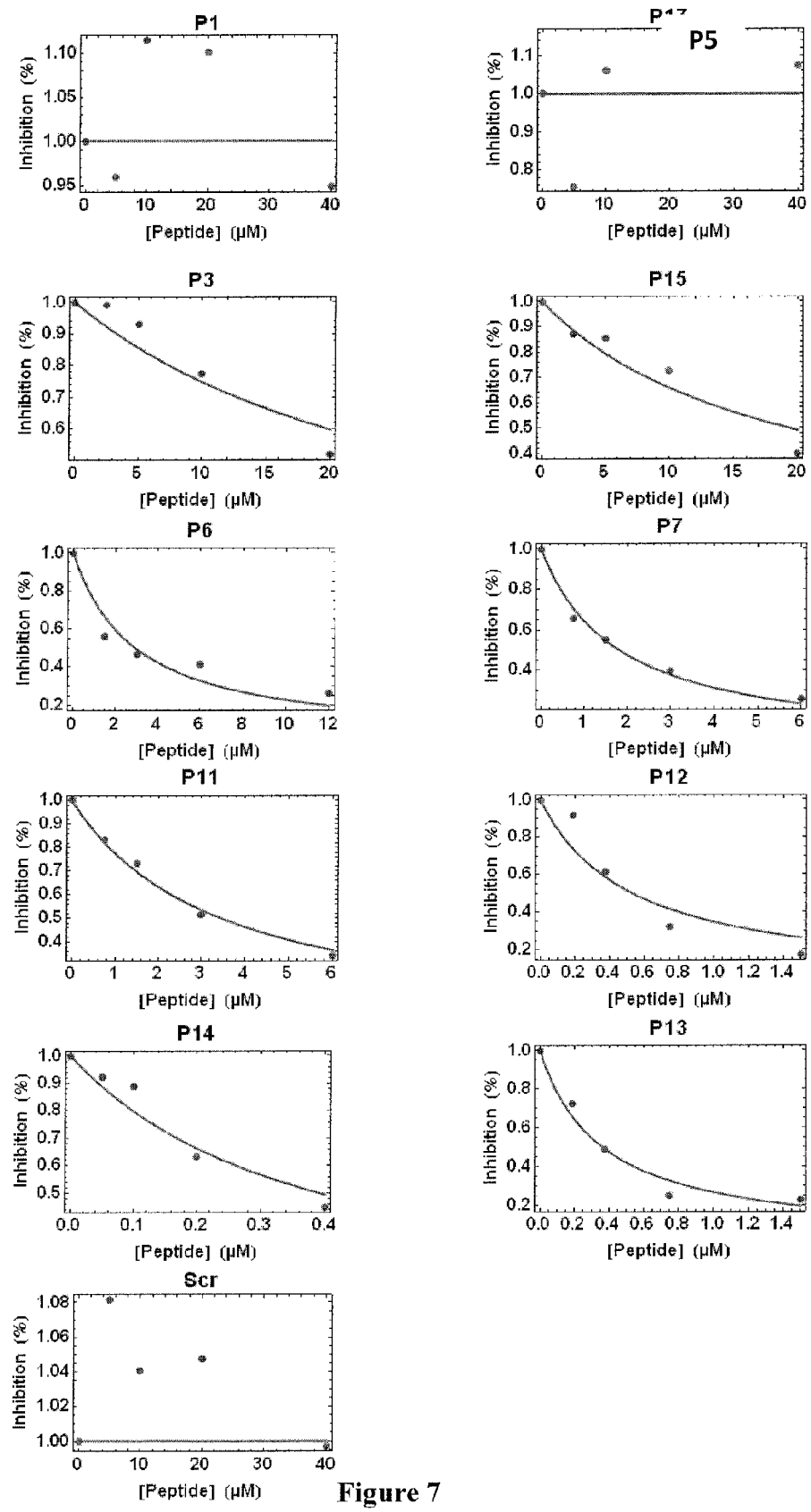

FIG. 7: Graphical representation of the quantitative analysis of polymerase competition assays performed with several peptides. The percentage of inhibition of β dependent E. coli DNA polymerase IV activity is plotted as a function of peptide concentration (μM). P15 sequence is Ac-RQLVLF (SEQ ID No: 15). Scr: scramble peptide: Ac-ChaFQLD (SEQ ID No: 33); (related to FIG. 4).

Figure 8:
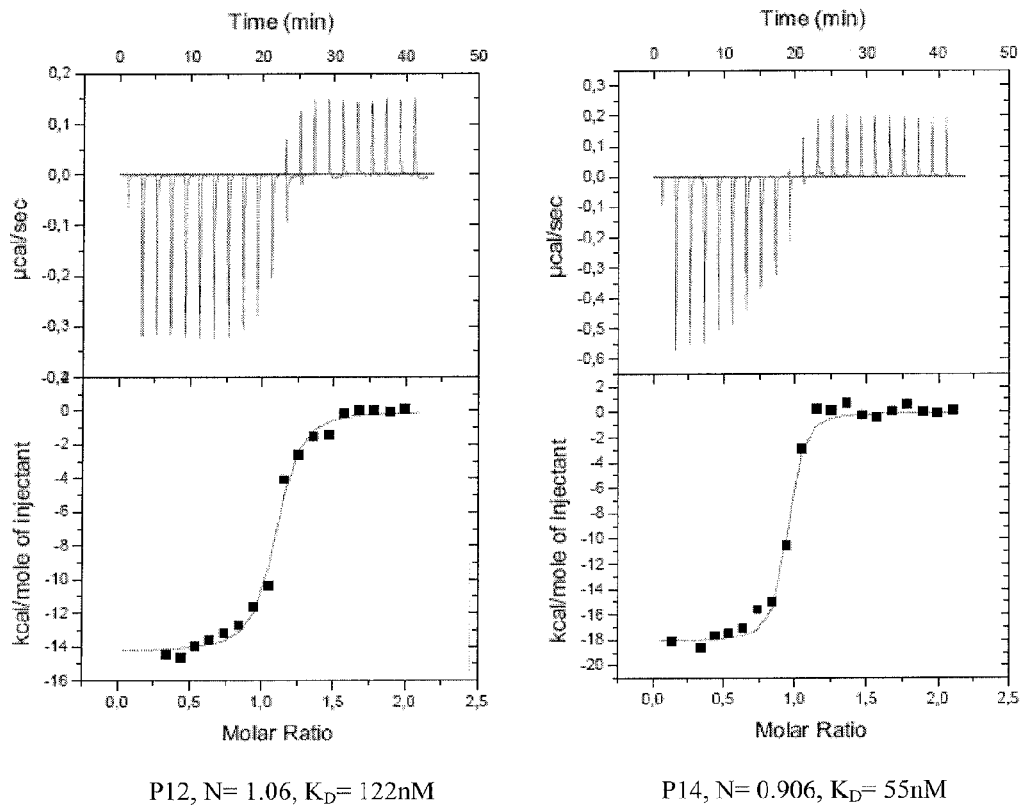
Figure 8:
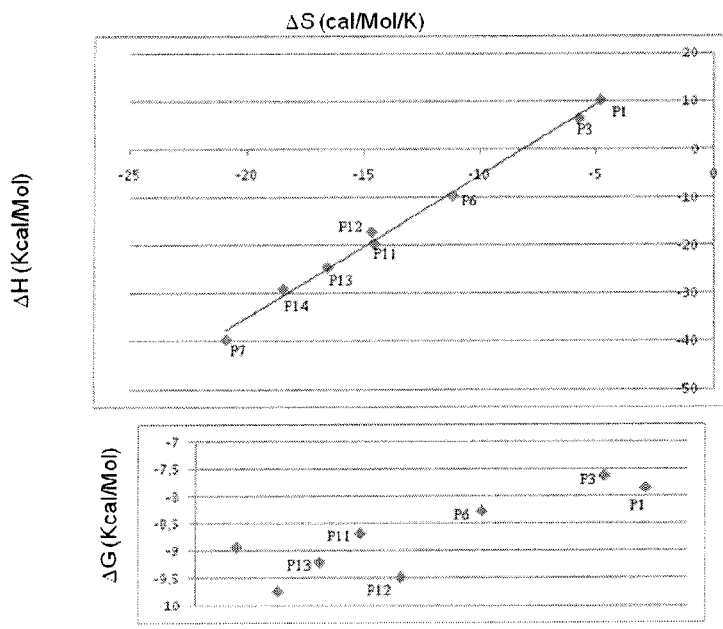

FIG. 8: Isothermal titration calorimetry (ITC).

A. Binding isotherms for the titration of the β ring with peptide P12 (SEQ ID No: 12) and P14 (SEQ ID No: 14). N: number of sites per β monomer.

B. Enthalpy-entropy compensation for selected natural and non-natural β binding peptides. The thermodynamics parameters are determined by ITC. Each value is the mean of two independent experiments monitoring the binding of each peptide (400 μM) to the β ring (20 or 30 μM) at 25° C. Each correlation point is labeled according to the corresponding peptide, and the respective ΔG values are plotted below. 1 cal=4.18J; (related to Table 11).

FIG. 9: Examples of compounds according to the invention are represented in FIG. 9 (A-H). Those include compounds wherein R=acetyl, cynamoyle, octanoyle; $R^1$=Cl and $R^2$=H, or $R^1$=$R^2$=Cl, or $R^1$=$R^2$=H, or $R^1$=Me and $R^2$=H, or $R^1$=Br and $R^2$=H; and $R^3$=OH or $NH_2$. Specific compounds P23 (SEQ ID No: 23), P24 (SEQ ID No: 24), P25 (SEQ ID No: 25), P26 (SEQ ID No: 26), P27 (SEQ ID No: 27), P28 (SEQ ID No: 28), P29 (SEQ ID No: 29) and P30 (SEQ ID No: 30) are disclosed in FIG. 9H.

EXAMPLES

Example 1

Structure-Based Design of Short Peptide Ligands Binding onto the E. coli Processivity Ring 1.1. Material and Methods 1.1.1. Protein Production, Purification and Characterization The E. coli dnaN gene was cloned into pET15b plasmid (Invitrogen) using standard protocols. The resulting N-tagged protein was expressed in BL21 E. coli cells after IPTG induction (0.1 mM) at 28° C. The β protein fraction was first enriched on a Ni-NTA column, eluted with an histidine step (300 mM) and further purified on a MonoQ column in buffer containing 20 mM Tris HCl pH 7.5, 0.5 mM EDTA and 10% glycerol, using a gradient from 0 to 0.5 M NaCl. The quality of the protein was assessed by mass spectrometry in denaturing and native conditions 1.1.2. Peptide Synthesis Peptides P1-P14 (SEQ ID Nos: 1 to 14) were synthesized in Fmoc chemistry by the stepwise solid-phase methodology[28] on a home-made semi-automatic peptide synthesizer[29]. N—N-Fmoc protected amino acids (natural and non natural) are commercially available from Polypeptide Labs (Strasbourg, France). Resins for solid-phase peptide synthesis are commercially available from Polypeptide Labs (Strasbourg, France) and CBL Patras (Patras, Greece). Assembly of the protected peptide chains was carried out on a 100-μmol scale starting from either Fmoc-Leu-Wang resin (Peptides P1, P2, P4), Fmoc-Phe-Wang (Peptides P3, P5-P10) resin or o-chlorotrityl chloride resin (peptide P11-P14). For each coupling step, the reactants were introduced manually as a solution in dry DMF (2.0 mL). Nα-Fmoc amino acids (5.0 equivalent) with standard side-chain protecting groups were coupled 2 times by using BOP (5.0 equivalent), HOBt (5.0 equivalent) and DIEA (10.0 equiv) in dry DMF for 20 min. The washing of the resin as well as Fmoc deprotection (by using a freshly prepared solution of 20% piperidine in DMF) were performed automatically. The coupling and deprotection steps were monitored by the Kaiser test[30]. At the end of the elongation of the peptidic chain, the resin was washed with $CH_2Cl_2$ and dried with $Et_2O$. A mixture of $TFA/H_2O/TIPS/DTT$ (8.8/0.5/0.2/0.5; 10.0 mL) was then added to the resin. The mixture was gently shaken for 2.5 h and the resulting solution was flushed through a frit in cold $Et_2O$. The precipitate was recovered by centrifugation, dissolved in a mixture of AcOH and $H_2O$ and freeze-dried. The crude peptides were finally purified by HPLC (linear gradient, 5-65% B, 30 min) and freeze-dried. All peptides were identified by matrix-assisted laser desorption/ionization mass spectrometry (MALDI-MS), and their homogeneity was assessed by $C_{18}$ RP-HPLC (purity of all peptides determined to be >90%).

Analytical data are reported in Table 8.

1.1.3. Molecular Dynamics

In the present work, the inventors used a protocol[31] based on the MM/PBSA method[32, 33], where conformations extracted from molecular dynamics simulations are processed using a simplified description for the solvent to yield an estimate of binding free energy. Individual contributions of each amino acid to the complex formation are estimated and important energetic amino acid "hot spots" are identified.

Structures

The initial structure for the apo protein was chain A from the PDB file 1OK7[17], while for the protein and native peptide it was chains B and C from the same PDB (1OK7). All crystallographic water molecules were retained.

MD Simulations

The CHARMM program[34], version 32, with the CHARMM 22 all atom protein-nucleic acid force field[35] was used for the molecular dynamics simulations. Hydrogen atoms were added using the HBUILD facility in the CHARMM program. A sphere of 37 Å containing 6840 water molecules (TIP3) was used to solvate the system. Stochastic boundary conditions were imposed and the calculation was limited to residues 7 Å around the peptide. The SHAKE algorithm was used to constrain hydrogen-heavy atom bond distances, and the simulations were done using Langevin algorithm. A 1-fs time step was used for the molecular dynamics simulation and the simulation time. A 12 Å cutoff was used; the van der Waals non bonded terms were treated with a SWITCH potential function whereas the electrostatic terms was evaluated with the SHIFT function.

Free Energy Decomposition of Interactions Between the $E.$ $coli$ β Clamp and the Different Peptides.

To obtain a semi-quantitative estimate of the contributions of all amino acids to the binding free energy for the formation of the β clamp-peptide complex, a molecular free energy decomposition scheme based on the Molecular Mechanics/Poisson-Boltzmann Surface Area (MM/PBSA) analysis was performed, following the approach presented by Lafont et al.[31]. From this analysis, an estimation of the free energy of binding for molecular complexes can be obtained. Briefly, in the MM/PBSA approach, the free energy is estimated using a standard thermodynamic cycle of the form

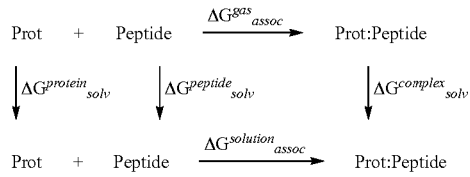

where the binding free energy is calculated according to the equation:

$$\Delta G_{assoc}^{solution} = \Delta E_{MM}^{gas} - T\Delta S_{MM} + \Delta G_{solvation}$$

where $\Delta_{MM}^{gas}$ is the difference in the gas phase energy; $\Delta S_{MM}$ is the change in entropy upon complex formation and $\Delta G_{solvation}$ is the change in solvation free energy. The gas phase energy differences contain terms for the intermolecular electrostatic and van der Waals energies, as well as the equivalent internal energy terms. These terms are based on the CHARMM force field in the present approach. The solvation free energy is divided into two contributions: an electrostatic and a nonpolar contribution. This latter term is approximated by an empirical relationship based on solvent accessible surface area and the electrostatic contribution is calculated here using the Poisson-Boltzmann equation.

Several approximations are introduced in the MM/PBSA method. The first was the neglect of conformational change upon complex formation, which is dictated by the absence of experimental structures for the unbound protein and peptides. To account for the unbound species in the calculations, their respective structures were obtained from the complex generated during the molecular dynamics simulations. With this approximation, there are no changes to the internal energy terms. The second approximation is the neglect of changes in configuration entropy due to binding. Although these simplifications preclude calculations of absolute values of the binding free energies, they have been shown in previous work to be satisfactory in the context of identifying interaction energy "hot spots" in protein-protein and protein-ligand complexes. Similar simplifications have been employed in other studies[36] [31] [37]. Via this approach, the total binding free energy can be decomposed into individual energetic contributions per residue. Decomposition of the binding free energy to individual amino acid contributions leads to the identification of amino acids that play a dominant role in binding and can contribute to reliable predictions of the role of particular amino acids in stabilizing complexes.

1.1.4. Structure-Based Design of Peptides

From the initial structural and energetic analysis of the RQLVLGL (SEQ ID No: 1, P1 in Table 1) peptide binding to the β clamp, modification of the sequence appeared potentially interesting in three positions (cf. FIG. 1): Q2; L3 and the hydrophobic L5-G6-L7 segment. In order to identify interesting modifications, the programs MCSS[38] and SEED[39] were used to dock small libraries of hydrophobic and polar small ligands (fragments) onto the surface of the β-clamp encompassing the peptide binding site. The protocol incorporated improved scoring functions with solvation corrections.[40, 41]. From this initial step, it appeared difficult to find replacements for the Q2 side-chain of the peptide that would correctly maintain the intricate hydrogen-bond network at this position (see FIG. 3) and therefore no modification of Q2 were attempted. For the other positions, improving interactions with optimized hydrophobic contacts appeared promising. Based on these initial data, a selection of peptides with modified side chains were constructed, docked into the structure and their interactions with the β clamp evaluated using the MM-PBSA protocol described above. The choice of side-chain replacements was based on the docking data, focusing on commercially available protected amino-acids. A force field adapted from CHARMM 22[35] was used for non-natural amino acids. The most promising candidates were selected for synthesis.

1.1.5. β/Peptide Interaction in Solution: In Vitro Competition Assays.

5' end radiolabelling, purification and annealing of synthetic primers were performed as previously described (Wagner et al., 1999). The 30/90mer synthetic construct was obtained by annealing the 30 mer primer (5'GTAAAAC-GACGGCCAGTGCCAAGCTTAGTC3', SEQ ID No: 34) with the 90 mer template (5 'CCATGATTACGAATTCAGT-CATCACCGGCGCCACAGACTAAGCTTGGCACTG GCCGTCGTTTTACAACGTCGTGACTGGGAAAA CCCTGG3', SEQ ID No:35) to form a double stranded structure with 5' and 3' ssDNA overhangs of 25 and 35 nucleotides, respectively. All replication experiments (10 µl final volume) were carried out in buffer E (40 mM HEPES pH 7.5, 80 mM potassium glutamate, 160 µg/ml BSA, 16% glycerol, 0.016% NP40, 8 mM DTT). The 30/90 mer duplex (1 nM final concentration) was first incubated with single strand binding protein (SSB; Sigma; 90 nM final concentration) in the presence of ATP (200 µM) and MgCl₂ (7.5 mM) at 37° C. for 10 min. γ complex (1 nM final concentration) (obtained as described by Dallmann et al, 1995) and β clamp (5 nM as dimer final concentration) were added at that stage and incubation was carried out at 37° C. for 10 min. Then, 7 µl of the mixture was added to 1 µl of either DMSO or 1 µl of peptide solution (as specified), incubated 5 min. at room temperature and further 2 hours at 4° C. 1 µl of PolIV was then added (1.5 nM final concentration), incubated 5 min. at room temperature and finally, the whole reaction was mixed with 1 µl of a dNTPs solution (200 µM each dNTP final concentration) and let react for 1 min. at room temperature. Reactions were quenched by the addition of 20 µl of 95% formamide/dyes solution containing 7.5 mM EDTA, heat-denatured and analysed by chromatography on 12% denaturing polyacrylamide gels. Radiolabelled products were visualised and quantified using a Personal Molecular Imager Fx and the Quantity One software (Bio-Rad).

1.1.6. SPR Assays.

SPR experiments were performed on a Biacore® 3000. The association constant ($K_A$) of β with the natural Cter heptamer (P1, Table 7) of the DNA polymerase IV of *E. coli* were determined as follow: the β protein (0.125 µM to 2 µM) was injected on the immobilized P1 peptide at a flow rate of 500 µL·min$^{-1}$. After subtraction of the background response, the data were fit to the 1:1 Langmuir model using BIAevaluation (Biacore™). The inhibition of P1-β interaction by peptides P2 to P14 (Table 7) was used to measure their affinity for β and was assessed according to the following procedure: complexes of β ring (0.25 µM) with various concentrations of challenging peptides (1.5 nM to 100 µM) were formed and injected on a chip loaded with the P1 peptide. IC$_{50}$ values for each challenging peptide were determined by plotting the concentration of peptide against the percentage of binding inhibition. The IC$_{50}$ value of each peptide was used to calculate Ki (Ki=(1+K$_A$[β])/IC$_{50}$) which measures the affinity of the challenging peptide for β in the competition assay, and ΔG was derived from Ki (ΔG=RT ln Ki).

1.1.7. Isothermal Titration Calorimetry.

ITC was performed by using a ITC200 microcalorimeter from MicroCal. Peptides (400 µM) were titrated in sequential injections (2 µl each) into a β ring solution (300 µl, 20 or 30 µM) at 25° C. Data were corrected from control experiments where peptides were injected in buffer solution (Hepes 10 mM pH 7.4, NaCl 0.15M, EDTA 3 mM, P20 0.005%). Data analysis was performed with Origin 7.0 software.

1.1.8. Crystallogenesis, Data Collection and Processing.

Crystallization experiments were essentially conducted as described previously[17]. Crystals of P12-β complexes were grown in capillaries in presence of 0.2% of agarose[42]. Crystallisation buffer contained 100 mM CaCl$_2$, 100 mM Mes pH 6.0 and 30% PEG 400. Cryoprotection was performed by soaking crystals in the same buffer supplemented with 20% glycerol. Cryoprotected crystals were frozen in liquid ethane and X-ray diffraction data were collected at 100 K at beamline X06SA at the Swiss Light Source (Villigen PSI, Switzerland) and beamlines ID29 and ID14-4 at ESRF (Grenoble, France). Diffraction images were processed with XDS, XSCALE and XDSCONV[43]. The structures were solved by molecular replacement with MOLREP[44], using the known beta structure as a search model PDB ID 1OK7[12]. Alternate rounds of rebuilding and refinement, including noncrystallographic symmetry restraints, were carried out with PHENIX[45], COOT[46] and CNS[47]. Model statistics were obtained with Molprobity[48]. Molecular visualizations and structures illustrations were performed using PyMOL[49]. Data processing and refinement statistics are summarized in Table 11.

1.2. Results 1.2.1. Structure and Energetics of the Binding Pocket

The inventors have previously solved the structure of a complex formed between the *E. coli* β clamp and the 16 residues long C-terminal peptide of the *E. coli* DNA polymerase IV (PDB code: 1OK7)[17]. A first part of the present work aimed at unraveling the molecular basis of the peptide-pocket interactions. Molecular modeling approaches were used to determine the contribution of each residue of the last seven amino-acids of the C-terminal part of Pol IV ($R_1Q_2L_3V_4L_5G_6L_7$, SEQ ID No: 32) to the overall interaction (FIG. 2A), using free energy decomposition (see Material and Methods). For each amino acid, the van der Waals, electrostatic and hydrophobic solvation contribution to binding have been calculated. Stabilizing interactions between the β ring and the peptide are essentially Van der Waals contacts (see FIG. 2A). Electrostatics contributions are poor, due to compensation between the protein-peptide interaction and the peptide desolvation cost. Hydrophobic solvation contributions are favorable but of lesser magnitude. The net contributions of residues $Q_2$, $L_3$, $L_5$ and $L_7$ is predominant to the overall interaction (FIG. 2B). $G_6$ has no contribution while $V_4$ which is oriented toward the solvent poorly contributes to the interaction.

Due to the good resolution, the inventors could also analyze the position of water molecules in the free and bound pockets of the 1OK7 structure. In the absence of peptide, four water molecules are located in subsite 1. Upon peptide binding, one is eliminated and one is repositioned close to the $T_{142}$ and $Y_{154}$ residues, allowing the $L_5$-$G_6$-$L_7$ tripeptide to bind into the hydrophobic subsite 1 (FIG. 1AB). The two water molecules located on the platform in the apo monomer are dislodged upon peptide binding, thus making room for the peptide $L_3$ residue to bind (FIG. 1BC). Finally, two water molecules are deeply inserted into the empty subsite 2. One of these two molecules interconnects the $N_\alpha H$ of $N_{320}$ and the $C_\alpha=O$ of $M_{362}$ (FIG. 3) and is not exchanged with the solvent upon peptide binding, underlining its structural function. The second water molecule is replaced by the Cδ=O of peptide Q2 residue, while its δ-amino group establishes bounds with the Cα=O of $M_{362}$ and the Cα=O of peptide residue $L_2$ (FIG. 3B).

This initial analysis led the inventors to design a minimal peptide binding sequence that was used as a starting point for ligand optimization. Because of the complex network of hydrogen bonds formed by the highly conserved Q residue in subsite 2, one cannot substitute this side chain without dramatically altering the interaction of the whole peptide. Alternatively, several other positions in the peptide sequence may accept modifications that could increase its affinity for the β clamp. Following the structural and energetic analysis of the binding pocket (see Material and Methods), several peptides were synthesized (Table 7 and Table 11) and their binding efficiencies were analyzed by surface plasmon resonance (SPR). The dissociation constant of the P1 natural heptapeptide was measured to be 2.85 (±0.94) 10$^{-7}$ M. As compared to the whole polymerase, this peptide binds 30 fold less efficiently to the ring (table 1, compare P1 and PolIV), pinpointing the contribution of alternate regions of the enzyme to the interaction[16, 14, 19]. Removing the G residue of the terminal tripeptide (-LGL) results in a two to three fold decrease in interaction (table 1, compare P1 and P2), while replacing the terminal tripeptide with the consensus LF dipeptide does not affect the affinity (table 1, compare P1 and P3). However, a FL dipeptide totally disrupts peptide binding (table 1, P4). Substituting F for other aromatic residues (W,Y) at the C-terminal position does not contribute to any increased interaction (data not shown). In order to design the shortest peptide, the first ($R_1$) residue was also removed, which does not seem to contribute significantly to the binding (table 1, P5, FIGS. 1 and 2)[17], and the $V_4$ was replaced by a D residue, as observed in the consensus sequence, in order to increase the solubility of the resulting pentapeptide P5 (QLDLF). Although its affinity for the β ring is low, it was increased by 10 fold upon acetylation (table 1, compare P5 and P6), thus providing a good compromise between interaction efficiency and ligand size.

TABLE 1

Influence of the C-terminal tripeptide sequence and effect of N-terminal acetylation on the interaction of peptide with the E. coli β clamp, as measured by SPR experiments.

| # | sequence | $IC_{50}$ (µM) | Ki ($10^6$ $M^{-1}$) | ΔG (Kcal/mol) | Seq Id No: |
|---|---|---|---|---|---|
| PolIV | | 0.29 | 4.7 | −9.09 | |
| P1 | RQLVLGL | 8.85 | 0.15 | −7.06 | 1 |
| P2 | RQLVLL | 21.53 | 0.0063 | −6.54 | 2 |
| P3 | RQLVLF | 8.62 | 0.15 | −7.04 | 3 |
| P4 | RQLVFL | 256 | ∅ | ∅ | 4 |
| P5 | QLDLF | 12.44 | 0.11 | −6.87 | 5 |
| P6 | AcQLDLF | 1.12 | 1.2 | −8.22 | 6 |

∅: not determined.
Ki = (1 + $K_4$[β])/$IC_{50}$.
ΔG = -RT ln Ki.
PolIV: E coli DNA polymerase IV.

1.2.2. Crystal Structure of the P6-β Ring Complex.

The P6 peptide (AcQLDLF, SEQ ID No: 6) co-crystallized with the β ring in conditions similar to those previously described[17] but the cell parameters lead to a $V_M$ value of 7.8, which corresponds to the presence of 3 dimers per asymmetric unit (Table 2). This structure was solved by molecular replacement at 2.3 Å resolution, using our previously determined structure (PDB 1OK7). The superposition of main chain atoms of each ring to the model led to rmsd values ranging from 0.70 Å to 1.06 Å, underlining the close structural similarity of each dimer. Each monomer of the three rings binds a peptide, and all ligands adopt a similar conformation in all six hydrophobic pockets, as indicated by a rmsd value ranging between 0.25 Å to 0.51 Å.

TABLE 2

Statistics on Data Collection and Refinement (related to FIG. 5).

| Structure | Beta-P14 (PDB 3Q4L) | Beta-P6 (PDB 3Q4J) | Beta-P12 (PDB 3Q4K) |
|---|---|---|---|
| Data Collection | | | |
| Space Group | P1 | P1 | P1 |
| Unit cell a (Å) | 34.84 | 35.09 | 36.25 |
| b (Å) | 79.57 | 132.87 | 80 |
| c (Å) | 81.64 | 137.27 | 82.18 |
| α (°) | 65.28 | 62.73 | 66.15 |
| β (°) | 75.26 | 88.51 | 74.94 |
| γ (°) | 82.22 | 89.77 | 82.03 |
| Beamline | ID29/ESRF | X06SA/SLS | ID14-4/ESRF |
| Wavelength (Å) | 0.97623 | 0.915694 | 0.9794 |
| Resolution limits (Å) | 39.2-1.95 | 29.5-2.3 | 19.9-2.6 |
| high resolution shell | 2.0-1.95 | 2.35-2.3 | 2.65-2.6 |
| Reflections: | | | |
| measured | 221062 | 296785 | 42708 |
| unique | 54138 | 96508 | 22982 |
| Completeness (%) | 96.3 (93.8)* | 98.6 (97.9)* | 91.9 (60.5)* |
| $R_{merge}$ | 0.06 (0.72)* | 0.05 (0.36)* | 0.067 (0.11)* |
| I/σ | 13 (1.9)* | 22.6 (3.6)* | 8.7 (4.0)* |
| Refinement | | | |
| Reflections $R_{cryst}/R_{free}$ | 54134/2750 | 96493/7742 | 22979/1160 |
| $R_{cryst}$ (%) | 20.1 | 21.6 | 25.9 |
| $R_{free}$ (%)† | 23.2 | 25.0 | 30.6 |
| Protein atoms | 5579 | 17085 | 5471 |
| Ligand atoms | 106 | 196 | 103 |
| Water molecules | 299 | 357 | 129 |
| Average B factor (Å²) | | | |
| Protein | 33.3 | 52.1 | 30.4 |
| Ligand | 39.4 | 66.5 | 27.1 |
| Water | 40.1 | 44.5 | 27.6 |
| R.m.s.d. bond length (Å) | 0.01 | 0.009 | 0.008 |
| R.m.s.d. angles length (°) | 1.13 | 1.15 | 1.11 |

*Values in parentheses correspond to high resolution shell in data collections.
†5% of the reflections were set aside for an Rfree test before initiating any refinement The atomic coordinates of the peptide and the peptide binding site of the β clamp (residues ≤5 Å from the ligand) are disclosed in the following Table 3. The other residues have the same positions as in the previously determined structure (PDB 1OK7) also described in U.S. Pat. No. 7,635,583.

TABLE 3

Atomic coordinates of P6 residues and of the residues involved in the binding of P6 to the β clamp, in the crystal of P6 peptide co-crystallized with the β ring.

| | | | | | | | | | | |
|---|---|---|---|---|---|---|---|---|---|---|
| ATOM | 1 | NE | ARG | B | 152 | 10.195 | −25.903 | 12.978 | 1.00 | 60.02 N |
| ATOM | 2 | CZ | ARG | B | 152 | 9.832 | −25.010 | 13.891 | 1.00 | 70.75 C |
| ATOM | 3 | NH1 | ARG | B | 152 | 10.045 | −23.710 | 13.686 | 1.00 | 51.13 N1+ |
| ATOM | 4 | NH2 | ARG | B | 152 | 9.228 | −25.402 | 15.004 | 1.00 | 66.21 N |
| TER | 5 | | ARG | B | 152 | | | | | |
| ATOM | 6 | CG | LEU | B | 155 | 6.034 | −25.353 | 10.551 | 1.00 | 37.71 C |
| ATOM | 7 | CD1 | LEU | B | 155 | 6.887 | −24.861 | 11.676 | 1.00 | 37.67 C |
| ATOM | 8 | CD2 | LEU | B | 155 | 4.805 | −25.976 | 11.115 | 1.00 | 31.46 C |
| TER | 9 | | LEU | B | 155 | | | | | |
| ATOM | 10 | CB | THR | B | 172 | 1.710 | −23.748 | 14.242 | 1.00 | 31.63 C |
| ATOM | 11 | CG2 | THR | B | 172 | 2.028 | −25.084 | 13.527 | 1.00 | 27.98 C |
| ATOM | 12 | OG1 | THR | B | 172 | 2.665 | −23.450 | 15.241 | 1.00 | 32.30 O |
| ATOM | 13 | C | ASP | B | 173 | 6.157 | −21.665 | 14.133 | 1.00 | 35.44 C |
| ATOM | 14 | N | GLY | B | 174 | 5.672 | −22.551 | 14.996 | 1.00 | 34.81 N |
| ATOM | 15 | CA | GLY | B | 174 | 6.511 | −23.182 | 16.011 | 1.00 | 35.62 C |
| ATOM | 16 | C | GLY | B | 174 | 6.492 | −22.492 | 17.359 | 1.00 | 39.39 C |
| ATOM | 17 | O | GLY | B | 174 | 6.970 | −23.064 | 18.344 | 1.00 | 39.92 O |
| ATOM | 18 | N | HIS | B | 175 | 5.986 | −21.242 | 17.411 | 1.00 | 34.18 N |
| ATOM | 19 | CA | HIS | B | 175 | 5.900 | −20.479 | 18.650 | 1.00 | 33.72 C |
| ATOM | 20 | C | HIS | B | 175 | 4.476 | −20.329 | 19.088 | 1.00 | 35.43 C |
| ATOM | 21 | O | HIS | B | 175 | 4.175 | −20.368 | 20.282 | 1.00 | 34.79 O |
| ATOM | 22 | CB | HIS | B | 175 | 6.562 | −19.119 | 18.513 | 1.00 | 36.12 C |

TABLE 3-continued

Atomic coordinates of P6 residues and of the residues involved in the binding of P6 to the β clamp, in the crystal of P6 peptide co-crystallized with the β ring.

| ATOM | 23 | CG | HIS | B | 175 | 7.984 | −19.194 | 18.096 | 1.00 | 41.64 | C |
|---|---|---|---|---|---|---|---|---|---|---|---|
| ATOM | 24 | CD2 | HIS | B | 175 | 9.032 | −19.835 | 18.668 | 1.00 | 44.85 | C |
| ATOM | 25 | ND1 | HIS | B | 175 | 8.394 | −18.617 | 16.936 | 1.00 | 45.18 | N |
| ATOM | 26 | CE1 | HIS | B | 175 | 9.678 | −18.899 | 16.829 | 1.00 | 45.14 | C |
| ATOM | 27 | NE2 | HIS | B | 175 | 10.115 | −19.589 | 17.878 | 1.00 | 45.20 | N |
| ATOM | 28 | N | ARG | B | 176 | 3.593 | −20.133 | 18.121 | 1.00 | 31.08 | N |
| ATOM | 29 | CA | ARG | B | 176 | 2.181 | −19.986 | 18.371 | 1.00 | 29.68 | C |
| ATOM | 30 | C | ARG | B | 176 | 1.413 | −20.789 | 17.353 | 1.00 | 32.45 | C |
| ATOM | 31 | O | ARG | B | 176 | 1.918 | −21.053 | 16.262 | 1.00 | 32.86 | O |
| ATOM | 32 | N | LEU | B | 177 | 0.240 | −21.239 | 17.733 | 1.00 | 27.89 | N |
| ATOM | 33 | CA | LEU | B | 177 | −0.619 | −22.029 | 16.875 | 1.00 | 27.83 | C |
| ATOM | 34 | CB | LEU | B | 177 | −0.579 | −23.523 | 17.307 | 1.00 | 27.38 | C |
| ATOM | 35 | CG | LEU | B | 177 | −1.466 | −24.512 | 16.510 | 1.00 | 31.18 | C |
| ATOM | 36 | CD1 | LEU | B | 177 | −0.745 | −25.845 | 16.280 | 1.00 | 30.87 | C |
| TER | 37 | | LEU | B | 177 | | | | | | |
| ATOM | 38 | CB | PRO | B | 242 | 3.262 | −29.933 | 14.003 | 1.00 | 42.35 | C |
| ATOM | 39 | CG | PRO | B | 242 | 3.185 | −28.774 | 13.112 | 1.00 | 45.82 | C |
| ATOM | 40 | CD | PRO | B | 242 | 3.325 | −29.320 | 11.745 | 1.00 | 40.86 | C |
| TER | 41 | | PRO | B | 242 | | | | | | |
| ATOM | 42 | O | VAL | B | 247 | −0.058 | −27.602 | 22.929 | 1.00 | 52.04 | O |
| ATOM | 43 | CB | VAL | B | 247 | 0.470 | −28.149 | 19.728 | 1.00 | 50.73 | C |
| ATOM | 44 | CG1 | VAL | B | 247 | 0.574 | −26.655 | 20.015 | 1.00 | 50.50 | C |
| ATOM | 45 | CG2 | VAL | B | 247 | 1.641 | −28.626 | 18.875 | 1.00 | 51.23 | C |
| TER | 46 | | VAL | B | 247 | | | | | | |
| ATOM | 47 | O | GLY | B | 318 | 5.474 | −15.393 | 28.086 | 1.00 | 28.75 | O |
| ATOM | 48 | N | PHE | B | 319 | 5.344 | −13.225 | 27.583 | 1.00 | 24.23 | N |
| ATOM | 49 | CA | PHE | B | 319 | 4.851 | −13.489 | 26.241 | 1.00 | 24.99 | C |
| ATOM | 50 | C | PHE | B | 319 | 5.356 | −12.468 | 25.290 | 1.00 | 30.49 | C |
| ATOM | 51 | O | PHE | B | 319 | 5.591 | −11.324 | 25.669 | 1.00 | 32.74 | O |
| ATOM | 52 | CB | PHE | B | 319 | 3.310 | −13.478 | 26.174 | 1.00 | 27.25 | C |
| ATOM | 53 | CG | PHE | B | 319 | 2.640 | −14.732 | 26.670 | 1.00 | 28.63 | C |
| ATOM | 54 | CD1 | PHE | B | 319 | 2.741 | −15.919 | 25.957 | 1.00 | 30.47 | C |
| ATOM | 55 | CE1 | PHE | B | 319 | 2.128 | −17.094 | 26.424 | 1.00 | 31.60 | C |
| ATOM | 56 | N | ASN | B | 320 | 5.468 | −12.865 | 24.025 | 1.00 | 26.27 | N |
| ATOM | 57 | CA | ASN | B | 320 | 5.720 | −11.953 | 22.949 | 1.00 | 26.75 | C |
| ATOM | 58 | C | ASN | B | 320 | 4.315 | −11.306 | 22.760 | 1.00 | 28.81 | C |
| ATOM | 59 | O | ASN | B | 320 | 3.351 | −11.990 | 22.409 | 1.00 | 25.74 | O |
| ATOM | 60 | CB | ASN | B | 320 | 6.143 | −12.740 | 21.690 | 1.00 | 31.09 | C |
| ATOM | 61 | CG | ASN | B | 320 | 6.252 | −11.902 | 20.458 | 1.00 | 38.50 | C |
| ATOM | 62 | ND2 | ASN | B | 320 | 7.226 | −12.202 | 19.631 | 1.00 | 36.32 | N |
| TER | 63 | | ASN | B | 320 | | | | | | |
| ATOM | 64 | CB | TYR | B | 323 | 2.398 | −14.188 | 20.062 | 1.00 | 29.74 | C |
| ATOM | 65 | CG | TYR | B | 323 | 3.671 | −14.541 | 19.312 | 1.00 | 34.89 | C |
| ATOM | 66 | CD2 | TYR | B | 323 | 4.613 | −15.405 | 19.867 | 1.00 | 36.98 | C |
| ATOM | 67 | CE2 | TYR | B | 323 | 5.769 | −15.758 | 19.176 | 1.00 | 38.52 | C |
| ATOM | 68 | CZ | TYR | B | 323 | 5.978 | −15.280 | 17.899 | 1.00 | 45.00 | C |
| ATOM | 69 | OH | TYR | B | 323 | 7.102 | −15.660 | 17.220 | 1.00 | 51.04 | O |
| TER | 70 | | TYR | B | 323 | | | | | | |
| ATOM | 71 | O | SER | B | 343 | 6.499 | −19.652 | 31.418 | 1.00 | 42.19 | O |
| ATOM | 72 | CA | VAL | B | 344 | 7.142 | −22.358 | 31.029 | 1.00 | 30.95 | C |
| ATOM | 73 | C | VAL | B | 344 | 6.382 | −23.225 | 30.039 | 1.00 | 37.16 | C |
| ATOM | 74 | O | VAL | B | 344 | 6.960 | −23.833 | 29.135 | 1.00 | 38.77 | O |
| ATOM | 75 | CB | VAL | B | 344 | 8.406 | −23.037 | 31.630 | 1.00 | 34.02 | C |
| ATOM | 76 | CG1 | VAL | B | 344 | 9.318 | −22.002 | 32.284 | 1.00 | 33.14 | C |
| TER | 77 | | VAL | B | 344 | | | | | | |
| ATOM | 78 | CB | SER | B | 346 | 1.690 | −23.500 | 25.230 | 1.00 | 34.25 | C |
| ATOM | 79 | OG | SER | B | 346 | 0.915 | −24.661 | 25.493 | 1.00 | 39.01 | O |
| TER | 80 | | SER | B | 346 | | | | | | |
| ATOM | 81 | C | VAL | B | 360 | −0.613 | −20.918 | 21.452 | 1.00 | 27.37 | C |
| ATOM | 82 | O | VAL | B | 360 | −0.111 | −20.800 | 20.340 | 1.00 | 24.84 | O |
| ATOM | 83 | CB | VAL | B | 360 | −1.624 | −23.300 | 21.499 | 1.00 | 27.65 | C |
| ATOM | 84 | CG1 | VAL | B | 360 | −0.575 | −23.807 | 22.494 | 1.00 | 27.63 | C |
| ATOM | 85 | C | VAL | B | 361 | 1.982 | −19.886 | 23.474 | 1.00 | 27.90 | C |
| ATOM | 86 | CG1 | VAL | B | 361 | 1.873 | −16.988 | 22.556 | 1.00 | 22.99 | C |
| ATOM | 87 | N | MET | B | 362 | 3.180 | −20.112 | 23.023 | 1.00 | 28.61 | N |
| ATOM | 88 | CA | MET | B | 362 | 4.274 | −20.561 | 23.871 | 1.00 | 28.56 | C |
| ATOM | 89 | C | MET | B | 362 | 4.839 | −19.321 | 24.530 | 1.00 | 31.58 | C |
| ATOM | 90 | O | MET | B | 362 | 5.039 | −18.292 | 23.870 | 1.00 | 29.49 | O |
| ATOM | 91 | CB | MET | B | 362 | 5.340 | −21.302 | 23.049 | 1.00 | 31.41 | C |
| ATOM | 92 | CG | MET | B | 362 | 6.222 | −22.193 | 23.888 | 1.00 | 35.60 | C |
| ATOM | 93 | SD | MET | B | 362 | 5.377 | −23.603 | 24.664 | 1.00 | 38.96 | S |
| ATOM | 94 | CE | MET | B | 362 | 6.619 | −24.060 | 25.847 | 1.00 | 34.70 | C |
| ATOM | 95 | N | PRO | B | 363 | 5.071 | −19.362 | 25.842 | 1.00 | 29.24 | N |
| ATOM | 96 | CA | PRO | B | 363 | 5.609 | −18.178 | 26.510 | 1.00 | 28.99 | C |
| ATOM | 97 | C | PRO | B | 363 | 7.074 | −17.892 | 26.226 | 1.00 | 33.83 | C |
| ATOM | 98 | O | PRO | B | 363 | 7.743 | −18.614 | 25.456 | 1.00 | 33.34 | O |
| ATOM | 99 | CB | PRO | B | 363 | 5.341 | −18.479 | 27.991 | 1.00 | 30.94 | C |

TABLE 3-continued

Atomic coordinates of P6 residues and of the residues involved in the binding of P6 to the β clamp, in the crystal of P6 peptide co-crystallized with the β ring.

| | | | | | | | | | | |
|---|---|---|---|---|---|---|---|---|---|---|
| ATOM | 100 | CG | PRO | B | 363 | 5.412 | −19.947 | 28.091 | 1.00 | 35.37 C |
| ATOM | 101 | CD | PRO | B | 363 | 4.870 | −20.473 | 26.798 | 1.00 | 31.25 C |
| ATOM | 102 | N | MET | B | 364 | 7.545 | −16.777 | 26.784 | 1.00 | 29.71 N |
| ATOM | 103 | CA | MET | B | 364 | 8.945 | −16.382 | 26.731 | 1.00 | 30.02 C |
| ATOM | 104 | C | MET | B | 364 | 9.502 | −16.624 | 28.124 | 1.00 | 40.88 C |
| ATOM | 105 | O | MET | B | 364 | 8.772 | −16.499 | 29.120 | 1.00 | 40.62 O |
| ATOM | 106 | CB | MET | B | 364 | 9.118 | −14.915 | 26.403 | 1.00 | 30.48 C |
| ATOM | 107 | CG | MET | B | 364 | 8.757 | −14.585 | 25.034 | 1.00 | 32.54 C |
| ATOM | 108 | SD | MET | B | 364 | 8.724 | −12.808 | 24.682 | 1.00 | 35.07 s |
| ATOM | 109 | CE | MET | B | 364 | 10.528 | −12.292 | 24.937 | 1.00 | 31.33 C |
| ATOM | 110 | N | ARG | B | 365 | 10.767 | −17.037 | 28.190 | 1.00 | 42.29 N |
| ATOM | 111 | CA | ARG | B | 365 | 11.463 | −17.315 | 29.447 | 1.00 | 44.24 C |
| ATOM | 112 | C | ARG | B | 365 | 11.620 | −15.996 | 30.209 | 1.00 | 47.68 C |
| ATOM | 113 | O | ARG | B | 365 | 12.039 | −14.991 | 29.621 | 1.00 | 46.53 O |
| ATOM | 114 | CB | ARG | B | 365 | 12.812 | −18.035 | 29.173 | 1.00 | 49.79 C |
| ATOM | 115 | CG | ARG | B | 365 | 13.354 | −18.871 | 30.335 | 1.00 | 61.58 C |
| ATOM | 116 | CD | ARG | B | 365 | 12.589 | −20.152 | 30.620 | 1.00 | 75.54 C |
| ATOM | 117 | NE | ARG | B | 365 | 13.073 | −21.279 | 29.817 | 1.00 | 90.27 N |
| ATOM | 118 | CZ | ARG | B | 365 | 12.957 | −22.563 | 30.161 | 1.00 | 100.27 C |
| ATOM | 119 | NH1 | ARG | B | 365 | 13.409 | −23.516 | 29.355 | 1.00 | 79.16 N1+ |
| ATOM | 120 | NH2 | ARG | B | 365 | 12.398 | −22.901 | 31.318 | 1.00 | 86.12 N |
| TER | 121 | | ARG | B | 365 | | | | | |
| HETATM | 122 | O | HOH | B | 384 | 8.833 | −14.385 | 20.130 | 1.00 | 33.25 O |
| HETATM | 123 | O | HOH | B | 407 | 10.652 | −12.727 | 21.066 | 1.00 | 31.86 O |
| HETATM | 124 | O | HOH | B | 465 | 12.648 | −14.060 | 22.219 | 1.00 | 36.65 O |
| HETATM | 125 | O | HOH | B | 466 | 13.941 | −12.371 | 23.870 | 1.00 | 26.96 O |
| HETATM | 126 | C | ACE | H | 69 | 12.190 | −16.728 | 25.287 | 1.00 | 47.99 C |
| HETATM | 127 | O | ACE | H | 69 | 11.809 | −17.683 | 25.955 | 1.00 | 46.88 O |
| HETATM | 128 | CH3 | ACE | H | 69 | 13.141 | −15.743 | 25.924 | 1.00 | 48.05 C |
| ATOM | 129 | N | GLN | H | 70 | 11.778 | −16.484 | 24.012 | 1.00 | 43.64 N |
| ATOM | 130 | CA | GLN | H | 70 | 10.826 | −17.283 | 23.246 | 1.00 | 42.45 C |
| ATOM | 131 | C | GLN | H | 70 | 11.026 | −18.818 | 23.243 | 1.00 | 48.79 C |
| ATOM | 132 | O | GLN | H | 70 | 11.987 | −19.340 | 22.644 | 1.00 | 49.83 O |
| ATOM | 133 | CB | GLN | H | 70 | 10.668 | −16.743 | 21.816 | 1.00 | 43.26 C |
| ATOM | 134 | CG | GLN | H | 70 | 9.503 | −17.399 | 21.019 | 1.00 | 48.43 C |
| ATOM | 135 | CD | GLN | H | 70 | 8.133 | −17.259 | 21.688 | 1.00 | 51.59 C |
| ATOM | 136 | NE2 | GLN | H | 70 | 7.769 | −16.030 | 22.096 | 1.00 | 32.22 N |
| ATOM | 137 | OE1 | GLN | H | 70 | 7.418 | −18.250 | 21.901 | 1.00 | 38.15 O |
| ATOM | 138 | N | LEU | H | 71 | 10.077 | −19.531 | 23.889 | 1.00 | 44.09 N |
| ATOM | 139 | CA | LEU | H | 71 | 10.074 | −20.993 | 23.930 | 1.00 | 42.82 C |
| ATOM | 140 | C | LEU | H | 71 | 9.337 | −21.541 | 22.690 | 1.00 | 47.21 C |
| ATOM | 141 | O | LEU | H | 71 | 8.603 | −20.812 | 22.008 | 1.00 | 46.65 O |
| ATOM | 142 | CB | LEU | H | 71 | 9.507 | −21.552 | 25.254 | 1.00 | 42.99 C |
| ATOM | 143 | CG | LEU | H | 71 | 10.264 | −21.176 | 26.550 | 1.00 | 48.52 C |
| ATOM | 144 | CD1 | LEU | H | 71 | 9.369 | −21.316 | 27.773 | 1.00 | 48.02 C |
| ATOM | 145 | CD2 | LEU | H | 71 | 11.512 | −22.045 | 26.736 | 1.00 | 53.09 C |
| ATOM | 146 | N | ASP | H | 72 | 9.557 | −22.813 | 22.379 | 1.00 | 45.35 N |
| ATOM | 147 | CA | ASP | H | 72 | 8.966 | −23.458 | 21.213 | 1.00 | 45.33 C |
| ATOM | 148 | C | ASP | H | 72 | 7.805 | −24.369 | 21.558 | 1.00 | 46.72 C |
| ATOM | 149 | O | ASP | H | 72 | 7.847 | −25.031 | 22.589 | 1.00 | 44.98 O |
| ATOM | 150 | CB | ASP | H | 72 | 10.057 | −24.179 | 20.397 | 1.00 | 47.71 C |
| ATOM | 151 | CG | ASP | H | 72 | 10.805 | −23.219 | 19.472 | 1.00 | 73.93 C |
| ATOM | 152 | OD1 | ASP | H | 72 | 11.558 | −22.358 | 19.986 | 1.00 | 75.90 O |
| ATOM | 153 | OD2 | ASP | H | 72 | 10.576 | −23.278 | 18.231 | 1.00 | 87.47 O1− |
| ATOM | 154 | N | LEU | H | 73 | 6.766 | −24.394 | 20.694 | 1.00 | 44.17 N |
| ATOM | 155 | CA | LEU | H | 73 | 5.598 | −25.260 | 20.839 | 1.00 | 44.82 C |
| ATOM | 156 | C | LEU | H | 73 | 5.949 | −26.725 | 20.585 | 1.00 | 49.95 C |
| ATOM | 157 | O | LEU | H | 73 | 5.343 | −27.628 | 21.189 | 1.00 | 49.17 O |
| ATOM | 158 | CB | LEU | H | 73 | 4.487 | −24.829 | 19.868 | 1.00 | 44.08 C |
| ATOM | 159 | CG | LEU | H | 73 | 3.484 | −23.817 | 20.345 | 1.00 | 45.47 C |
| ATOM | 160 | CD1 | LEU | H | 73 | 2.433 | −23.649 | 19.295 | 1.00 | 45.34 C |
| ATOM | 161 | CD2 | LEU | H | 73 | 2.807 | −24.251 | 21.651 | 1.00 | 38.54 C |
| ATOM | 162 | N | PHE | H | 74 | 6.897 | −26.941 | 19.644 | 1.00 | 47.70 N |
| ATOM | 163 | CA | PHE | H | 74 | 7.378 | −28.265 | 19.211 | 1.00 | 48.65 C |
| ATOM | 164 | C | PHE | H | 74 | 8.752 | −28.089 | 18.510 | 1.00 | 75.49 C |
| ATOM | 165 | O | PHE | H | 74 | 9.100 | −26.937 | 18.126 | 1.00 | 77.08 O |
| ATOM | 166 | CB | PHE | H | 74 | 6.340 | −28.932 | 18.271 | 1.00 | 49.99 C |
| ATOM | 167 | CG | PHE | H | 74 | 5.819 | −28.030 | 17.171 | 1.00 | 50.87 C |
| ATOM | 168 | CD1 | PHE | H | 74 | 6.502 | −27.909 | 15.963 | 1.00 | 52.73 C |
| ATOM | 169 | CD2 | PHE | H | 74 | 4.661 | −27.281 | 17.352 | 1.00 | 52.30 C |
| ATOM | 170 | CE1 | PHE | H | 74 | 6.047 | −27.044 | 14.972 | 1.00 | 52.86 C |
| ATOM | 171 | CE2 | PHE | H | 74 | 4.230 | −26.379 | 16.375 | 1.00 | 53.68 C |
| ATOM | 172 | CZ | PHE | H | 74 | 4.918 | −26.281 | 15.186 | 1.00 | 51.51 C |
| ATOM | 173 | OXT | PHE | H | 74 | 9.469 | −29.102 | 18.345 | 1.00 | 100.17 O1− |
| TER | 174 | | PHE | H | 74 | | | | | |

TABLE 3-continued

Atomic coordinates of P6 residues and of the residues involved in the binding of P6 to the β clamp, in the crystal of P6 peptide co-crystallized with the β ring.

| HETATM | 175 | O | HOH | H | 86 | 5.592 | −15.725 | 23.553 | 1.00 | 33.16 | O |
|---|---|---|---|---|---|---|---|---|---|---|---|
| END | | | | | | | | | | | |

A free energy decomposition analysis (see Material and Methods for details) of this complex was performed (FIG. 2B) and the most important interactions are similar to the initial complex 1OK7, as expected. The canonical sequence LF advantageously replaces the LGL sequence in C-ter of the peptide (FIG. 2B). The P6 peptide acetyl group also forms two hydrogen bonds with the Nα of residues $R_{365}$ and $L_{366}$ of the β monomer which probably account for the 10 fold increase in stability of the P6 peptide as compared to P5 (Table 1). Despite its reduced size, the P6 peptide therefore has an increased affinity for the β-clamp with respect to the original peptide P1.

1.2.3. Design of Non-Natural Peptides Ligands with Increased Binding Affinity.

P6 was further used as a lead to introduce modifications aimed at increasing the affinity of the ligand for the β clamp. Because the natural ligand binds to the pocket essentially through hydrophobic interactions, the aim was to extend the network of such interactions. A first set of modifications concerned position 2, where the leucine residue was replaced by a cyclohexyl-L-alanyl group (Cha) (P7, table 4 and table 7). An initial modeling analysis, using programs MCSS and SEED, indicated that this modification provides a Van der Waals energy contribution two-fold higher than that with the natural $L_3$ residue, and is the most efficient group tested (Table 4). It also results in a 6 fold increase in the interaction, as measured by SPR (Table 4 and Table 7, compare P6 and P7). Attempts to increase the side chain length resulted in a drastic reduction of the affinity (Table 4 and Table 7, P8) while other modifications like homoleucyl (hLeu) or neopentylglycyl (NptGly, also called tertiomethylbutylglycine, tBMG) did not yield any gain in affinity (Table 4 and Table 7, P9 and P10), probably indicating that the area available for an efficient interaction is limited.

TABLE 4

Effect of site-specific modifications of the second residue on the interaction of peptide with the *E. coli* β clamp.

| # | sequence | IC$_{50}$ (μM) | SEQ ID No: |
|---|---|---|---|
| P6 | AcQLDLF | 1.12 | 6 |
| P7 | Ac Q ChaDLF | 0.17 | 7 |
| P8 | Ac Q hCha DLF | 82.8 | 8 |
| P9 | Ac Q hLeu DLF | 0.74 | 9 |
| P10 | Ac Q NptGly DLF | 0.99 | 10 |

Cha: cyclohexylalanine,
hCha: homocyclohexylalanine,
hLeu: homoleucine,
NptGly: neopentylglycyl.

A second set of similar modifications was introduced at position $L_4$, but no increase in affinity was observed as compared to P7 (Table 5).

TABLE 5

Effect of site-specific modifications of the $L_4$, residue on the interaction of peptide with the *E. coli* β clamp.

| # | sequence | IC$_{50}$ (μM) | SEQ ID No: |
|---|---|---|---|
| P6 | AcQLDLF | 1.12 | 6 |
| P7 | Ac Q Cha DLF | 0.17 | 7 |
| P16 | Ac Q Cha D hLeu F | 0.23 | 16 |
| P17 | Ac Q Cha D Cha F | 0.31 | 17 |
| P18 | Ac Q Cha D hCha F | 0.72 | 18 |
| P19 | Ac Q ChaD NptGly F | 5.63 | 19 |

Finally, several modifications were introduced on the terminal phenylalanine benzyl ring (Table 6). The binding affinity was found to increase significantly with the size of the ring substituent (p-methyl<p-chloro<p-bromo<3,4-dichloro)(see P11, P12, P13, and P14, respectively). An IC$_{50}$ value of 70 nM was measured for the 3,4-dichlorophenylalanine containing peptide (P14), which represent a 15, 115 and 4 fold increase as compared to P6, P1 and the full PolIV enzyme, respectively (Table 6 and Table 7). To the contrary, replacement of the terminal phenylalanine by a cyclohexyl-L-alanyl group (Cha), a tryptophan or a 2-amino-tetradecanoic acid (Atda) (P20, P21 and P22, Table 6) led to a decreased affinity.

TABLE 6

Effect of modifications on the terminal phenylalanine benzyl ring on the interaction of peptide with the *E. coli* β clamp.

| # | sequence | IC$_{50}$ (μM) | SEQ ID No: |
|---|---|---|---|
| P6 | AcQLDLF | 1.12 | 6 |
| P11 | Ac-Q Cha DL pMeF | 0.26 | 11 |
| P12 | Ac-Q Cha DL pClF | 0.16 | 12 |
| P13 | Ac-Q Cha DL pBrF | 0.10 | 13 |
| P14 | Ac-Q Cha DL diClF | 0.072 | 14 |
| P20 | Ac-Q Cha DL Cha | 0.41 | 20 |
| P21 | Ac-Q Cha DLW | 0.64 | 21 |
| P22 | Ac-Q Cha DL Atda | 3.72 | 22 |

The interactions of the various peptides with the β ring were also evaluated using a polymerase competition assay where primer elongation performed by the polIV DNA polymerase is challenged by various concentrations of the peptides to be tested[17]. While the β independent activity of the polymerase is insensitive to the peptides, indicating that they have no direct effect on the enzyme activity, the β dependent elongation activity is differentially inhibited depending on the affinity of the peptide for its target (FIG. 4). A quantitative analysis of the biochemical assays is shown in FIG. 7. Although this approach is less sensitive than SPR, a good correlation is observed between the two methods (FIG. 4).

TABLE 7

Influence of the C-terminal tripeptide sequence and effect of site specific modifications on the interaction of peptide with the E. coli β clamp, as measured by SPR experiments.

| # | sequence | IC$_{50}$ (μM) | Ki (10$^6$ M$^{-1}$) | ΔG (Kcal/mol) | Seq Id No: |
|---|---|---|---|---|---|
| PolIV | | 0.29 | 4.7 | −9.09 | |
| P1 | RQLVLGL | 8.85 | 0.15 | −7.06 | 1 |
| P2 | RQLVLL | 21.53 | 0.0063 | −6.54 | 2 |
| P3 | RQLVLF | 8.62 | 0.15 | −7.04 | 3 |
| P4 | RQLVFL | 256 | ∅ | ∅ | 4 |
| P5 | QLDLF | 12.44 | 0.11 | −6.87 | 5 |
| P6 | AcQLDLF | 1.12 | 1.2 | −8.22 | 6 |
| P7 | Ac Q ChaDLF | 0.17 | 8.01 | −9.42 | 7 |
| P8 | Ac Q hCha DLF | 82.8 | 16.4 | −5.74 | 8 |
| P9 | Ac Q Hol DLF | 0.74 | 1.84 | −8.54 | 9 |
| P10 | Ac Q NptGly DLF | 0.99 | 1.36 | −8.36 | 10 |
| P11 | Ac-Q Cha DL pMeF | 0.26 | 8.43 | −9.44 | 11 |
| P12 | Ac-Q Cha DL pClF | 0.16 | 13.7 | −9.73 | 12 |
| P13 | Ac-Q Cha DL pBrF | 0.096 | 13.49 | −9.71 | 13 |
| P14 | Ac-Q Cha DL diClF | 0.077 | 17 | −9.85 | 14 |

∅: not determined.
Ki = (1 + K$_A$[β])/IC50.
ΔG = −RT ln Ki.
PolIV: E coli DNA polymerase IV.

The following table 8 presents the analytical data concerning the most relevant peptides described in this study.

TABLE 8

Sequence and analytical data of C-terminal peptides of the E. coli DNA polymerase IV and analogues (related to FIG. 1 and table 7).

| Peptide | compound | HPLC t$_R$ (min) | PURITY [%] HPLC | MS FOUND CALC. [M + H$^+$] MASS | SEQ ID No: |
|---|---|---|---|---|---|
| P1 | H-Arg-Gln-Leu-Val-Leu-Gly-Leu-OH— | 11.97 | 98.2 | 799.0 799.9 | 1 |
| P2 | H-Arg-Gln-Leu-Val-Leu-Leu-OH | 11.50 | 93.0 | 740.5 741.9 | 2 |
| P3 | H-Arg-Gln-Leu-Val-Leu-Phe-OH | 12.13 | 92.1 | 774.5 775.8 | 3 |
| P4 | H-Arg-Gln-Leu-Val-Phe-Leu-OH | 12.02 | 92.5 | 774.5 775.5 | 4 |
| P5 | H-Gln-Leu-Asp-Leu-Phe-OH | 12.55 | 90 | 634.3 634.8 | 5 |
| P6 | Ac-Gln-Leu-Asp-Leu-Phe-OH | 13.25 | 92.5 | 676.3 677.3 | 6 |
| P7 | Ac-Gln-Cha-Asp-Leu-Phe-OH | 15.12 | 95 | 716.8 717.7 | 7 |
| P8 | Ac-Gln-hCha-Asp-Leu-Phe-OH | 16.23 | 50.93 | 730.8 731.4 | 8 |
| P9 | Ac-Gln-Hol-Asp-Leu-Phe-OH | 14.23 | 90 | 690.8 691.0 | 9 |
| P10 | Ac-Gln-NptGly-Asp-Leu-Phe-OH | 13.99 | 94 | 702.8 691.7 | 10 |
| P11 | Ac-Gln-Cha-Asp-Leu-pMePhe-OH | 15.88 | 97 | 716.4 732.7 | 11 |
| P12 | Ac-Gln-Cha-Asp-Leu-pClPhe-OH | 16.27 | 93 | 736.3 752.7 | 12 |
| P13 | Ac-Gln-Cha-Asp-Leu-pBrPhe-OH | 16.45 | 95 | 794.3 799.8 | 13 |
| P14 | Ac-Gln-Cha-Asp-Leu-(3,4-di-Cl)Phe-OH | 17.18 | 91 | 784.3 786.9 | 14 |

Cha: beta-cyclohexyl-L-alanyl;
hCha: L-homoCha;
Hol: L-homoleucyl;
NptGly: neopentylglycyl;
pMePhe: 4-methyl-L-phenylalanyl;
pClPhe: 4-chloro-L-phenylalanyl;
pBrPhe: 4-bromo-L-phenylalanyl;
(3,4-di-Cl)Phe: 3,4-dichloro-L-phenylalanyl 1.2.4. Crystal Structure of the Modified Peptides β Ring Complexes.

Peptides P12 and P14 were co-crystallized with the β ring. The structures were solved by molecular replacement at 2.6 Å and 1.95 Å resolution respectively, using the 1OK7 structure as a search model. As for the previous P6-β complex, both complexes crystallized in space group P1 but with one ring per asymmetric unit (Table 3). Each monomer of the rings binds a peptide, and both ligands adopt a similar configuration (rmsd=0.70 Å and 0.78 Å for the peptides atoms of P12 and P14, respectively), indicating that the modified peptides essentially adopt the same conformation and location in the binding pocket. The Cha moiety is located at the same position as the L$_3$ residue of P6 but extends its interaction further within a hydrophobic pocket shaped by the P$_{363}$, V$_{344}$, M$_{362}$ and R$_{365}$ β residues (FIG. 5A) and interacts with the last three residues. These extra interactions probably account for the increased affinity of P7 as compared to P6 (table 1). Additionally, the Nα of this modified residue interacts with the Cα=O of P$_{363}$. The p-chloro and 3,4-dichloro F residues of P12 and P14 are almost superimposed (FIG. 5B) and interact with β residues T$_{172}$, L$_{177}$ and V$_{247}$. The chlorine atom in meta position in P14 establishes an halogen bond with the hydroxyl oxygen of T$_{172}$, with contact distance and angle in good agreement with previously published data (d=3.17 Å and θ=148.71°)[20]. In contrast, the para chlorine atoms of both P12 and P14 do not establish such type of interaction because the distances with adjacent oxygen atoms of β residues are too large.

The atomic coordinates P12 and P14, co-crystalized with the β clamp, are disclosed in the following Tables 9 and 10.

These tables indicate the atomic coordinates of the peptides and of the binding site of the β clamp (residues≤5 Å from the ligand). The other residues have the same positions as in the previously determined structure (PDB 1OK7) also described in U.S. Pat. No. 7,635,583.

TABLE 9

Atomic coordinates of P12 residues and of the residues involved in the binding of P12 to the β clamp, in the crystal of P12 peptide co-crystallized with the β ring.

| | | | | | | | | | | |
|---|---|---|---|---|---|---|---|---|---|---|
| ATOM | 1 | NH1 | ARG | A | 152 | −13.878 | 13.827 | 24.977 | 1.00 | 41.13 N1+ |
| TER | 2 | | ARG | A | 152 | | | | | |
| ATOM | 3 | CD2 | LEU | A | 155 | −9.376 | 16.306 | 22.697 | 1.00 | 33.78 C |
| TER | 4 | | LEU | A | 155 | | | | | |
| ATOM | 5 | CB | THR | A | 172 | −5.579 | 13.660 | 24.332 | 1.00 | 10.80 C |
| ATOM | 6 | CG2 | THR | A | 172 | −6.162 | 15.062 | 24.379 | 1.00 | 3.00 C |
| ATOM | 7 | OG1 | THR | A | 172 | −6.396 | 12.784 | 25.111 | 1.00 | 11.87 O |
| TER | 8 | | THR | A | 172 | | | | | |
| ATOM | 9 | N | GLY | A | 174 | −9.375 | 11.662 | 24.270 | 1.00 | 22.35 N |
| ATOM | 10 | CA | GLY | A | 174 | −10.197 | 11.573 | 25.471 | 1.00 | 21.94 C |
| ATOM | 11 | C | GLY | A | 174 | −9.904 | 10.341 | 26.321 | 1.00 | 26.11 C |
| ATOM | 12 | O | GLY | A | 174 | −10.187 | 10.331 | 27.522 | 1.00 | 24.70 O |
| ATOM | 13 | N | HIS | A | 175 | −9.341 | 9.286 | 25.699 | 1.00 | 23.67 N |
| ATOM | 14 | CA | HIS | A | 175 | −9.001 | 8.008 | 26.347 | 1.00 | 23.91 C |
| ATOM | 15 | C | HIS | A | 175 | −7.479 | 7.869 | 26.584 | 1.00 | 24.57 C |
| ATOM | 16 | O | HIS | A | 175 | −7.046 | 7.395 | 27.635 | 1.00 | 24.56 O |
| ATOM | 17 | CB | HIS | A | 175 | −9.546 | 6.822 | 25.519 | 1.00 | 25.86 C |
| ATOM | 18 | CG | HIS | A | 175 | −10.971 | 7.005 | 25.080 | 1.00 | 30.11 C |
| ATOM | 19 | CD2 | HIS | A | 175 | −11.486 | 7.140 | 23.838 | 1.00 | 32.30 C |
| ATOM | 20 | ND1 | HIS | A | 175 | −12.005 | 7.082 | 25.997 | 1.00 | 32.23 N |
| ATOM | 21 | CE1 | HIS | A | 175 | −13.107 | 7.245 | 25.288 | 1.00 | 31.59 C |
| ATOM | 22 | NE2 | HIS | A | 175 | −12.845 | 7.286 | 23.985 | 1.00 | 32.09 N |
| ATOM | 23 | N | ARG | A | 176 | −6.685 | 8.290 | 25.610 | 1.00 | 18.69 N |
| ATOM | 24 | CA | ARG | A | 176 | −5.234 | 8.264 | 25.702 | 1.00 | 18.59 C |
| ATOM | 25 | C | ARG | A | 176 | −4.604 | 9.609 | 25.304 | 1.00 | 24.08 C |
| ATOM | 26 | O | ARG | A | 176 | −5.276 | 10.463 | 24.713 | 1.00 | 23.83 O |
| ATOM | 27 | N | LEU | A | 177 | −3.347 | 9.832 | 25.715 | 1.00 | 19.54 N |
| ATOM | 28 | CA | LEU | A | 177 | −2.653 | 11.088 | 25.503 | 1.00 | 18.04 C |
| ATOM | 29 | CB | LEU | A | 177 | −2.873 | 11.987 | 26.745 | 1.00 | 17.92 C |
| ATOM | 30 | CG | LEU | A | 177 | −1.963 | 13.211 | 26.971 | 1.00 | 21.84 C |
| ATOM | 31 | CD1 | LEU | A | 177 | −2.328 | 14.347 | 26.066 | 1.00 | 21.30 C |
| ATOM | 32 | CD2 | LEU | A | 177 | −2.004 | 13.663 | 28.416 | 1.00 | 22.36 C |
| TER | 33 | | LEU | A | 177 | | | | | |
| ATOM | 34 | CA | PRO | A | 242 | −8.284 | 20.266 | 27.211 | 1.00 | 10.30 C |
| ATOM | 35 | C | PRO | A | 242 | −7.012 | 20.416 | 28.076 | 1.00 | 16.74 C |
| ATOM | 36 | CB | PRO | A | 242 | −8.798 | 18.838 | 27.188 | 1.00 | 11.44 C |
| ATOM | 37 | CG | PRO | A | 242 | −8.164 | 18.255 | 25.944 | 1.00 | 16.16 C |
| ATOM | 38 | CD | PRO | A | 242 | −8.332 | 19.361 | 24.955 | 1.00 | 11.62 C |
| ATOM | 39 | N | ASP | A | 243 | −7.224 | 20.463 | 29.391 | 1.00 | 14.24 N |
| ATOM | 40 | CA | ASP | A | 243 | −6.222 | 20.608 | 30.438 | 1.00 | 14.52 C |
| ATOM | 41 | C | ASP | A | 243 | −5.454 | 19.282 | 30.618 | 1.00 | 21.86 C |
| ATOM | 42 | O | ASP | A | 243 | −5.842 | 18.424 | 31.416 | 1.00 | 25.37 O |
| ATOM | 43 | N | TYR | A | 244 | −4.471 | 19.055 | 29.748 | 1.00 | 15.95 N |
| ATOM | 44 | CA | TYR | A | 244 | −3.688 | 17.827 | 29.764 | 1.00 | 15.04 C |
| ATOM | 45 | CB | TYR | A | 244 | −2.900 | 17.645 | 28.437 | 1.00 | 14.90 C |
| TER | 46 | | TYR | A | 244 | | | | | |
| ATOM | 47 | NH1 | ARG | A | 246 | −9.401 | 15.913 | 36.324 | 1.00 | 21.44 N1+ |
| ATOM | 48 | CB | VAL | A | 247 | −4.905 | 13.902 | 32.710 | 1.00 | 29.59 C |
| ATOM | 49 | CG1 | VAL | A | 247 | −5.480 | 12.551 | 33.104 | 1.00 | 29.67 C |
| ATOM | 50 | CG2 | VAL | A | 247 | −6.024 | 14.870 | 32.343 | 1.00 | 29.06 C |
| TER | 51 | | VAL | A | 247 | | | | | |
| ATOM | 52 | O | PHE | A | 278 | −11.396 | −2.943 | 23.858 | 1.00 | 27.53 O |
| TER | 53 | | PHE | A | 278 | | | | | |
| ATOM | 54 | N | ASN | A | 320 | −7.095 | −1.216 | 26.969 | 1.00 | 26.00 N |
| ATOM | 55 | CB | ASN | A | 320 | −8.050 | −0.275 | 24.887 | 1.00 | 19.44 C |
| ATOM | 56 | CG | ASN | A | 320 | −8.114 | −0.289 | 23.378 | 1.00 | 25.87 C |
| ATOM | 57 | ND2 | ASN | A | 320 | −9.197 | 0.247 | 22.826 | 1.00 | 19.30 N |
| ATOM | 58 | OD1 | ASN | A | 320 | −7.179 | −0.699 | 22.685 | 1.00 | 16.42 O |
| TER | 59 | | ASN | A | 320 | | | | | |
| ATOM | 60 | CD2 | TYR | A | 323 | −6.890 | 3.229 | 24.491 | 1.00 | 20.56 C |
| ATOM | 61 | CE2 | TYR | A | 323 | −8.089 | 3.767 | 24.028 | 1.00 | 21.88 C |
| ATOM | 62 | cz | TYR | A | 323 | −8.254 | 4.015 | 22.675 | 1.00 | 30.51 C |
| ATOM | 63 | OH | TYR | A | 323 | −9.422 | 4.548 | 22.199 | 1.00 | 34.44 O |
| TER | 64 | | TYR | A | 323 | | | | | |
| ATOM | 65 | O | SER | A | 343 | −8.420 | 0.538 | 36.986 | 1.00 | 43.35 O |
| ATOM | 66 | CA | VAL | A | 344 | −9.412 | 2.967 | 38.022 | 1.00 | 37.68 C |
| ATOM | 67 | C | VAL | A | 344 | −8.749 | 4.286 | 37.541 | 1.00 | 39.37 C |
| ATOM | 68 | O | VAL | A | 344 | −9.430 | 5.162 | 37.004 | 1.00 | 37.60 O |

TABLE 9-continued

Atomic coordinates of P12 residues and of the residues involved in the binding of P12 to the β clamp, in the crystal of P12 peptide co-crystallized with the β ring.

| ATOM | 69 | CB | VAL | A | 344 | −10.716 | 3.216 | 38.843 | 1.00 | 41.47 | C |
|---|---|---|---|---|---|---|---|---|---|---|---|
| ATOM | 70 | CG1 | VAL | A | 344 | −11.660 | 2.025 | 38.749 | 1.00 | 41.11 | C |
| TER | 71 | | VAL | A | 344 | | | | | | |
| ATOM | 72 | CB | SER | A | 346 | −4.248 | 7.581 | 33.672 | 1.00 | 36.35 | C |
| TER | 73 | | SER | A | 346 | | | | | | |
| ATOM | 74 | O | VAL | A | 360 | −2.861 | 8.288 | 27.992 | 1.00 | 21.29 | O |
| ATOM | 75 | CG1 | VAL | A | 360 | −2.051 | 9.515 | 31.551 | 1.00 | 22.57 | C |
| TER | 76 | | VAL | A | 360 | | | | | | |
| ATOM | 77 | N | MET | A | 362 | −5.771 | 5.847 | 29.897 | 1.00 | 24.01 | N |
| ATOM | 78 | CA | MET | A | 362 | −6.824 | 5.610 | 30.866 | 1.00 | 25.90 | C |
| ATOM | 79 | C | MET | A | 362 | −7.277 | 4.123 | 30.792 | 1.00 | 30.54 | C |
| ATOM | 80 | O | MET | A | 362 | −7.461 | 3.593 | 29.689 | 1.00 | 29.30 | O |
| ATOM | 81 | CB | MET | A | 362 | −7.994 | 6.560 | 30.587 | 1.00 | 29.26 | C |
| ATOM | 82 | CG | MET | A | 362 | −8.871 | 6.790 | 31.773 | 1.00 | 34.65 | C |
| ATOM | 83 | SD | MET | A | 362 | −8.107 | 7.741 | 33.104 | 1.00 | 40.06 | s |
| ATOM | 84 | CE | MET | A | 362 | −9.291 | 7.371 | 34.427 | 1.00 | 36.64 | C |
| ATOM | 85 | N | PRO | A | 363 | −7.464 | 3.423 | 31.935 | 1.00 | 28.36 | N |
| ATOM | 86 | CA | PRO | A | 363 | −7.885 | 2.016 | 31.872 | 1.00 | 27.57 | C |
| ATOM | 87 | C | PRO | A | 363 | −9.367 | 1.784 | 31.553 | 1.00 | 32.79 | C |
| ATOM | 88 | O | PRO | A | 363 | −10.161 | 2.723 | 31.445 | 1.00 | 30.76 | O |
| ATOM | 89 | CB | PRO | A | 363 | −7.534 | 1.508 | 33.276 | 1.00 | 29.22 | C |
| ATOM | 90 | CG | PRO | A | 363 | −7.733 | 2.646 | 34.141 | 1.00 | 33.99 | C |
| ATOM | 91 | CD | PRO | A | 363 | −7.288 | 3.852 | 33.338 | 1.00 | 30.19 | C |
| ATOM | 92 | N | MET | A | 364 | −9.735 | 0.505 | 31.409 | 1.00 | 33.12 | N |
| ATOM | 93 | CA | MET | A | 364 | −11.116 | 0.063 | 31.233 | 1.00 | 34.28 | C |
| ATOM | 94 | C | MET | A | 364 | −11.510 | −0.892 | 32.363 | 1.00 | 38.91 | C |
| ATOM | 95 | CB | MET | A | 364 | −11.392 | −0.494 | 29.827 | 1.00 | 37.35 | C |
| ATOM | 96 | CG | MET | A | 364 | −10.591 | −1.704 | 29.437 | 1.00 | 42.38 | C |
| ATOM | 97 | SD | MET | A | 364 | −10.644 | −1.982 | 27.634 | 1.00 | 48.21 | s |
| ATOM | 98 | CE | MET | A | 364 | −12.355 | −2.535 | 27.415 | 1.00 | 45.40 | C |
| ATOM | 99 | N | ARG | A | 365 | −12.802 | −0.893 | 32.770 | 1.00 | 36.16 | N |
| ATOM | 100 | CA | ARG | A | 365 | −13.345 | −1.727 | 33.857 | 1.00 | 54.18 | C |
| ATOM | 101 | O | ARG | A | 365 | −13.715 | −3.627 | 32.448 | 1.00 | 15.77 | O |
| ATOM | 102 | CB | ARG | A | 365 | −14.777 | −1.280 | 34.190 | 1.00 | 54.40 | C |
| ATOM | 103 | CG | ARG | A | 365 | −14.987 | −0.808 | 35.628 | 1.00 | 61.81 | C |
| ATOM | 104 | CD | ARG | A | 365 | −16.323 | −0.093 | 35.795 | 1.00 | 67.50 | C |
| ATOM | 105 | NE | ARG | A | 365 | −16.385 | 0.668 | 37.050 | 1.00 | 70.43 | N |
| ATOM | 106 | CZ | ARG | A | 365 | −17.177 | 1.718 | 37.255 | 1.00 | 69.73 | C |
| ATOM | 107 | NH1 | ARG | A | 365 | −17.980 | 2.151 | 36.291 | 1.00 | 47.59 | N1+ |
| ATOM | 108 | NH2 | ARG | A | 365 | −17.162 | 2.350 | 38.424 | 1.00 | 45.96 | N |
| TER | 109 | | ARG | A | 365 | | | | | | |
| HETATM | 110 | O | HOH | A | 397 | −12.948 | −0.572 | 24.569 | 1.00 | 24.99 | O |
| HETATM | 111 | O | HOH | A | 422 | −15.206 | 5.096 | 38.996 | 1.00 | 47.81 | O |
| HETATM | 112 | O | HOH | A | 433 | −8.020 | 1.912 | 27.730 | 1.00 | 9.25 | O |
| HETATM | 113 | O | HOH | C | 24 | −11.224 | 1.716 | 24.238 | 1.00 | 30.48 | O |
| HETATM | 114 | C | ACE | C | 367 | −14.628 | 0.704 | 29.591 | 1.00 | 35.56 | C |
| HETATM | 115 | O | ACE | C | 367 | −14.221 | 1.136 | 30.667 | 1.00 | 30.52 | O |
| HETATM | 116 | CH3 | ACE | C | 367 | −15.612 | −0.454 | 29.524 | 1.00 | 29.87 | C |
| ATOM | 117 | N | GLN | C | 368 | −14.292 | 1.401 | 28.359 | 1.00 | 30.56 | N |
| ATOM | 118 | CA | GLN | C | 368 | −13.424 | 2.699 | 28.412 | 1.00 | 25.45 | C |
| ATOM | 119 | C | GLN | C | 368 | −13.778 | 3.790 | 29.559 | 1.00 | 32.24 | C |
| ATOM | 120 | O | GLN | C | 368 | −14.830 | 4.442 | 29.488 | 1.00 | 32.94 | O |
| ATOM | 121 | CB | GLN | C | 368 | −13.142 | 3.398 | 26.993 | 1.00 | 29.55 | C |
| ATOM | 122 | CG | GLN | C | 368 | −11.862 | 4.252 | 26.986 | 1.00 | 29.78 | C |
| ATOM | 123 | CD | GLN | C | 368 | −10.609 | 3.491 | 27.350 | 1.00 | 23.65 | C |
| ATOM | 124 | NE2 | GLN | C | 368 | −9.792 | 3.893 | 28.463 | 1.00 | 24.50 | N |
| ATOM | 125 | OE1 | GLN | C | 368 | −10.426 | 2.411 | 26.809 | 1.00 | 27.24 | O |
| TER | 126 | | GLN | C | 368 | | | | | | |
| HETATM | 127 | N | ALC | C | 369 | −12.687 | 4.147 | 30.488 | 1.00 | 28.64 | N |
| HETATM | 128 | CA | ALC | C | 369 | −12.514 | 5.508 | 30.964 | 1.00 | 29.77 | C |
| HETATM | 129 | C | ALC | C | 369 | −11.636 | 6.300 | 29.995 | 1.00 | 30.06 | C |
| HETATM | 130 | O | ALC | C | 369 | −10.844 | 5.719 | 29.263 | 1.00 | 32.57 | O |
| HETATM | 131 | CB | ALC | C | 369 | −11.826 | 5.516 | 32.374 | 1.00 | 29.41 | C |
| HETATM | 132 | CG | ALC | C | 369 | −12.462 | 4.800 | 33.632 | 1.00 | 27.38 | C |
| HETATM | 133 | CD1 | ALC | C | 369 | −11.611 | 3.659 | 34.076 | 1.00 | 26.63 | C |
| HETATM | 134 | CD2 | ALC | C | 369 | −13.892 | 4.431 | 33.398 | 1.00 | 29.06 | C |
| HETATM | 135 | CE1 | ALC | C | 369 | −12.176 | 2.854 | 35.208 | 1.00 | 26.40 | C |
| HETATM | 136 | CE2 | ALC | C | 369 | −14.487 | 3.799 | 34.618 | 1.00 | 36.93 | C |
| HETATM | 137 | cz | ALC | C | 369 | −13.665 | 2.730 | 35.276 | 1.00 | 30.08 | C |
| ATOM | 138 | N | ASP | C | 370 | −11.984 | 7.629 | 29.488 | 1.00 | 34.94 | N |
| ATOM | 139 | CA | ASP | C | 370 | −12.550 | 8.830 | 30.301 | 1.00 | 34.00 | C |
| ATOM | 140 | C | ASP | C | 370 | −11.474 | 9.729 | 31.120 | 1.00 | 30.52 | C |
| ATOM | 141 | O | ASP | C | 370 | −11.377 | 9.697 | 32.347 | 1.00 | 25.64 | O |
| ATOM | 142 | CB | ASP | C | 370 | −14.029 | 8.546 | 30.909 | 1.00 | 38.94 | C |
| ATOM | 143 | CG | ASP | C | 370 | −15.012 | 8.727 | 29.752 | 1.00 | 40.34 | C |
| ATOM | 144 | OD1 | ASP | C | 370 | −16.182 | 8.114 | 29.765 | 1.00 | 59.35 | O |
| ATOM | 145 | OD2 | ASP | C | 370 | −14.418 | 9.287 | 28.668 | 1.00 | 30.05 | O1− |

TABLE 9-continued

Atomic coordinates of P12 residues and of the residues involved in the binding of P12 to the β clamp, in the crystal of P12 peptide co-crystallized with the β ring.

| ATOM | 146 | N | LEU | C | 371 | −10.560 | 10.539 | 30.269 | 1.00 | 32.14 | N |
|---|---|---|---|---|---|---|---|---|---|---|---|
| ATOM | 147 | CA | LEU | C | 371 | −9.624 | 11.571 | 30.769 | 1.00 | 33.35 | C |
| ATOM | 148 | C | LEU | C | 371 | −10.269 | 12.914 | 31.093 | 1.00 | 36.56 | C |
| ATOM | 149 | O | LEU | C | 371 | −9.703 | 13.671 | 31.882 | 1.00 | 38.88 | O |
| ATOM | 150 | CB | LEU | C | 371 | −8.465 | 11.790 | 29.754 | 1.00 | 29.71 | C |
| ATOM | 151 | CG | LEU | C | 371 | −7.489 | 10.663 | 29.542 | 1.00 | 32.92 | C |
| ATOM | 152 | CD1 | LEU | C | 371 | −6.748 | 10.753 | 28.242 | 1.00 | 21.26 | C |
| ATOM | 153 | CD2 | LEU | C | 371 | −6.637 | 10.343 | 30.752 | 1.00 | 23.07 | C |
| TER | 154 | | LEU | C | 371 | | | | | | |
| HETATM | 155 | N | 200 | C | 372 | −11.514 | 13.352 | 30.399 | 1.00 | 31.07 | N |
| HETATM | 156 | CA | 200 | C | 372 | −12.085 | 14.735 | 30.622 | 1.00 | 32.30 | C |
| HETATM | 157 | C | 200 | C | 372 | −13.594 | 14.731 | 30.756 | 1.00 | 37.62 | C |
| HETATM | 158 | O | 200 | C | 372 | −14.200 | 15.440 | 31.810 | 1.00 | 41.91 | O |
| HETATM | 159 | CB | 200 | C | 372 | −11.640 | 15.817 | 29.612 | 1.00 | 30.34 | C |
| HETATM | 160 | CG | 200 | C | 372 | −10.185 | 15.711 | 29.135 | 1.00 | 25.13 | C |
| HETATM | 161 | CD1 | 200 | C | 372 | −9.909 | 15.210 | 27.863 | 1.00 | 20.80 | C |
| HETATM | 162 | CD2 | 200 | C | 372 | −9.161 | 16.082 | 29.995 | 1.00 | 22.71 | C |
| HETATM | 163 | CE1 | 200 | C | 372 | −8.592 | 15.088 | 27.455 | 1.00 | 22.75 | C |
| HETATM | 164 | CE2 | 200 | C | 372 | −7.842 | 15.960 | 29.593 | 1.00 | 22.47 | C |
| HETATM | 165 | CZ | 200 | C | 372 | −7.572 | 15.459 | 28.324 | 1.00 | 26.57 | C |
| HETATM | 166 | CL | 200 | C | 372 | −5.931 | 15.288 | 27.829 | 1.00 | 37.22 | CL |
| HETATM | 167 | OXT | 200 | C | 372 | −14.362 | 13.982 | 29.828 | 1.00 | 44.19 | O |
| END | | | | | | | | | | | |

TABLE 10

Atomic coordinates of P14 residues and of the residues involved in the binding of P14 to the β clamp, in the crystal of P14 peptide co-crystallized with the β ring.

| ATOM | 1 | NH1 | ARG | A | 152 | −13.000 | 14.676 | 25.384 | 1.00 | 41.87 | N1+ |
|---|---|---|---|---|---|---|---|---|---|---|---|
| TER | 2 | | ARG | A | 152 | | | | | | |
| ATOM | 3 | CD2 | LEU | A | 155 | −8.771 | 17.218 | 22.511 | 1.00 | 32.76 | C |
| TER | 4 | | LEU | A | 155 | | | | | | |
| ATOM | 5 | CB | THR | A | 172 | −5.062 | 14.269 | 24.018 | 1.00 | 29.73 | C |
| ATOM | 6 | CG2 | THR | A | 172 | −5.795 | 15.620 | 24.122 | 1.00 | 26.88 | C |
| ATOM | 7 | OG1 | THR | A | 172 | −5.728 | 13.271 | 24.786 | 1.00 | 28.48 | O |
| TER | 8 | | THR | A | 172 | | | | | | |
| ATOM | 9 | N | GLY | A | 174 | −8.679 | 12.290 | 24.030 | 1.00 | 26.79 | N |
| ATOM | 10 | CA | GLY | A | 174 | −9.451 | 12.319 | 25.270 | 1.00 | 28.12 | C |
| ATOM | 11 | C | GLY | A | 174 | −9.367 | 11.041 | 26.069 | 1.00 | 32.47 | C |
| ATOM | 12 | O | GLY | A | 174 | −9.848 | 10.979 | 27.199 | 1.00 | 31.98 | O |
| ATOM | 13 | N | HIS | A | 175 | −8.715 | 10.024 | 25.494 | 1.00 | 30.75 | N |
| ATOM | 14 | CA | HIS | A | 175 | −8.481 | 8.734 | 26.139 | 1.00 | 30.80 | C |
| ATOM | 15 | C | HIS | A | 175 | −6.976 | 8.530 | 26.320 | 1.00 | 30.70 | C |
| ATOM | 16 | O | HIS | A | 175 | −6.557 | 8.002 | 27.335 | 1.00 | 29.87 | O |
| ATOM | 17 | CB | HIS | A | 175 | −9.131 | 7.602 | 25.325 | 1.00 | 32.00 | C |
| ATOM | 18 | CG | HIS | A | 175 | −10.595 | 7.832 | 25.079 | 1.00 | 35.24 | C |
| ATOM | 19 | CD2 | HIS | A | 175 | −11.259 | 7.998 | 23.916 | 1.00 | 37.80 | C |
| ATOM | 20 | ND1 | HIS | A | 175 | −11.496 | 7.948 | 26.130 | 1.00 | 37.36 | N |
| ATOM | 21 | CE1 | HIS | A | 175 | −12.677 | 8.158 | 25.576 | 1.00 | 37.24 | C |
| ATOM | 22 | NE2 | HIS | A | 175 | −12.587 | 8.212 | 24.247 | 1.00 | 38.20 | N |
| ATOM | 23 | N | ARG | A | 176 | −6.162 | 8.980 | 25.337 | 1.00 | 25.93 | N |
| ATOM | 24 | CA | ARG | A | 176 | −4.709 | 8.899 | 25.425 | 1.00 | 23.72 | C |
| ATOM | 25 | C | ARG | A | 176 | −4.078 | 10.213 | 25.009 | 1.00 | 27.35 | C |
| ATOM | 26 | O | ARG | A | 176 | −4.648 | 10.950 | 24.212 | 1.00 | 24.69 | O |
| ATOM | 27 | N | LEU | A | 177 | −2.885 | 10.489 | 25.534 | 1.00 | 25.59 | N |
| ATOM | 28 | CA | LEU | A | 177 | −2.204 | 11.738 | 25.266 | 1.00 | 25.33 | C |
| ATOM | 29 | CB | LEU | A | 177 | −2.431 | 12.671 | 26.488 | 1.00 | 25.95 | C |
| ATOM | 30 | CG | LEU | A | 177 | −1.853 | 14.080 | 26.442 | 1.00 | 29.85 | C |
| ATOM | 31 | CD1 | LEU | A | 177 | −2.845 | 15.053 | 27.040 | 1.00 | 31.56 | C |
| TER | 32 | | LEU | A | 177 | | | | | | |
| ATOM | 33 | CA | PRO | A | 242 | −7.701 | 20.996 | 27.178 | 1.00 | 30.57 | C |
| ATOM | 34 | C | PRO | A | 242 | −6.353 | 21.180 | 27.870 | 1.00 | 35.62 | C |
| ATOM | 35 | O | PRO | A | 242 | −5.277 | 21.201 | 27.239 | 1.00 | 31.98 | O |
| ATOM | 36 | CB | PRO | A | 242 | −8.234 | 19.577 | 27.285 | 1.00 | 32.60 | C |
| ATOM | 37 | CG | PRO | A | 242 | −7.827 | 18.915 | 26.040 | 1.00 | 37.83 | C |
| ATOM | 38 | N | ASP | A | 243 | −6.480 | 21.417 | 29.176 | 1.00 | 34.91 | N |
| ATOM | 39 | CA | ASP | A | 243 | −5.451 | 21.642 | 30.163 | 1.00 | 35.21 | C |
| ATOM | 40 | C | ASP | A | 243 | −4.812 | 20.307 | 30.500 | 1.00 | 38.35 | C |
| ATOM | 41 | O | ASP | A | 243 | −5.193 | 19.613 | 31.455 | 1.00 | 37.41 | O |
| ATOM | 42 | N | TYR | A | 244 | −3.865 | 19.930 | 29.652 | 1.00 | 34.76 | N |
| ATOM | 43 | CA | TYR | A | 244 | −3.152 | 18.662 | 29.719 | 1.00 | 34.71 | C |
| ATOM | 44 | C | TYR | A | 244 | −2.245 | 18.565 | 30.939 | 1.00 | 39.89 | C |
| ATOM | 45 | CB | TYR | A | 244 | −2.366 | 18.444 | 28.424 | 1.00 | 34.64 | C |

TABLE 10-continued

Atomic coordinates of P14 residues and of the residues involved in the binding of P14 to the β clamp, in the crystal of P14 peptide co-crystallized with the β ring.

| | | | | | | | | | | |
|---|---|---|---|---|---|---|---|---|---|---|
| TER | 46 | | TYR | A | 244 | | | | | |
| ATOM | 47 | NH1 | ARG | A | 246 | −9.362 | 18.335 | 34.959 | 1.00 | 56.46 N1+ |
| ATOM | 48 | CB | VAL | A | 247 | −4.800 | 14.658 | 32.377 | 1.00 | 45.61 C |
| ATOM | 49 | CG1 | VAL | A | 247 | −6.175 | 15.272 | 32.614 | 1.00 | 44.77 C |
| ATOM | 50 | CG2 | VAL | A | 247 | −4.260 | 15.077 | 31.013 | 1.00 | 45.81 C |
| TER | 51 | | VAL | A | 247 | | | | | |
| ATOM | 52 | O | GLY | A | 318 | −7.101 | −0.481 | 31.341 | 1.00 | 28.54 O |
| ATOM | 53 | N | PHE | A | 319 | −6.439 | −2.005 | 29.819 | 1.00 | 25.76 N |
| ATOM | 54 | CA | PHE | A | 319 | −6.062 | −1.039 | 28.794 | 1.00 | 25.29 C |
| ATOM | 55 | C | PHE | A | 319 | −6.489 | −1.419 | 27.399 | 1.00 | 26.95 C |
| ATOM | 56 | O | PHE | A | 319 | −6.510 | −2.591 | 27.065 | 1.00 | 25.62 O |
| ATOM | 57 | CB | PHE | A | 319 | −4.532 | −0.862 | 28.741 | 1.00 | 26.12 C |
| ATOM | 58 | CG | PHE | A | 319 | −3.977 | 0.004 | 29.823 | 1.00 | 26.52 C |
| ATOM | 59 | CD1 | PHE | A | 319 | −4.229 | 1.368 | 29.839 | 1.00 | 30.64 C |
| ATOM | 60 | CE1 | PHE | A | 319 | −3.731 | 2.174 | 30.867 | 1.00 | 31.78 C |
| ATOM | 61 | N | ASN | A | 320 | −6.726 | −0.410 | 26.564 | 1.00 | 23.99 N |
| ATOM | 62 | CA | ASN | A | 320 | −6.956 | −0.616 | 25.155 | 1.00 | 24.11 C |
| ATOM | 63 | C | ASN | A | 320 | −5.554 | −0.926 | 24.635 | 1.00 | 27.35 C |
| ATOM | 64 | O | ASN | A | 320 | −4.654 | −0.066 | 24.695 | 1.00 | 24.65 O |
| ATOM | 65 | CB | ASN | A | 320 | −7.569 | 0.636 | 24.508 | 1.00 | 23.58 C |
| ATOM | 66 | CG | ASN | A | 320 | −7.625 | 0.595 | 23.004 | 1.00 | 34.43 C |
| ATOM | 67 | ND2 | ASN | A | 320 | −8.716 | 1.031 | 22.426 | 1.00 | 24.70 N |
| TER | 68 | | ASN | A | 320 | | | | | |
| ATOM | 69 | CB | TYR | A | 323 | −3.987 | 3.146 | 23.786 | 1.00 | 24.01 C |
| ATOM | 70 | CG | TYR | A | 323 | −5.324 | 3.669 | 23.316 | 1.00 | 27.27 C |
| ATOM | 71 | CD2 | TYR | A | 323 | −6.338 | 3.953 | 24.224 | 1.00 | 27.85 C |
| ATOM | 72 | CE2 | TYR | A | 323 | −7.551 | 4.485 | 23.803 | 1.00 | 28.48 C |
| ATOM | 73 | cz | TYR | A | 323 | −7.760 | 4.733 | 22.459 | 1.00 | 39.89 C |
| TER | 74 | | TYR | A | 323 | | | | | |
| ATOM | 75 | O | SER | A | 343 | −8.221 | 1.305 | 36.401 | 1.00 | 35.47 O |
| ATOM | 76 | CA | VAL | A | 344 | −9.112 | 3.668 | 37.518 | 1.00 | 31.45 C |
| ATOM | 77 | C | VAL | A | 344 | −8.465 | 5.023 | 37.143 | 1.00 | 35.04 C |
| ATOM | 78 | O | VAL | A | 344 | −9.164 | 5.988 | 36.815 | 1.00 | 35.77 O |
| ATOM | 79 | CB | VAL | A | 344 | −10.398 | 3.839 | 38.375 | 1.00 | 35.78 C |
| ATOM | 80 | CG1 | VAL | A | 344 | −11.101 | 2.498 | 38.569 | 1.00 | 35.22 C |
| TER | 81 | | VAL | A | 344 | | | | | |
| ATOM | 82 | CB | SER | A | 346 | −3.897 | 8.687 | 33.543 | 1.00 | 33.22 C |
| ATOM | 83 | OG | SER | A | 346 | −3.189 | 9.493 | 34.475 | 1.00 | 39.59 O |
| TER | 84 | | SER | A | 346 | | | | | |
| ATOM | 85 | C | VAL | A | 360 | −1.708 | 8.441 | 28.606 | 1.00 | 31.20 C |
| ATOM | 86 | O | VAL | A | 360 | −2.317 | 8.921 | 27.649 | 1.00 | 30.76 O |
| ATOM | 87 | CB | VAL | A | 360 | −0.897 | 10.498 | 29.926 | 1.00 | 31.93 C |
| ATOM | 88 | CG1 | VAL | A | 360 | −2.031 | 10.304 | 30.938 | 1.00 | 32.54 C |
| ATOM | 89 | C | VAL | A | 361 | −4.106 | 6.199 | 29.791 | 1.00 | 28.46 C |
| ATOM | 90 | CG1 | VAL | A | 361 | −3.751 | 4.254 | 27.465 | 1.00 | 28.23 C |
| ATOM | 91 | N | MET | A | 362 | −5.362 | 6.501 | 29.534 | 1.00 | 27.43 N |
| ATOM | 92 | CA | MET | A | 362 | −6.410 | 6.303 | 30.527 | 1.00 | 28.06 C |
| ATOM | 93 | C | MET | A | 362 | −6.834 | 4.822 | 30.434 | 1.00 | 30.78 C |
| ATOM | 94 | O | MET | A | 362 | −7.011 | 4.331 | 29.325 | 1.00 | 29.96 O |
| ATOM | 95 | CB | MET | A | 362 | −7.591 | 7.238 | 30.220 | 1.00 | 30.87 C |
| ATOM | 96 | CG | MET | A | 362 | −8.518 | 7.477 | 31.376 | 1.00 | 34.33 C |
| ATOM | 97 | SD | MET | A | 362 | −7.736 | 8.227 | 32.828 | 1.00 | 37.58 s |
| ATOM | 98 | CE | MET | A | 362 | −9.105 | 8.087 | 34.005 | 1.00 | 34.59 C |
| ATOM | 99 | N | PRO | A | 363 | −6.981 | 4.091 | 31.569 | 1.00 | 26.83 N |
| ATOM | 100 | CA | PRO | A | 363 | −7.383 | 2.677 | 31.502 | 1.00 | 25.64 C |
| ATOM | 101 | C | PRO | A | 363 | −8.853 | 2.456 | 31.064 | 1.00 | 31.65 C |
| ATOM | 102 | O | PRO | A | 363 | −9.600 | 3.409 | 30.801 | 1.00 | 29.62 O |
| ATOM | 103 | CB | PRO | A | 363 | −7.148 | 2.203 | 32.941 | 1.00 | 26.32 C |
| ATOM | 104 | CG | PRO | A | 363 | −7.447 | 3.380 | 33.754 | 1.00 | 30.73 C |
| ATOM | 105 | CD | PRO | A | 363 | −6.797 | 4.505 | 32.971 | 1.00 | 26.98 C |
| ATOM | 106 | N | MET | A | 364 | −9.251 | 1.179 | 30.970 | 1.00 | 28.59 N |
| ATOM | 107 | CA | MET | A | 364 | −10.606 | 0.744 | 30.632 | 1.00 | 28.63 C |
| ATOM | 108 | C | MET | A | 364 | −11.156 | 0.010 | 31.848 | 1.00 | 33.94 C |
| ATOM | 109 | O | MET | A | 364 | −10.376 | −0.602 | 32.572 | 1.00 | 30.49 O |
| ATOM | 110 | CB | MET | A | 364 | −10.559 | −0.264 | 29.473 | 1.00 | 30.86 C |
| ATOM | 111 | CG | MET | A | 364 | −10.480 | 0.379 | 28.110 | 1.00 | 34.27 C |
| ATOM | 112 | SD | MET | A | 364 | −10.177 | −0.880 | 26.856 | 1.00 | 37.20 S |
| ATOM | 113 | CE | MET | A | 364 | −11.844 | −1.575 | 26.686 | 1.00 | 34.67 C |
| ATOM | 114 | N | ARG | A | 365 | −12.490 | 0.042 | 32.084 | 1.00 | 36.79 N |
| ATOM | 115 | CA | ARG | A | 365 | −13.039 | −0.701 | 33.225 | 1.00 | 38.26 C |
| ATOM | 116 | C | ARG | A | 365 | −13.003 | −2.213 | 32.924 | 1.00 | 41.53 C |
| ATOM | 117 | O | ARG | A | 365 | −13.457 | −2.647 | 31.869 | 1.00 | 41.37 O |
| ATOM | 118 | CB | ARG | A | 365 | −14.441 | −0.209 | 33.655 | 1.00 | 40.76 C |
| ATOM | 119 | CG | ARG | A | 365 | −14.900 | −0.881 | 34.954 | 1.00 | 49.70 C |
| ATOM | 120 | CD | ARG | A | 365 | −16.194 | −0.321 | 35.483 | 1.00 | 57.33 C |
| ATOM | 121 | NE | ARG | A | 365 | −15.967 | 0.754 | 36.451 | 1.00 | 62.68 N |
| ATOM | 122 | CZ | ARG | A | 365 | −16.403 | 1.998 | 36.291 | 1.00 | 83.24 C |

TABLE 10-continued

Atomic coordinates of P14 residues and of the residues involved in the binding of P14 to the β clamp, in the crystal of P14 peptide co-crystallized with the β ring.

| | | | | | | | | | | |
|---|---|---|---|---|---|---|---|---|---|---|
| ATOM | 123 | NH1 | ARG | A | 365 | −17.085 | 2.335 | 35.202 | 1.00 | 79.01 N1+ |
| ATOM | 124 | NH2 | ARG | A | 365 | −16.159 | 2.916 | 37.217 | 1.00 | 72.47 N |
| TER | 125 | | ARG | A | 365 | | | | | |
| HETATM | 126 | O | HOH | A | 393 | −12.258 | 0.479 | 23.904 | 1.00 | 30.49 O |
| HETATM | 127 | O | HOH | A | 434 | −11.324 | 4.559 | 22.768 | 1.00 | 39.46 O |
| HETATM | 128 | O | HOH | A | 453 | −10.378 | 2.373 | 23.903 | 1.00 | 29.67 O |
| HETATM | 129 | O | HOH | A | 463 | −8.977 | 20.736 | 30.414 | 1.00 | 61.87 O |
| HETATM | 130 | O | HOH | A | 490 | −11.833 | 19.233 | 26.362 | 1.00 | 59.30 O |
| HETATM | 131 | O | HOH | A | 494 | −9.709 | 19.924 | 32.759 | 1.00 | 46.54 O |
| HETATM | 132 | O | HOH | A | 516 | −16.291 | −3.291 | 31.343 | 1.00 | 50.13 O |
| HETATM | 133 | O | HOH | C | 45 | −6.988 | 2.274 | 27.402 | 1.00 | 24.52 O |
| HETATM | 134 | O | HOH | C | 219 | −14.432 | 8.577 | 32.316 | 1.00 | 42.19 O |
| HETATM | 135 | O | HOH | C | 236 | −12.880 | 18.057 | 33.132 | 1.00 | 45.93 O |
| HETATM | 136 | C | ACE | C | 367 | −14.148 | 1.368 | 29.378 | 1.00 | 30.45 C |
| HETATM | 137 | O | ACE | C | 367 | −13.835 | 1.713 | 30.502 | 1.00 | 36.32 O |
| HETATM | 138 | CH3 | ACE | C | 367 | −15.035 | 0.134 | 29.141 | 1.00 | 23.39 C |
| ATOM | 139 | N | GLN | C | 368 | −13.746 | 1.957 | 28.290 | 1.00 | 33.32 N |
| ATOM | 140 | CA | GLN | C | 368 | −12.873 | 3.100 | 28.115 | 1.00 | 32.69 C |
| ATOM | 141 | C | GLN | C | 368 | −13.283 | 4.349 | 28.853 | 1.00 | 33.34 C |
| ATOM | 142 | O | GLN | C | 368 | −14.330 | 4.821 | 28.622 | 1.00 | 32.62 O |
| ATOM | 143 | CB | GLN | C | 368 | −12.617 | 3.443 | 26.659 | 1.00 | 30.16 C |
| ATOM | 144 | CG | GLN | C | 368 | −11.470 | 4.502 | 26.458 | 1.00 | 29.48 C |
| ATOM | 145 | CD | GLN | C | 368 | −10.087 | 4.218 | 27.096 | 1.00 | 29.80 C |
| ATOM | 146 | NE2 | GLN | C | 368 | −9.514 | 3.231 | 26.666 | 1.00 | 25.11 N |
| ATOM | 147 | OE1 | GLN | C | 368 | −9.495 | 4.916 | 28.005 | 1.00 | 31.46 O |
| TER | 148 | | GLN | C | 368 | | | | | |
| HETATM | 149 | N | ALC | C | 369 | −12.348 | 4.783 | 29.710 | 1.00 | 32.73 N |
| HETATM | 150 | CA | ALC | C | 369 | −12.500 | 6.004 | 30.548 | 1.00 | 34.14 C |
| HETATM | 151 | C | ALC | C | 369 | −11.878 | 7.192 | 29.752 | 1.00 | 36.64 C |
| HETATM | 152 | O | ALC | C | 369 | −10.984 | 7.069 | 28.869 | 1.00 | 32.46 O |
| HETATM | 153 | CB | ALC | C | 369 | −11.739 | 5.830 | 31.889 | 1.00 | 34.55 C |
| HETATM | 154 | CG | ALC | C | 369 | −12.265 | 4.559 | 32.650 | 1.00 | 35.64 C |
| HETATM | 155 | CD1 | ALC | C | 369 | −13.808 | 4.654 | 32.962 | 1.00 | 39.49 C |
| HETATM | 156 | CD2 | ALC | C | 369 | −11.323 | 4.206 | 33.835 | 1.00 | 33.24 C |
| HETATM | 157 | CE1 | ALC | C | 369 | −14.214 | 3.964 | 34.302 | 1.00 | 41.77 C |
| HETATM | 158 | CE2 | ALC | C | 369 | −11.911 | 3.020 | 34.514 | 1.00 | 36.86 C |
| HETATM | 159 | CZ | ALC | C | 369 | −13.067 | 3.588 | 35.295 | 1.00 | 40.10 C |
| ATOM | 160 | N | ASP | C | 370 | −12.406 | 8.334 | 30.145 | 1.00 | 40.84 N |
| ATOM | 161 | CA | ASP | C | 370 | −12.054 | 9.670 | 29.629 | 1.00 | 43.94 C |
| ATOM | 162 | C | ASP | C | 370 | −10.905 | 10.238 | 30.494 | 1.00 | 41.92 C |
| ATOM | 163 | O | ASP | C | 370 | −10.900 | 10.094 | 31.706 | 1.00 | 39.99 O |
| ATOM | 164 | CB | ASP | C | 370 | −13.194 | 10.609 | 29.791 | 1.00 | 48.03 C |
| ATOM | 165 | CG | ASP | C | 370 | −14.398 | 10.233 | 29.003 | 1.00 | 55.27 C |
| ATOM | 166 | OD1 | ASP | C | 370 | −14.373 | 9.336 | 28.084 | 1.00 | 56.63 O |
| ATOM | 167 | OD2 | ASP | C | 370 | −15.398 | 10.873 | 29.360 | 1.00 | 59.41 O1− |
| ATOM | 168 | N | LEU | C | 371 | −9.929 | 10.917 | 29.882 | 1.00 | 43.04 N |
| ATOM | 169 | CA | LEU | C | 371 | −8.785 | 11.787 | 30.606 | 1.00 | 42.42 C |
| ATOM | 170 | C | LEU | C | 371 | −9.335 | 12.911 | 31.330 | 1.00 | 47.23 C |
| ATOM | 171 | O | LEU | C | 371 | −8.808 | 13.271 | 32.377 | 1.00 | 47.55 O |
| ATOM | 172 | CB | LEU | C | 371 | −7.621 | 12.265 | 29.726 | 1.00 | 37.30 C |
| ATOM | 173 | CG | LEU | C | 371 | −6.599 | 11.206 | 29.251 | 1.00 | 32.23 C |
| ATOM | 174 | CD1 | LEU | C | 371 | −5.841 | 11.622 | 27.996 | 1.00 | 27.72 C |
| ATOM | 175 | CD2 | LEU | C | 371 | −5.712 | 10.688 | 30.370 | 1.00 | 32.57 C |
| TER | 176 | | LEU | C | 371 | | | | | |
| HETATM | 177 | N | ZCL | C | 372 | −10.331 | 13.589 | 30.796 | 1.00 | 51.48 N |
| HETATM | 178 | CA | ZCL | C | 372 | −11.007 | 14.833 | 31.271 | 1.00 | 56.21 C |
| HETATM | 179 | C | ZCL | C | 372 | −12.356 | 14.343 | 31.982 | 1.00 | 59.74 C |
| HETATM | 180 | O | ZCL | C | 372 | −13.391 | 14.104 | 31.274 | 1.00 | 58.69 O |
| HETATM | 181 | CB | ZCL | C | 372 | −11.091 | 16.085 | 30.288 | 1.00 | 55.89 C |
| HETATM | 182 | CG | ZCL | C | 372 | −9.672 | 16.291 | 29.799 | 1.00 | 57.05 C |
| HETATM | 183 | CD1 | ZCL | C | 372 | −9.347 | 15.682 | 28.574 | 1.00 | 57.40 C |
| HETATM | 184 | CD2 | ZCL | C | 372 | −8.663 | 17.020 | 30.494 | 1.00 | 57.44 C |
| HETATM | 185 | CE1 | ZCL | C | 372 | −8.088 | 15.803 | 28.089 | 1.00 | 59.91 C |
| HETATM | 186 | CE2 | ZCL | C | 372 | −7.347 | 17.172 | 29.984 | 1.00 | 57.91 C |
| HETATM | 187 | CZ | ZCL | C | 372 | −7.057 | 16.515 | 28.746 | 1.00 | 57.04 C |
| HETATM | 188 | CLE1 | ZCL | C | 372 | −7.803 | 15.045 | 26.635 | 1.00 | 66.69 CL |
| HETATM | 189 | CLZ | ZCL | C | 372 | −5.507 | 16.525 | 27.966 | 1.00 | 50.27 CL |
| HETATM | 190 | OXT | ZCL | C | 372 | −12.339 | 14.160 | 33.254 | 1.00 | 61.54 O |
| END | | | | | | | | | | |

1.2.5. Thermodynamic Analysis of the Pseudo Peptides Interaction with the Ring.

ITC experiments were conducted on selected peptides in order to determine the thermodynamics parameters of their interaction with the ring (Table 11 and FIG. 8). Although the $K_d$ values determined in these experimental conditions were slightly different from those obtained by SPR, the same tendency was observed for all peptides (Table 11). The largest differences are observed for low affinity peptides (P1, P3, P6) while, for higher affinity peptides (P7, P11, P12, P13 and P14), both techniques yielded similar values. The introduction of modifications, Cha group in position 2 and p-methyl, p-chloro and p-bromo groups on $F_5$, increases the affinity of the ligand, reaching respectively about 380, 100, 65 and 150 nM range, as compared to the 1-2 μM affinity of the reference natural peptide P1 (Table 11). A strong correlation is observed between ΔH and ΔS values (FIG. 8), which reflects an enthalpy-entropy compensatory effect, already observed in other systems[21, 22]. This correlation accounts for the small ΔG variation among the various peptides (FIG. 8). As reported earlier[23], this correlation suggests that the observed desolvation of the pocket upon ligand interaction plays a major role in the binding process.

TABLE 11

ITC experiments on selected β binding peptides.

| Beta (μM) | Pep (μM) | Name | N | Kd (nM) | IC$_{50}$ SPR (nM) | ΔH (cal/Mol) | ΔS (cal/mol/deg) | ΔG (Kcal/mol) |
|---|---|---|---|---|---|---|---|---|
| 30 | 400 | P1 (SEQ ID No: 1) | 1.33 | 1579 | 8850 | −4087 | 12.8 | −7.9 |
|  |  | RQLVLGL | 1.31 | 2012 |  | −5500 | 7.6 | −7.7 |
| 30 | 400 | P3 (SEQ ID No: 3) | 1.54 | 2816 | 8620 | −5769 | 6.05 | −7.5 |
|  |  | RQLVLF | 1.45 | 2320 |  | −5699 | 6.6 | −7.6 |
| 30 | 400 | P6 (SEQ ID No: 6) | 1.11 | 820 | 1120 | −1.13 10$^4$ | −10.4 | −8.1 |
|  |  | AcQLDLF | 1.14 | 613 |  | −1.11 10$^4$ | −9.08 | −8.3 |
| 30 | 400 | P7 (SEQ ID No: 7) | 0.74 | 246 | 170 | −2.13 10$^4$ | −41.2 | −8.9 |
|  |  | AcQChaDLF | 0.76 | 222 |  | −2.05 10$^4$ | −38.5 | −8.9 |
| 20 | 400 | P11 (SEQ ID No: 11) | 0.95 | 401 | 260 | −1.48 10$^4$ | −20.4 | −8.6 |
|  |  | AcQChaDLpMeF | 0.95 | 362 |  | −1.44 10$^4$ | −19.0 | −8.6 |
| 20 | 400 | P12 (SEQ ID No: 12) | 1.02 | 89 | 160 | −1.5 10$^4$ | −18.1 | −9.6 |
|  |  | AcQChaDLpClF | 1.06 | 122 |  | −1.43 10$^4$ | −16.3 | −9.4 |
| 20 | 400 | P13 (SEQ ID No: 13) | 0.85 | 136 | 96 | −1.81 10$^4$ | −29.3 | −9.3 |
|  |  | AcQChaDLpBrF | 0.83 | 167 |  | −1.52 10$^4$ | −20.2 | −9.1 |
| 20 | 400 | P14 (SEQ ID No: 14) | 0.91 | 73 | 77 | −1.89 10$^4$ | −30.8 | −9.6 |
|  |  | AcQChaDLdiClF | 0.90 | 55 |  | −1.81 10$^4$ | −27.6 | −9.8 |

ΔG = ΔH−TΔS.

All experiments were performed at 25° C. Results from SPR experiments (IC50) are added for comparison purposes.

N: number of binding sites per β monomer.

The effect of the various modifications introduced in the peptides can be estimated from the ΔΔG values (see Table 12). The Cha moiety in position 2 contributes to the increased interaction by −0.66 kcal/mol as compared to the natural pentapeptide P6. While the introduction of a methyl substitution on the ring of the terminal phenylalanine residue is detrimental to the affinity (+0.25 kcal/mol), halogen modification results in a graduate effect on ligand affinity (p-bromo<p-chloro<3,4-dichloro). The chloro modification in para position contributes for the main part to the increased affinity (−0.6 kcal/mol). This contribution can result partly from an increased hydrophobic character of the halogen modified F residue[24], as well as from dehydration of both peptide and sub site 1[25] and reorganization of water molecules as observed by comparing free and bound β interacting pockets (FIG. 1AB). In comparison, the second chlorine atom (meta position) in P14 only contributes for −0.2 kcal/mol and the para-bromo modification contribution to the binding energy is two times lower (−0.28 kcal/mol) than the corresponding para-chloro modification.

TABLE 12 effects of modifications introduced in the various pentapeptides measured from the ΔΔG values extracted from ITC experiments data. The P6 sequence (AcQLDLF) is chosen as a reference. ΔΔG = ΔGj − ΔGi.

| | ΔGi/ΔGj | | | | | | | | | | |
|---|---|---|---|---|---|---|---|---|---|---|---|
| | P6/P7 | P7/P11 | P7/P12 | P7/P14 | P7/P13 | P11/P12 | P11/P14 | P11/P13 | P12/P14 | P13/P12 | P13/P14 |
| Compared residues | L/Cha | F/pMeF | F/pClF | F/diClF | F:pBrF | pMeF/pClF | pMeF/diClF | pMeF/pBrF | pClF/diClF | pBrF/pClF | pBrF/diClF |
| ΔΔG (Kcal/mol) | −0.66 | +0.25 | −0.6 | −0.8 | −0.28 | −0.85 | −1.05 | −0.53 | −0.2 | −0.32 | −0.52 |

1.3. Discussion.

1.3.1. The Fully Efficient β Binding Pocket is Formed Upon Ligand Binding.

Many cellular factors involved in replication and genome integrity survey processes require a peptide mediated interaction with the replisome sliding clamp in order to fulfill their function. This interaction has been structurally fully characterized in prokaryotes[16, 17, 18] and eucaryotes[2 26]. In our previously published structure (1OK7), the β ring interacts with only one peptide, leaving one binding pocket free[17]. This gives the opportunity to compare the structure of a peptide-free versus a peptide-bound pocket and to get insights into the dynamic of the pocket upon peptide binding. Although the general structures of the free or bound pockets are similar, as estimated by the Cα chain conformation (rmsd=0.36 Å), the side chains of several residues undergo major movements (FIG. 6), notably residues $M_{362}$ and $S_{346}$ side chains which are displaced in a concerted way, and residue $R_{365}$. The concerted shift of $M_{362}$ and $S_{346}$ side chains probably is a structural marker for the presence of a peptide ligand in the binding pocket. In absence of the ligand, these residues adopt a so-called close conformation where the $M_{362}$ side chain is oriented toward residue $H_{175}$ and separates subsite 1 and subsite 2 (PDB IDs 2POL, 1MMI and 1OK7 (monomer A)) (FIG. 6). Alternatively, in all β ring bound structures (1UNN, 1OK7 (monomer B), 3D1E, 3D1F), the residues are shifted by 180° in an open conformation, allowing the opening of a cleft joining the two subsites (FIG. 1BC). One exception is found in the structure of β co-crystallized with the Pol II peptide (3D1E) where no ligand is observed in monomer B, although the two residues adopt an open conformation[18]. This may result from a partial occupancy of the pocket, making difficult the detection of the peptide.

Residue $R_{365}$ is also shifted by an angle of 46° toward residue $L_{366}$, triggering the opening of a platform shaped by $R_{365}$, $P_{363}$, $M_{362}$ and $V_{344}$, where the $L_3$ residue of the peptide locates (FIG. 1BC). The global dynamic of this structural modification has been modeled, showing that, as the ligand binds into the pocket, a groove forms that joins subsite 1 and subsite 2, in which the extended peptide can adapt.

The correlation between side chains orientations and the presence of a peptide in the binding pocket suggests that these two side chains might play a strategic function in the ligand binding process. The pocket could adopt two configurations: a closed configuration where the $M_{362}$ side chains lies in the path between the two subsites of the pocket, thus impeding the formation of an efficient binding site (FIG. 1A). Alternatively, an open configuration where the $M_{362}$ side chains shifts by about 180°, allowing ligand binding into the groove that joins the two subsites, as well as the opening of the platform so that the peptide establishes optimal interactions. At present, it is not known if the fully efficient binding pocket is readily available at the surface of the protein, or is structured by the binding of a specific ligand, according to a bona fide induced fit model. Previous observations for a ligand binding site on the cytokine IL-2[27] reveal that a portion of the binding site is adaptive and can form a hydrophobic channel upon ligand binding. A similar adaptive process could occur for the β binding pocket and would ensure the binding specificity of ligand proteins. Although the details of the dynamic process of this binding site formation are not known yet, this observation is likely to have major implications for the design of high affinity ligands.

1.3.2. Structure-Based Design of High Affinity Ligands.

The inventors have studied the interaction of various peptides with the *E. coli* processivity ring. Starting from the natural sequence of the Pol IV DNA polymerase interacting peptide (P1, RQLVLGL, SEQ ID No: 1), they have sequentially modified the peptide in order to increase its interaction strength and concomitantly to limit its size. The affinities were measured by biochemical assays, SPR and ITC, and despite a difference in sensitivity of these various techniques, the relative affinities of the peptides were similar. From the P1-β complex (PDB 1OK7), a minimal acetylated peptide (P6, AcQLDLF) was first delineated and found to bind about eight times tighter than P1. Then, the crystallographic structure of the P1-β and P6-β complexes were used together with modelling informations to guide modifications at specific positions (corresponding to residues $L_2$ and $F_5$ of P6, AcQLDLF), resulting in a dramatic increase of the modified peptides affinity for the β ring interacting pocket. This gain essentially results from an increase in hydrophobic interactions. A first improvement was achieved by the introduction of a cyclohexylalanyl residue at the P6-L2 position. Although position 2 does not correspond to a major binding pocket on the β-clamp, the simple modification to a cyclohexylalanyl residue (P7) improved the affinity by a factor 6 with respect to the P6 peptide (Table 1), indicating that shallow secondary sites can still prove useful in a global optimization scheme.

The other interesting gain was achieved by the addition of halogen atoms on the benzyl ring of the F residue. Interestingly, the chlorine atom when introduced at the meta position, forms a halogen bond that further strengthens the interaction. P14, which combines both the Cha and a 3,4-dichloro phenylalanine residue, displays the highest affinity, around 60 (±10) nM as measured by ITC, which represents a 10 to 15 fold increase in binding as compared to P6 and a 4 fold increased as compared to the whole PolIV DNA polymerase. The double F ring substitution contributes for −0.8 kcal/mol to the overall interaction. The para-chloro substitution provides most of the contribution to the binding while the meta-chloro, involved in a halogen bond, only contributes for one fourth of the total free energy.

Interestingly, halogen substituted aromatic ligands were also recently independently identified for the β-clamp using a chemical library screening strategy. A compound, named RU67, was identified as a β ligand inhibiting the *E. coli* pol III enzyme with a Ki of 10 μM[18]. It contains a di-bromo substituted aromatic ring which is deeply inserted in sub site 1 and almost superimposes with the peptide $L_4$ residue of the Pol IV binding peptide. One bromine atom does not form any interaction while the other forms a halogen bond with β residue $T_{172}$ (d=3.02 Å and θ=133.21°). This latter interaction is similar to that observed for the chlorine atom in meta position of $F_5$ in P14.

This specific positioning of halogen substituted ligands in subsite 1 of the β-clamp contrasts with the wider range of positions occupied by natural amino acids in the same pocket. Indeed, the comparison of different structures of β in complex with various natural peptides (1OK7, 3D1E, 3D1F)[17, 18] reveals that, while most of the peptide residues adopt the same overall conformation within the pocket, the position of the last C-terminal residues of the interacting sequence varies in subsite 1. This suggests that no specific interaction is established with specific β residue, but instead that this hydrophobic interaction, delocalized in all subsite 1, contributes mainly to paste the peptide onto the β surface.

In conclusion, the structure-based approach described herein allows the design of ligands that bind two orders of magnitude tighter than the natural peptide P1, reaching the $10^{-8}$ M range, and 4 fold more than the Pol IV enzyme. This increase in affinity relies both on chemical substitutions introduced on the peptide that increase the hydrophobic interactions and on the fact that the bidentate interaction of the ligand in the binding pocket is retained. This interaction mode promotes the modeling of an efficient binding site, possibly through an induced-fit process.

Further designs of high affinity ligands should also take into account the dynamic nature of the binding site formation. These observations are likely to have major implications for the development of new antibiotic compounds.

Example 2

Synthesis and Functional Characterization of Further Peptides Derived from P7 (SEQ ID No: 7), P12 (SEQ ID No: 12), P14 (SEQ ID No: 14), P23-P30 (SEQ ID Nos: 23-30)

Compounds P23 to P28 (SEQ ID No: 23 to SEQ ID No: 28), which are analogues of P7 and P14, have been prepared to (i) remove carboxylic side functions and monitor the influence of R and guanidino groups and conformational constraint. Compounds P23 to P28 have been prepared as previously reported in example 1 starting from Fmoc-Phe Wang resin or from o-chlorotrityl chloride resin. The linear precursor of P29 (Ac-RQChaKLF-OH, P27, SEQ ID No: 27) is prepared as described in example 1. In the case of compound P30 (SEQ ID No: 30), the linear precursor P28 (SEQ ID No: 28) requires the use of a beta amino acid (Fmoc-beta-HPhe-OH) which is commercially available from Sigma-Aldrich. In the case of P29 and P30, lactam formation between the amino group of the lysine side chain and the C-terminal carboxylic function was performed using standard methods as described in the literature (Robert C. Reid, Giovanni Abbenante, Stephen M. Taylor, and David P. Fairlie; J. Org. Chem., 2003, 68 (11), pp 4464-4471). The cyclization which requires the activation and coupling of a peptidyl-Arg residue (P27 or P28) was carried out in DMF at room temperature using BOP as a coupling agent and diisopropylethylamine as the base and monitored by analytical RP-HPLC. Briefly, a solution of the fully deprotected peptide 27 or 28 (1 equivalent) in DMF (10-1M) and diisopropylethylamine (5.5 equivalent) was stirred at room temperature (about 20° C.) until homogeneous. Benzotriazole-1-yl-oxy-tris-(dimethylamino)-phosphonium hexafluorophosphate or BOP reagent (1.08 equivalent) was added, and the solution was stirred at room temperature (about 20° C.) for 2 h. A saturated Bicarbonate solution was added and the solid product was filtered off, washed on the filter with ether, and dried under high vacuum. The crude product was dissolved in 50% $CH_3CN$/50% water (1 L) and purified by C18 RP-HPLC. The peak containing the cyclic peptide was collected and lyophilized.

Example 3

New Peptides Derived from P14, SPR Experiments

Based on the crystals analysis, the inventors have used peptide P14 (Bu29) as a scaffold to derive new variants with the aim of deciphering new properties to the ligand such as increased affinity, increased solubility, or increased cell penetration.

TABLE 13 sequences of the P14 derivative peptides.

| Peptide name | Sequence | Mw | SEQ ID No: |
|---|---|---|---|
| P14 | Ac Q Cha D L diClF | | 14 |
| P14-4 | Ac R Q Cha N L diClF | 940 | 36 |
| P14-5 | Cin R Q Cha N L diClF | 1028 | 37 |
| P14-6 | Ac R Q Cha R L diClF | 980.5 | 38 |
| P14-7 | Ac R Q Cha R L F | 913 | 39 |
| P14-8 | Ac R Q Cha K L F | 886 | 40 |

Ac: acetyl group;
Cin: cinnamoyl group.

The rationale directing the design of these peptides was 1) to extend the interaction of the N-terminal part of the peptide with the edge of the binding pocket, 2) to take advantage of the position of the D residue of peptide P14, that points towards the solvent, to introduce positively charged residues that will increase the solubility and the membrane penetrating capabilities of the peptide.

The affinity of these peptides for the binding pocket was measured by SPR, by defining the concentration of ligand that challenges 50% of the binding of the natural peptide P1 (RQLVLGL), thus defining a Ki. Results are given in table 14

TABLE 14 relative affinity of P14 derivative peptides for the beta ring binding pocket, as measured by SPR experiments.

| Peptide name | Sequence | Ki (nM) | SEQ ID No: |
|---|---|---|---|
| P7 | Ac Q Cha D L F | 170 | 7 |
| P14 | Ac Q Cha D L diClF | 85 | 14 |
| P14-4 | Ac R Q Cha N L diClF | insoluble | 36 |
| P14-5 | Cin R Q Cha N L diClF | 3250 | 37 |
| P14-6 | Ac R Q Cha R L diClF | >10 000 | 38 |
| P14-7 | Ac R Q Cha R L F | >10 000 | 39 |
| P14-8 | Ac R Q Cha K L F | 904 | 40 |

CONCLUSIONS

None of the peptides is a better binder than P14. One of them, P14-8, still bind the target with a 1 µM affinity.

As compared to P14 (SEQ ID No: 14), the introduction of R and K residues in the sequence (P14-8, SEQ ID No: 40) results in a 10 fold decrease in affinity.

The diClF to F substitution results in a 2 fold decrease in affinity (compare P14 and P7). Thus the R and K substitutions in peptide P14-8 may contribute to a 5 fold decrease (1000/200) of the affinity as compared to P14.

P14-7 and P14-8 differ from each other by the $5^{th}$ residue (R for #7 and K for #8). Comparison of the relative affinity of these two peptides suggests that K residue is a better choice to maintain affinity. Moreover, comparing P7 and P14-7, which differ by R1 and R5 residues, indicates an affinity ratio of at least 50 (#10 000/200).

Altogether, this suggests that the K5 residue in P14-8 may contribute to decrease the affinity by a factor of 10 (P14-7/P7=5 and P14-8/P7=50).

REFERENCES

1. Kong, X. P., Onrust, R., O'Donnell, M. & Kuriyan, J. (1992). Three-dimensional structure of the beta subunit of *E. coli* DNA polymerase III holoenzyme: a sliding DNA clamp. *Cell* 69, 425-37.
2. Gulbis, J. M., Kelman, Z., Hurwitz, J., O'Donnell, M. & Kuriyan, J. (1996). Structure of the C-terminal region of p21(WAF1/CIP1) complexed with human PCNA. *Cell* 87, 297-306.
3. Shamoo, Y. & Steitz, T. A. (1999). Building a replisome from interacting pieces: sliding clamp complexed to a peptide from DNA polymerase and a polymerase editing complex. *Cell* 99, 155-66.
4. Matsumiya, S., Ishino, Y. & Morikawa, K. (2001). Crystal structure of an archaeal DNA sliding clamp: proliferating cell nuclear antigen from *Pyrococcus furiosus*. *Protein Sci* 10, 17-23.
5. Johnson, A. & O'Donnell, M. (2005). Cellular DNA replicases: components and dynamics at the replication fork. *Annu Rev Biochem* 74, 283-315.
6. Fuchs, R. P. & Fujii, S. (2007). Translesion synthesis in *Escherichia coli*: lessons from the NarI mutation hot spot. *DNA Repair (Amst)* 6, 1032-41.
7. Prakash, S., Johnson, R. E. & Prakash, L. (2005). Eukaryotic translesion synthesis DNA polymerases: specificity of structure and function. *Annu Rev Biochem* 74, 317-53.
8. Kleczkowska, H. E., Marra, G., Lettieri, T. & Jiricny, J. (2001). hMSH3 and hMSH6 interact with PCNA and colocalize with it to replication foci. *Genes Dev* 15, 724-36.
9. Lopez de Saro, F. J., Marinus, M. G., Modrich, P. & O'Donnell, M. (2006). The beta sliding clamp binds to multiple sites within MutL and MutS. *J Biol Chem* 281, 14340-9.
10. Dalrymple, B. P., Kongsuwan, K., Wijffels, G., Dixon, N. E. & Jennings, P. A. (2001). A universal protein-protein interaction motif in the eubacterial DNA replication and repair systems. *Proc Natl Acad Sci USA* 98, 11627-32.
11. Wagner, J., Fujii, S., Gruz, P., Nohmi, T. & Fuchs, R. P. (2000). The beta clamp targets DNA polymerase IV to DNA and strongly increases its processivity. *EMBO Rep* 1, 484-8.
12. Becherel, O. J., Fuchs, R. P. & Wagner, J. (2002). Pivotal role of the beta-clamp in translesion DNA synthesis and mutagenesis in *E. coli* cells. *DNA Repair (Amst)* 1, 703-8.
13. Lenne-Samuel, N., Wagner, J., Etienne, H. & Fuchs, R. P. (2002). The processivity factor beta controls DNA polymerase IV traffic during spontaneous mutagenesis and translesion synthesis in vivo. *EMBO Rep* 3, 45-9.
14. Heltzel, J. M., Maul, R. W., Scouten Ponticelli, S. K. & Sutton, M. D. (2009). A model for DNA polymerase switching involving a single cleft and the rim of the sliding clamp. *Proc Natl Acad Sci USA* 106, 12664-9.
15. Jeruzalmi, D., Yurieva, O., Zhao, Y., Young, M., Stewart, J., Hingorani, M., O'Donnell, M. & Kuriyan, J. (2001). Mechanism of processivity clamp opening by the delta subunit wrench of the clamp loader complex of *E. coli* DNA polymerase III. *Cell* 106, 417-28.
15a. Jeruzalmi D, O'Donnell M, Kuriyan J. (2001) Crystal structure of the processivity clamp loader gamma (gamma) complex of *E. coli* DNA polymerase III. *Cell* 106, 429-41.
16. Bunting, K. A., Roe, S. M. & Pearl, L. H. (2003). Structural basis for recruitment of translesion DNA polymerase Pol IV/DinB to the beta-clamp. *Embo J* 22, 5883-92.
17. Burnouf, D. Y., Olieric, V., Wagner, J., Fujii, S., Reinbolt, J., Fuchs, R. P. & Dumas, P. (2004). Structural and biochemical analysis of sliding clamp/ligand interactions suggest a competition between replicative and translesion DNA polymerases. *J Mol Biol* 335, 1187-97.
18. Georgescu, R. E., Yurieva, O., Kim, S. S., Kuriyan, J., Kong, X. P. & O'Donnell, M. (2008). Structure of a small-molecule inhibitor of a DNA polymerase sliding clamp. *Proc Natl Acad Sci USA* 105, 11116-21.
19. Wagner, J., Etienne, H., Fuchs, R. P., Cordonnier, A. & Burnouf, D. (2009). Distinct beta-clamp interactions govern the activities of the Y family PolIV DNA polymerase. *Mol Microbiol* 74, 1143-51.
20. Auffinger, P., Hays, F. A., Westhof, E. & Ho, P. S. (2004). Halogen bonds in biological molecules. *Proc Natl Acad Sci USA* 101, 16789-94.
21. Rinnenthal, J., Klinkert, B., Narberhaus, F. & Schwalbe, H. (2010). Direct observation of the temperature-induced melting process of the *Salmonella* fourU RNA thermometer at base-pair resolution. *Nucleic Acids Res* 38, 3834-47.

22. Strazewski, P. (2002). Thermodynamic correlation analysis: hydration and perturbation sensitivity of RNA secondary structures. *J Am Chem Soc* 124, 3546-54.
23. Ackroyd, P. C., Cleary, J. & Glick, G. D. (2001). Thermodynamic basis for sequence-specific recognition of ssDNA by an autoantibody. *Biochemistry* 40, 2911-22.
24. Voth, A. R. & Ho, P. S. (2007). The role of halogen bonding in inhibitor recognition and binding by protein kinases. *Curr Top Med Chem* 7, 1336-48.
25. Camacho, C. J., Kimura, S. R., DeLisi, C. & Vajda, S. (2000). Kinetics of desolvation-mediated protein-protein binding. *Biophys J* 78, 1094-105.
26. Vijayakumar, S., Chapados, B. R., Schmidt, K. H., Kolodner, R. D., Tainer, J. A. & Tomkinson, A. E. (2007). The C-terminal domain of yeast PCNA is required for physical and functional interactions with Cdc9 DNA ligase. *Nucleic Acids Res* 35, 1624-37.
27. Arkin, M. R., Randal, M., DeLano, W. L., Hyde, J., Luong, T. N., Oslob, J. D., Raphael, D. R., Taylor, L., Wang, J., McDowell, R. S., Wells, J. A. & Braisted, A. C. (2003). Binding of small molecules to an adaptive protein-protein interface. *Proc Natl Acad Sci USA* 100, 1603-8.
28. Goodman, M., Felix, A., Moroder, L. & Toniolo, C. H.-W. (2002). *Synthesis of Peptides and Peptidomimetics*. Methods of Organic Chemistry., Vol. E 22a-e: Thieme: Stuttgart, New York, 2002.
29. Neimark, J. & Briand, J. P. (1993). Development of a fully automated multichannel peptide synthesizer with integrated TFA cleavage capability. *Pept Res* 6, 219-28.
30. Kaiser, E., Colescott, R. L., Bossinger, C. D. & Cook, P. I. (1970). Color test for detection of free terminal amino groups in the solid-phase synthesis of peptides. *Anal Biochem* 34, 595-8.
31. Lafont, V., Schaefer, M., Stote, R., Altschuh, D. & Dejaegere, A. (2007). Protein-protein recognition and interaction hot spots in an antigen-antibody complex: free energy decomposition identifies "efficient amino acids. *Proteins: Structure Function and Bioinformatics* 67, 418-434.
32. Kollman, P. A., Massova, I., Reyes, C., Kuhn, B., Huo, S., Chong, L., Lee, M., Lee, T., Duan, Y., Wang, W., Donini, O., Cieplak, P., Srinivasan, J. & Case, D. A. (2000). Calculating structures and free energies of complex molecules: combining molecular mechanics and continuum models. *Acc. Chem. Res.* 33, 889-97.
33. Gohlke, H., Kiel, C. & Case, D. A. (2003). Insights into protein-protein binding by binding free energy calculation and free energy decomposition for the Ras-Raf and Ras-RalGDS complexes. *J Mol Biol* 330, 891-913.
34. Brooks, B. R., Bruccoleri, R. E., Olafson, B. D., States, D. J., Swaminathan, S. & M., K. (1983). CHARMM: A Program for Macromolecular Energy Minimization and Dynamics Calculations. *J. Comp. Chem* 4, 187-217.
35. MacKerell, A. D., Bashford, D., Bellott, M., Dunbrack, R. L., Evanseck, J. D., Field, M. J., Fischer, S., Gao, J., Guo, H., Ha, S., Joseph-McCarthy, D., Kuchnir, L., Kuczera, K., Lau, F. T. K., Mattos, C., Michnick, S., Ngo, T., Nguyen, D. T., Prodhom, B., Reiher, W. E., Roux, B., Schlenkrich, M., Smith, J. C., Stote, R., Straub, J., Watanabe, M., Wiorkiewicz-Kuczera, J., Yin, D. & Karplus, M. (1998). All-atom empirical potential for molecular modeling and dynamics studies of proteins. *J Phys Chem B* 102, 3586-3616.
36. Hendsch, Z. S. & Tidor, B. (1999). Electrostatic interactions in the GCN4 leucine zipper: substantial contributions arise from intramolecular interactions enhanced on binding. *Protein Sci* 8, 1381-92.
37. Gouda, H., Kuntz, I. D., Case, D. A. & Kollman, P. A. (2003). Free energy calculations for theophylline binding to an RNA aptamer: Comparison of MM-PBSA and thermodynamic integration methods. *Biopolymers* 68, 16-34.
38. Miranker, A. & Karplus, M. (1991). Functionality maps of binding sites: a multiple copy simultaneous search method. *Proteins* 11, 29-34.
39. Majeux, N., Scarsi, M., Apostolakis, J., Ehrhardt, C. & Caflisch, A. (1999). Exhaustive docking of molecular fragments with electrostatic solvation. *Proteins* 37, 88-105.
40. Sirockin, F., Sich, C., Improta, S., Schaefer, M., Saudek, V., Froloff, N., Karplus, M. & Dejaegere, A. (2002). Structure activity relationship by NMR and by computer: a comparative study. *J Am Chem Soc* 124, 11073-84.
41. Majeux, N., Scarsi, M. & Caflisch, A. (2001). Efficient electrostatic solvation model for protein-fragment docking. *Proteins* 42, 256-68.
42. Biertumpfel, C., Basquin, J., Suck, D. & Sauter, C. (2002). Crystallization of biological macromolecules using agarose gel. *Acta Crystallogr D Biol Crystallogr* 58, 1657-9.
43. Kabsch, W. (1993). Automatic processing of rotation diffraction data from crystals of initially unknown symmetry and cell constants. *J Appl Crystallogr* 26, 795-800.
44. Collaborative Computational Project, N. (1994). The CCP4 suite: programs for protein crystallography. *Acta Crystallogr D Biol Crystallogr* D50, 760-763.
45. Adams, P. D., Grosse-Kunstleve, R. W., Hung, L. W., Loerger, T. R., McCoy, A. J. & al., e. (2002). PHENIX: building new software for automated crystallographic structure determination. *Acta Crystallogr D Biol Crystallogr* D50 58, 1948-1954.
46. Emsley, P. & Cowtan, K. (2004). Coot: model-building tools for molecular graphics. *Acta Crystallogr D Biol Crystallogr* D50 60, 2126-2132.
47. Brünger, A. T., Adams, P. D., Clore, G. M., Delano, W. L., Gros, P., Grosse-Kuntsleve, R. V. & al., e. (1998). Crystallography and NMR system: a new software suite for macromolecular structure determination. *Acta Crystallog. sect. D* 54, 905-921.
48. Chen, V. B., Arendall, W. B. r., Headd, J. J., Keedy, D. A., Immormino, R. M., Kapral, G. J., Murray, L. W. & Richardson, J. S. R., D. C. (2010). MolProbity: all-atom structure validation for macromolecular crystallography. *Acta Crystallographica D* 66, 12-21.
49. DeLano, W. L. (2008). The PyMOL Molecular Graphics System. DeLano Scientific LLC., Palo Alto, Calif., USA.
50. Dallmann H G et al. (1995). DnaX complex of *Escherichia coli* DNA polymerase III holoenzyme. Central role of tau in initiation complex assembly and in determining the functional asymmetry of holoenzyme. J Biol Chem. 270 (49):29555-62.

The invention claimed is:

1. A compound of formula (I)

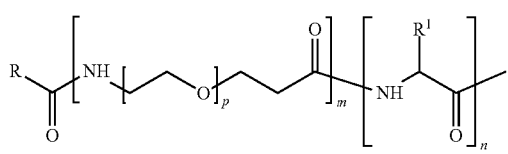

(I)

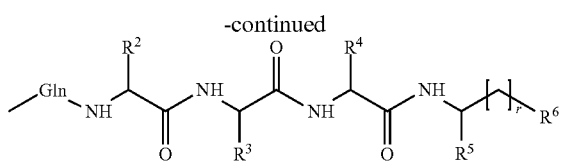

-continued wherein

Gln is glutamine;

R is selected from the group consisting of a $C_{1-12}$-alkyl group optionally substituted by a $C_{6-10}$-aryl group, a $C_{2-12}$-alkenyl group optionally substituted by a $C_{6-10}$-aryl group, a $C_{3-6}$-cycloalkyl group, a $C_{6-10}$-aryl group optionally substituted by a $C_{1-4}$-alkyl, and a $C_{1-5}$-alkyl-$(O\!-\!CH_2\!-\!CH_2)_t\!-\!$ group with t being an integer from 0 to 20 inclusive;

$R^1$ is the side chain of arginine or lysine;

$R^2$ is a $-\!(CH_2)\!-\!C_{3-6}$-cycloalkyl group optionally substituted by a halogen and/or by a group selected from the group consisting of $-\!NH_2$, $-\!NH\!-\!CO\!-\!R^a$, $-\!CO_2H$, $-\!NHR^a$ and $-\!NR^aR^b$, wherein $R^a$ and $R^b$ are independently a $C_{1-4}$-alkyl group;

$R^3$ is selected from the group consisting of a $C_{1-8}$-alkyl group, the side chain of arginine or lysine, $-\!(CH_2)_q\!-\!CO_2R^{7a}$, $-\!(CH_2)_q\!-\!CO\!-\!NHR^{7b}$, $-\!CH_2OR^8$ and $-\!(CH_2)_qNHR^9$, wherein q is 1, 2, 3 or 4, $R^{7a}$ is a hydrogen atom, a $C_{1-8}$-alkyl group, a $C_{4-12}$-alkylene group forming together with $R^6$ a lactone or a polyether ring, or a $C_{4-12}$-alkenylene, forming together with $R^6$ a lactone or a polyether ring, $R^{7b}$ is a hydrogen atom, a $C_{1-8}$-alkyl group, or $-\!(CH_2)_{q'}\!-\!NH\!-\!$ with q' being an integer between 2 and 8 inclusive and forming together with $R^6$ a lactam, $R^8$ is a hydrogen atom, a $C_{1-8}$-alkyl group, a $C_{4-12}$-alkylene group forming together with $R^6$ a lactone or a polyether ring, or a $C_{4-12}$-alkenylene, forming together with $R^6$ a lactone or a polyether ring, $R^9$ is a hydrogen atom, or $R^9$ together with $R^6$ form a lactam;

$R^4$ is a $C_{1-8}$-alkyl group optionally substituted by a $C_{3-6}$-cycloalkyl group, or a halogen-$C_{1-4}$-alkyl group;

$R^5$ is selected from the group consisting of a $-\!(CH_2)\!-\!C_{3-6}$-cycloalkyl group; $-\!(CH_2\!-\!CH_2)\!-\!C_{3-6}$-cycloalkyl group; a $-\!(CH_2)\!-\!C_{6-10}$-aryl group optionally substituted by a halogen, a $C_{1-2}$ alkyl group and/or a $C_{1-2}$ alkoxy group; a $-\!(CH_2\!-\!CH_2)\!-\!C_{6-10}$-aryl group optionally substituted by a halogen, a $C_{1-2}$ alkyl group and/or a $C_{1-2}$ alkoxy group; a $-\!(CH_2)\!-\!C_{6-10}$-heteroaryl group optionally substituted by a halogen and/or a $C_{1-2}$ alkyl group; and a $-\!(CH_2\!-\!CH_2)\!-\!C_{5-10}$-heteroaryl group optionally substituted by a halogen and/or a $C_{1-2}$ alkyl group;

$R^6$ is $-\!CO_2H$, $-\!CO_2R^{10}$, $-\!CO\!-\!NH_2$, $-\!CO\!-\!NHR^{10}$, $-\!OR^{10}$ when r is 1 or 2, $-\!NH\!-\!CO\!-\!NHR^{10}$ when r is 1 or 2, or $R^6$ is $-\!CO\!-\!$, $-\!CO\!-\!O\!-\!$ or $-\!O\!-\!$ and forms a lactam, a lactone, or a polyether ring with $R^{7a}$, $R^{7b}$, $R^8$ or $R^9$; wherein $R^{10}$ is a $C_{1-8}$-alkyl group optionally substituted by a $C_{6-10}$-aryl group; a $C_{3-6}$-cycloalkyl group; a $C_{6-10}$-aryl group optionally substituted by a halogen, a $C_{1-2}$-alkyl group and/or a $C_{1-2}$-alkoxy group;

m is 0 or 1;

n is an integer from 0 to 9 inclusive;

p is an integer from 0 to 10 inclusive;

r is 0, 1 or 2.

2. The compound of claim 1, wherein

R is a $C_{1-8}$-alkyl group optionally substituted by a $C_{6-10}$-aryl group, a $C_{2-8}$-alkenyl group optionally substituted by a $C_{6-10}$-aryl group or a $C_{1-6}$-alkyl-$(O\!-\!CH_2\!-\!CH_2)_t\!-\!$ group with t being an integer from 0 to 10 inclusive.

3. The compound of claim 1, wherein

R is a $C_{1-4}$-alkyl group optionally substituted by a $C_{6-10}$-aryl group or a $C_{2-4}$-alkenyl group optionally substituted by a $C_{6-10}$-aryl group.

4. The compound of claim 1, wherein n is an integer comprised between 1 and 5 inclusive.

5. The compound of claim 1, wherein n is 0.

6. The compound of claim 1, wherein $R^2$ is a $-\!(CH_2)\!-\!C_{3-6}$-cycloalkyl group.

7. The compound of claim 1, wherein $R^4$ is a $C_{1-5}$-alkyl group or a $C_{1-2}$-alkyl group optionally substituted by a $C_{3-6}$-cycloalkyl group.

8. The compound of claim 1, wherein $R^5$ is a $-\!(CH_2)\!-\!C_{6-10}$-aryl group optionally substituted by a halogen, a $C_{1-2}$ alkyl group and/or a $C_{1-2}$ alkoxy group.

9. The compound of claim 1, wherein $R^3$ is selected from the group consisting of a $C_{1-8}$-alkyl group, the side chain of arginine or lysine, $-\!(CH_2)_q\!-\!CO_2R^{7a}$, $-\!(CH_2)_q\!-\!CO\!-\!NHR^{7b}$, $-\!CH_2OR^8$, and $-\!(CH_2)_qNHR^9$, wherein q is 1, 2, 3, 4, $R^{7a}$ is a hydrogen atom, or a $C_{1-8}$-alkyl group, $R^{7b}$ is a hydrogen atom, or a $C_{1-8}$-alkyl group, $R^8$ is a hydrogen atom, a $C_{1-8}$-alkyl group, $R^9$ is a hydrogen atom;

and $R^6$ is $-\!CO_2H$, $-\!CO_2R^{10}$, $-\!CO\!-\!NH_2$, $-\!CO\!-\!NHR^{10}$, $-\!OR^{10}$ when r is 1 or 2, $-\!NH\!-\!CO\!-\!NHR^{10}$ when r is 1 or 2; wherein $R^{10}$ is a $C_{1-8}$-alkyl group optionally substituted by a $C_{6-10}$-aryl group; a $C_{3-6}$-cycloalkyl group; a $C_{6-10}$-aryl group optionally substituted by a halogen, a $C_{1-2}$-alkyl group and/or a $C_{1-2}$-alkoxy group.

10. The compound of claim 1, wherein $R^3$ is selected from the group consisting of the side chain of arginine, the side chain of lysine, $-\!(CH_2)_q\!-\!CO_2R^{7a}$ and $-\!(CH_2)_q\!-\!CO\!-\!NHR^{7b}$, wherein q is 1, 2, 3 or 4, $R^{7a}$ is a hydrogen atom, or a $C_{1-8}$-alkyl group, and $R^{7b}$ is a hydrogen atom, or a $C_{1-8}$-alkyl group.

11. The compound of claim 1, wherein $R^6$ is $-\!CO_2H$ or $-\!CO\!-\!NH_2$.

12. The compound of claim 1, wherein $R^3$ is selected from the group consisting of $-\!(CH_2)_q\!-\!CO_2R^{7a}$, $-\!(CH_2)_q\!-\!CO\!-\!NHR^{7b}$, $-\!CH_2OR^8$, and $-\!(CH_2)_qNHR^9$, wherein q is 1, 2, 3 or 4, $R^{7a}$ is a $C_{4-8}$-alkylene group forming together with $R^6$ a lactone or a polyether ring, or a $C_{4-8}$-alkenylene, forming together with $R^6$ a lactone or a polyether ring, $R^{7b}$ is $-\!(CH_2)_{q'}\!-\!NH\!-\!$ with q' being an integer from 2 to 8 inclusive and forming together with $R^6$ a lactam, $R^8$ is a $C_{4-8}$-alkylene group forming together with $R^6$ a lactone or a polyether ring, or a $C_{4-8}$-alkenylene, forming together with $R^6$ a lactone or a polyether ring, $R^9$ together with $R^6$ form a lactam;

$R^6$ is $-\!CO\!-\!$, $-\!CO\!-\!O\!-\!$ or $-\!O\!-\!$ and forms a lactam, a lactone, or a polyether ring with $R^{7a}$, $R^{7b}$, $R^8$ or $R^9$.

13. The compound of claim 1, which is selected from the group consisting of Ac-Gln-Cha-Asp-Leu-Phe (SEQ ID NO:7), Ac-Gln-Cha-Asp-Leu-pMePhe (SEQ ID NO:11), Ac-Gln-Cha-Asp-Leu-pClPhe (SEQ ID NO:12), Ac-Gln-Cha-Asp-Leu-pBrPhe (SEQ ID NO:13), Ac-Gln-Cha-Asp-Leu-diClPhe (SEQ ID NO:14), Ac-Gln-Cha-Asp-hLeu-Phe (SEQ ID NO:16), and Ac-Gln-Cha-Asp-Cha-Phe (SEQ ID NO:17).

14. The compound of claim 1, wherein the affinity of said compound for the interacting pocket of the bacterial β ring is at least twice the affinity of the acetylated peptide of sequence AcQLDLF (SEQ ID NO:6) with said interacting pocket.

15. A pharmaceutical composition comprising, as an active agent, a compound according to claim 1.

16. A method of treating an infection by *E. coli* in a subject in need thereof comprising administering the compound of claim 1 to the subject.

* * * * *

SEQUENCE LISTING

<160> NUMBER OF SEQ ID NOS: 40

<210> SEQ ID NO 1
<211> LENGTH: 7

```
<212> TYPE: PRT
<213> ORGANISM: Artificial Sequence
<220> FEATURE:
<223> OTHER INFORMATION: Synthetic peptide

<400> SEQUENCE: 1

Arg Gln Leu Val Leu Gly Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Arg Gln Leu Val Leu Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Arg Gln Leu Val Leu Phe
1               5

<210> SEQ ID NO 4
<211> LENGTH: 6
<212> TYPE: PRT
<213> ORGANISM: Artificial
<220> FEATURE:
<223> OTHER INFORMATION: Synthetic peptide

<400> SEQUENCE: 4

Arg Gln Leu Val Phe Leu
1               5

<210> SEQ ID NO 5
<211> LENGTH: 5
<212> TYPE: PRT
<213> ORGANISM: Artificial
<220> FEATURE:
<223> OTHER INFORMATION: Synthetic peptide

<400> SEQUENCE: 5

Gln Leu Asp Leu Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 6

Gln Leu Asp Leu Phe
1               5
```

```
<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (beta-cyclohexyl-L-alanyl)

<400> SEQUENCE: 7

Gln Xaa Asp Leu Phe
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = hCha (homocyclohexylalanine)

<400> SEQUENCE: 8

Gln Xaa Asp Leu Phe
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = hLeu (homoleucine)

<400> SEQUENCE: 9

Gln Xaa Asp Leu Phe
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = NptGly (neopentylglycul)
<220> FEATURE:
```

```
<221> NAME/KEY: MISC_FEATURE
<222> LOCATION: (2)..(2)
<223> OTHER INFORMATION: Xaa = NptGly (neopentylglycyl)

<400> SEQUENCE: 10

Gln Xaa Asp Leu Phe
1               5

<210> SEQ ID NO 11
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MOD_RES
<222> LOCATION: (5)..(5)
<223> OTHER INFORMATION: METHYLATION Xaa = p-MeF (p-methylphenylalanine)
<220> FEATURE:
<221> NAME/KEY: MISC_FEATURE
<222> LOCATION: (5)..(5)

<400> SEQUENCE: 11

Gln Xaa Asp Leu Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (5)..(5)
<223> OTHER INFORMATION: Xaa = pClF (p-chloro-phenylalanine)

<400> SEQUENCE: 12

Gln Xaa Asp Leu Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
```

```
<222> LOCATION: (5)..(5)
<223> OTHER INFORMATION: Xaa = pBrF (p-bromo-phenylalanine)

<400> SEQUENCE: 13

Gln Xaa Asp Leu Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (5)..(5)
<223> OTHER INFORMATION: Xaa = diClF (3,4-dichloro-phenylalanine)

<400> SEQUENCE: 14

Gln Xaa Asp Leu Xaa
1               5

<210> SEQ ID NO 15
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION

<400> SEQUENCE: 15

Arg Gln Leu Val Leu Phe
1               5

<210> SEQ ID NO 16
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (4)..(4)
<223> OTHER INFORMATION: Xaa = hLeu (homoleucine)

<400> SEQUENCE: 16

Gln Xaa Asp Xaa Phe
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: Non-natural sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (4)..(4)
<223> OTHER INFORMATION: Xaa = Cha (cyclohexylalanine)

<400> SEQUENCE: 17

Gln Xaa Asp Xaa Phe
1               5

<210> SEQ ID NO 18
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (4)..(4)
<223> OTHER INFORMATION: Xaa = hCha (homocyclohexylalanine)

<400> SEQUENCE: 18

Gln Xaa Asp Xaa Phe
1               5

<210> SEQ ID NO 19
<211> LENGTH: 5
<212> TYPE: PRT
<213> ORGANISM: Artificial Sequence
<220> FEATURE:
<223> OTHER INFORMATION: Non-natural sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (4)..(4)
<223> OTHER INFORMATION: Xaa = NptGly (neopentylglycyl)

<400> SEQUENCE: 19

Gln Xaa Asp Xaa Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Non-natural peptide
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (5)..(5)
<223> OTHER INFORMATION: Xaa = Cha (cyclohexylalanine)

<400> SEQUENCE: 20

Gln Xaa Asp Leu Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)

<400> SEQUENCE: 21

Gln Xaa Asp Leu Trp
1               5

<210> SEQ ID NO 22
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (5)..(5)
<223> OTHER INFORMATION: Xaa = Atda (2-amino-tetradecanoic acid)

<400> SEQUENCE: 22

Gln Xaa Asp Leu Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
```

```
<221> NAME/KEY: MISC_FEATURE
<222> LOCATION: (5)..(5)
<223> OTHER INFORMATION: Xaa = di-chloro-phenylalanine carboxamide

<400> SEQUENCE: 23

Gln Xaa Asn Leu Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: addition of a cinnamoy group
<220> FEATURE:
<221> NAME/KEY: MISC_FEATURE
<222> LOCATION: (3)..(3)
<223> OTHER INFORMATION: Xaa = Cha (cyclohexylalanine)
<220> FEATURE:
<221> NAME/KEY: MISC_FEATURE
<222> LOCATION: (6)..(6)
<223> OTHER INFORMATION: Xaa = di-chloro-phenylalanine carboxamide

<400> SEQUENCE: 24

Arg Gln Xaa Asn Leu Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha (cyclohexylalanine)
<220> FEATURE:
<221> NAME/KEY: MISC_FEATURE
<222> LOCATION: (6)..(6)
<223> OTHER INFORMATION: Xaa = di-chloro-phenylalanine carboxamide

<400> SEQUENCE: 25

Arg Gln Xaa Arg Leu Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Non-natural sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Cha (cyclohexylalanine)
<220> FEATURE:
<221> NAME/KEY: MISC_FEATURE
<222> LOCATION: (5)..(5)
<223> OTHER INFORMATION: Xaa = di-chloro-phenylalanine carboxamide
```

```
<400> SEQUENCE: 26

Gln Xaa Arg Leu Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: Non-natural sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha (cyclohexylalanine)

<400> SEQUENCE: 27

Arg Gln Xaa Lys Leu Phe
1               5

<210> SEQ ID NO 28
<211> LENGTH: 6
<212> TYPE: PRT
<213> ORGANISM: Artificial Sequence
<220> FEATURE:
<223> OTHER INFORMATION: Non-natural sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha (cyclohexylalanine)
<220> FEATURE:
<221> NAME/KEY: MISC_FEATURE
<222> LOCATION: (6)..(6)
<223> OTHER INFORMATION: Xaa = beta homophenylalanine

<400> SEQUENCE: 28

Arg Gln Xaa Lys Leu Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: Non-natural sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha (cyclohexylalanine)
<220> FEATURE:
<221> NAME/KEY: MISC_FEATURE
<222> LOCATION: (4)..(6)
<223> OTHER INFORMATION: The peptide is cyclized between residues K
      and F

<400> SEQUENCE: 29

Arg Gln Xaa Lys Leu Phe
1               5

<210> SEQ ID NO 30
```

```
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha (cyclohexylalanine)
<220> FEATURE:
<221> NAME/KEY: MISC_FEATURE
<222> LOCATION: (4)..(6)
<223> OTHER INFORMATION: The peptide is cyclicized between residues K
      and beta homophenylalanine
<220> FEATURE:
<221> NAME/KEY: MISC_FEATURE
<222> LOCATION: (6)..(6)
<223> OTHER INFORMATION: Xaa = beta homophenylalanine

<400> SEQUENCE: 30

Arg Gln Xaa Lys Leu Xaa
1               5

<210> SEQ ID NO 31
<211> LENGTH: 4
<212> TYPE: PRT
<213> ORGANISM: Escherichia coli

<400> SEQUENCE: 31

Ala Ser Arg Gln
1

<210> SEQ ID NO 32
<211> LENGTH: 7
<212> TYPE: PRT
<213> ORGANISM: Escherichia coli

<400> SEQUENCE: 32

Arg Gln Leu Val Leu Gly Leu
1               5

<210> SEQ ID NO 33
<211> LENGTH: 5
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = Cha

<400> SEQUENCE: 33

Xaa Phe Gln Leu Asp
1               5

<210> SEQ ID NO 34
<211> LENGTH: 30
<212> TYPE: DNA
<213> ORGANISM: Artificial
<220> FEATURE:
<223> OTHER INFORMATION: Synthetic primer
```

```
<400> SEQUENCE: 34
gtaaaacgac ggccagtgcc aagcttagtc                                       30

<210> SEQ ID NO 35
<211> LENGTH: 90
<212> TYPE: DNA
<213> ORGANISM: Artificial
<220> FEATURE:
<223> OTHER INFORMATION: Synthetic primer

<400> SEQUENCE: 35
ccatgattac gaattcagtc atcaccggcg ccacagacta agcttggcac tggccgtcgt      60
tttacaacgt cgtgactggg aaaaccctgg                                       90

<210> SEQ ID NO 36
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha
<220> FEATURE:
<221> NAME/KEY: MISC_FEATURE
<222> LOCATION: (6)..(6)
<223> OTHER INFORMATION: Xaa = diClF

<400> SEQUENCE: 36

Arg Gln Xaa Asn Leu Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: Addition of a cinnamoyl group
<220> FEATURE:
<221> NAME/KEY: MISC_FEATURE
<222> LOCATION: (3)..(3)
<223> OTHER INFORMATION: Xaa = Cha
<220> FEATURE:
<221> NAME/KEY: MISC_FEATURE
<222> LOCATION: (6)..(6)
<223> OTHER INFORMATION: Xaa = diClF

<400> SEQUENCE: 37

Arg Gln Xaa Asn Leu Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: Non-natural peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha
<220> FEATURE:
<221> NAME/KEY: MISC_FEATURE
<222> LOCATION: (6)..(6)
<223> OTHER INFORMATION: Xaa = diClF

<400> SEQUENCE: 38

Arg Gln Xaa Arg Leu Xaa
1               5

<210> SEQ ID NO 39
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha

<400> SEQUENCE: 39

Arg Gln Xaa Arg Leu Phe
1               5

<210> SEQ ID NO 40
<211> LENGTH: 6
<212> TYPE: PRT
<213> ORGANISM: Artificial Sequence
<220> FEATURE:
<223> OTHER INFORMATION: Non-natural peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Cha

<400> SEQUENCE: 40

Arg Gln Xaa Lys Leu Phe
1               5
```